US008394974B2

(12) United States Patent
Kondo et al.

(10) Patent No.: US 8,394,974 B2
(45) Date of Patent: Mar. 12, 2013

(54) PROCESS FOR PRODUCING OPTICALLY ACTIVE CHROMENE OXIDE COMPOUND

(75) Inventors: Shoichi Kondo, Funabashi (JP);
Kowichiro Saruhashi, Funabashi (JP);
Hisayuki Watanabe, Funabashi (JP);
Tsutomu Katsuki, Fukuoka (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 920 days.

(21) Appl. No.: 12/224,941

(22) PCT Filed: Mar. 9, 2007

(86) PCT No.: PCT/JP2007/054730
§ 371 (c)(1),
(2), (4) Date: Sep. 22, 2008

(87) PCT Pub. No.: WO2007/105658
PCT Pub. Date: Sep. 20, 2007

(65) Prior Publication Data
US 2009/0043100 A1    Feb. 12, 2009

(30) Foreign Application Priority Data

Mar. 10, 2006  (JP) ................................. 2006-066818
Mar. 24, 2006  (JP) ................................. 2006-084285

(51) Int. Cl.
*C07D 493/06* (2006.01)
*C07D 491/12* (2006.01)
(52) U.S. Cl. ........................................ 549/387; 546/65
(58) Field of Classification Search .................. 549/387; 546/65
See application file for complete search history.

(56) References Cited

U.S. PATENT DOCUMENTS

| 5,352,814 A | 10/1994 | Katsuki et al. |
| 5,639,889 A | 6/1997 | Katsuki et al. |
| 6,897,332 B2 | 5/2005 | Belokon et al. |
| 7,022,876 B2 | 4/2006 | Blacker et al. |
| 7,812,184 B2 * | 10/2010 | Kondo et al. ................. 549/531 |
| 2003/0199706 A1 | 10/2003 | Belokon et al. |
| 2004/0068140 A1 | 4/2004 | Blacker et al. |
| 2005/0192454 A1 | 9/2005 | North et al. |

FOREIGN PATENT DOCUMENTS

| JP | A-56-057785 | 5/1981 |
| JP | A-56-057786 | 5/1981 |
| JP | A-58-188880 | 11/1983 |
| JP | A-02-000141 | 1/1990 |
| JP | A-05-301878 | 11/1993 |
| JP | A-07-285983 | 10/1995 |
| JP | A-08-245668 | 9/1996 |
| JP | A-10-087650 | 4/1998 |
| JP | A-11-209366 | 8/1999 |
| JP | A-11-335384 | 12/1999 |
| JP | A-2001-151767 | 6/2001 |
| JP | A-2004-505097 | 2/2004 |
| JP | A-2004-526710 | 9/2004 |
| RU | 2 204 562 C2 | 5/2003 |
| WO | WO 95/21172 | 8/1995 |
| WO | WO 2005/080368 A2 | 9/2005 |
| WO | WO 2005-090357 A1 | 9/2005 |
| WO | WO 2006/087874 A1 | 8/2006 |

OTHER PUBLICATIONS

Gullotti et al., "Schiff Base Complexes of Oxocations. Part III. Oxotitanium (IV) Complexes with Tetradentate Optically Active Schiff Bases," Inorganica Chimica Acta, vol. 15, No. 2, pp. 129-136, 1975.
Sawada et al., "Titanium-Salan-Catalyzed Asymmetric Epoxidation with Aqueous Hydrogen Peroxide as the Oxidant," Angew. Chem. Int. Ed., vol. 45, No. 21, pp. 3478-3480, 2006.
Matsumoto et al., "Jiko Soshikika Sareta Titanium Nikakusakutai o Shokubai ni Mochiiru Fusei Epoxidation," CSJ: The Chemical Society of Japan Koen Yokoshu, vol. 85, No. 2, p. 1102, 2005.
Matsumoto et al.; "Construction of Pseudo-Heterochiral and Homochiral Di-μ-oxotitanium (Schiff base) Dimers and Enantioselective Epoxidation Using Aqueous Hydrogen Peroxide," Angewandte Chemie Int. Ed., vol. 44, pp. 4935-4939, 2005.
Guiotto et al., "Methylfuroquinolinones: New Furocoumarin Isosters as Potential Photoreagents Toward DNA," Journal of Heterocyclic Chemistry, vol. 26, pp. 917-924, 1989.
Konno et al.,"Improved Procedures for Preparation of 2-Pyridones and 2-Hydroxymethylpyridines from Pyridine N-Oxides," Heterocycles, vol. 24, No. 8, pp. 2169-2172, 1986.
Burton et al., "Halogeno-o-phenylendiamines and Derived Heterocycles. Reductive Fission of Benzotriazoles to o-Phenylenediamines," Journal of the Chemical Society, vol. C, Part 1, pp. 1268-1273, 1968.
Kluge et al., "First Syntheses of Natural Products with the 2, 7-Dihydroxy-2H-1, 4-benzoxazin-3 (4H)-one Skeleton," Journal of Heterocyclic Chemistry, vol. 32, pp. 395-402, 1995.
Sakamoto et al.,"Facile Synthesis of 2-Substituted Indoles from o-Bromoaniline," Heterocycles, vol. 24, No. 1, pp. 31-32, 1986.
Cross et al., "The Chemistry of Extractives from Hardwoods. Part XXXII. Adifoline, an Alkaloid from *Adina cordifolia*," Journal of the Chemical Society, pp. 2714-2725, 1961.
Song et al., "Improved Synthesis of Quinaldines by the Skraup Reaction," Journal of Heterocyclic Chemistry, vol. 30, pp. 17-21, 1993.
Belley et al., "Synthesis of N-Aminoindole Ureas from Ethyl 1-Amino-6-(trifluoromethyl)-*1H*-indole-3-carboxylate," Synthesis, No. 2, pp. 222-225, 2001.
Kitahara et al., "Synthesis of Eupomatidines 1, 2 and 3 and Related Compounds Including Iminoquinolinequinone Structure," Tetrahedron, vol. 53, No. 17, pp. 6001-6010, 1997.
Tsuji et al., "Ruthenium Complex Catalyzed N-Heterocyclization. Syntheses of Quinolines and Indole Derivatives from Aminoarenes and 1, 3-Propanediol of Glycols," Journal of Organic Chemistry, vol. 52, No. 9, pp. 1673-1680, 1987.
Shuman et al., "An Improved Synthesis of Homoproline and Derivatives," Journal of Organic Chemistry, vol. 55, No. 2, pp. 738-741, 1990.
North et al., "Synthesis of 6-Cyano-2,2-dimethyl-2H-1-benzopyran and Other Substituted 2, 2-Dimethyl-2H-1-benzopyrans," Journal of Organic Chemistry, vol. 60, No. 11, pp. 3397-3400, 1995.
Jones et al., "Inhibitors of Cyclic AMP Phosphodiesterase. 1. Analogues of Cilostramide and Anagrelide," Journal of Medicinal Chemistry, vol. 30, No. 2, pp. 295-303, 1987.
Evans et al., "Synthesis and Antihypertensive Activity of 6, 7-Disubstituted trans-4-Amino-3, 4-dihydro-2, 2-dymethyl-2H-1-benzopyran-3-ols," Journal of Medicinal Chemistry, vol. 27, No. 9, pp. 1127-1131, 1984.
Ashwood et al., "Synthesis and Antihypertensive Activity of 4-(Cyclic amido)-2H-1-benzopyrans", Journal of Medicinal Chemistry, vol. 29, No. 11, pp. 2194-2201, 1986.
Wright et al., "Subtype-Selective N-Methyl -D-Aspartate Receptor Antagonists: Synthesis and Biological Evaluation of 1-(Heteroarylalkynyl)-4-benzylpoperidines," Journal of Medicinal Chemistry, vol. 43, No. 18, pp. 3408-3419, 2000.

Liu et al., "The Syntheses of Pyrazino-Containing Sultines and Their Application in Diels-Alder Reactions with Electron-Poor Olefins and [60] Fullerene," Journal of Organic Chemistry, vol. 65, No. 11, p. 3395-3403, 2000.
Li et al., "Synthesis of 3-Aryl and 3-Heterocyclic Quinoxalin-2-ylamines via Pd-Catalyzed Cross-Coupling Reactions," Tetrahedron Letters, vol. 40, pp. 4507-4510, 1999.
Fernandez et al., "Metallation of 2(1H)-Quinolinone: Synthesis of 3-Substituted Compounds," Synthesis, pp. 1362-1364, 1995.
Yang et al., "A Concise Regiospecific Synthesis of 8, 8-Dimethyl-2H, 8H-Pyrano[6,5-h] Quinolin-2-one and related Compounds," Tetrahedron Letters, vol. 40, pp. 4504-4506, 1999.
Sun et al., "The First Regiospecific Synthesis of 8, 8-Dimethyl-2H, 8H-pyrano[2,3-h]quinolin-2-one and Related Compounds," Synthesis, pp. 1249-1251, 1997.
Sabol et al., "A Novel and Efficient Synthesis of 2, 3-Dichloroquinoline," Synthetic Communications, vol. 30, No. 3, pp. 427-432, 2000.
Kitteringham et al., "A Simple Method for the Synthesis of Unsymmetrical Ureas," Synthetic Communications, vol. 30, No. 11, pp. 1937-1943, 2000.
Ambati et al., "A Facile Synthesis of 2-N(Methyl Amino) Benzothiazoles," Synthetic Communications, vol. 27, No. 9, pp. 1487-1493, 1997.
Imor et al., "An Improved Preparation of 4, 7-Phenanthrolino-5, 6:5',6'-Pyrazine," Synthetic Communications, vol. 26, No. 11, pp. 2197-2203, 1996.
Osborne et al., "Regioselective Alkoxydehalogenation of 2,4-Dihalogenoquinolines and a Reinvestigation of Bromination of 2-Methoxyquinoline," J. Chem. Soc. Perkin Trans., vol. 1, pp. 181-184, 1993.
Sakamoto et al., "Studies on Pyrimidine Derivatives. XXII. Site-selective Oxidation of Di-methylpyrimidines with Selenium Dioxide to Pyrimidine-monoaldehydes," Chem. Pharm. Bull., vol. 29, No. 9, pp. 2485-2490, 1981.
Ahmed et al., "Quinoxaline Derivatives. XII. The Reactions of Quinoxaline 1, 4-Dioxides with Acetic Anhydride," Bull. Chem. Soc. Jpn., vol. 60, No. 3, pp. 1145-1148, 1987.
Chemical Encyclopedia, M., 1995, vol. 4, p. 596, "Titanium Organic Components," with English-language translation.
European Search Report for European Application No. 07738215.8, mailed Jan. 27, 2011.
Russian Office Action for Russian Application No. 2008 140171/04 (052005), mailed Feb. 17, 2010.

\* cited by examiner

*Primary Examiner* — Charanjit Aulakh
(74) *Attorney, Agent, or Firm* — Oliff & Berridge, PLC

(57) ABSTRACT

[PROBLEMS] To provide an efficient process for producing an optically active chromene oxide compound which is an important intermediate for a benzopyran compound effective in the treatment of arrhythmia.
[MEANS FOR SOLVING PROBLEMS] The process for producing an optically active chromene oxide compound comprises using an optically active titanium complex represented by, e.g., the formula (1) or (2)

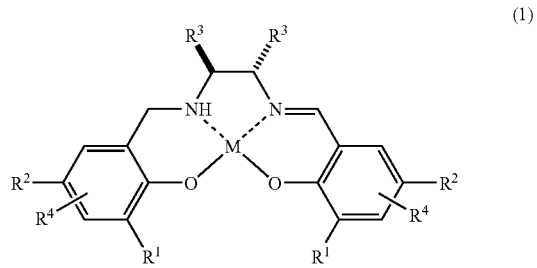

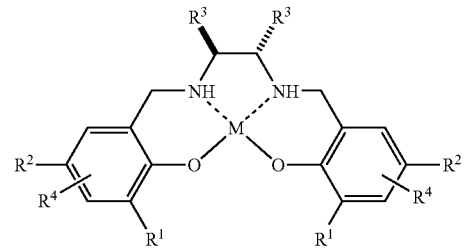

as a catalyst to asymmetrically oxidize an optically active chromene compound with high enantioselectivity in high chemical yield.

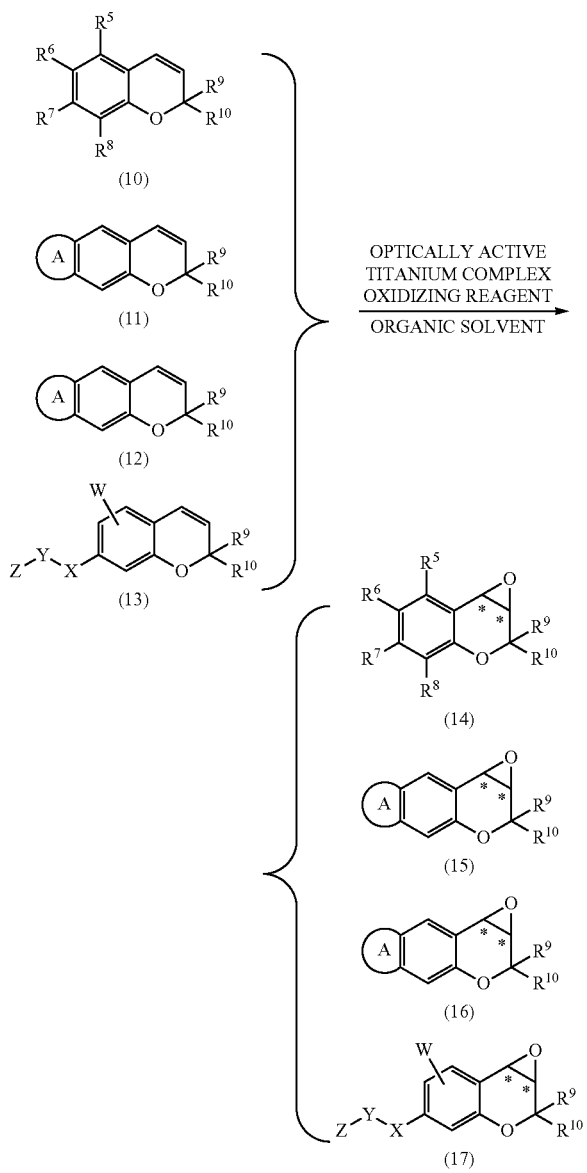

25 Claims, No Drawings

PROCESS FOR PRODUCING OPTICALLY ACTIVE CHROMENE OXIDE COMPOUND

TECHNICAL FIELD

The present invention relates to an efficient process for producing an optically active chromene oxide compound which is an important intermediate for a benzopyran compound being effective in the treatment of arrhythmia.

BACKGROUND ART

A benzopyran compound which is useful for an antiarrhythmic drug and a process for producing the same have been disclosed. That is, a benzopyran compound is produced by asymmetric epoxidation of chromene compound using an optically active manganese complex to obtain an optically active chromene oxide compound and then ring-opening the epoxide with an amine compound (see Patent Document 1).

A process for producing an optically active chromene oxide compound by asymmetric epoxidation of chromene compound using an optically active manganese complex has already been disclosed (see Patent Document 2, Patent Document 3, Patent Document 4, Patent Document 5 and Patent Document 6). In the above-described patent documents, production examples of optically active chromene oxide compounds using optically active manganese complexes as catalysts and iodosobenzene, sodium hypochlorite or 30% hydrogen peroxide aqueous solution as co-oxidizing reagent have been described.

For an asymmetric oxidation reaction using an optically active manganese complex, an additive called for an axial ligand such as 4-phenylpyridine-N-oxide is needed other than a co-oxidizing reagent, so that a different process for producing an optically active chromene oxide without using an axial donor ligand has been desired.

In contrast, it has been described that even 0.01 to 0.2 mol % use of an asymmetric optically active manganese complex can produce an optically active chromene oxide compound in high chemical yield and optical yield (see Patent Document 7). However, only the example of iodosobenzene used as co-oxidizing reagent is described in this patent document. Accordingly, more advantageous and efficient process for producing has been desired.

In an optically active titanium complex, it has been reported that use of a di-μ-oxotitanium-salalen complex provides a highly enantioselective reaction in the asymmetric epoxidation of various simple olefins not having heteroatom(s). However, there were no examples of olefinic compounds having heteroatom(s) and chromene compounds in the report (Non-patent Document 8).

[Patent Document 1] Japanese Patent Application Publication No. JP-A-2001-151767
[Patent Document 2] Japanese Patent Application Publication No. JP-A-05-301878
[Patent Document 3] Japanese Patent Application Publication No. JP-A-07-285983
[Patent Document 4] Japanese Patent Application Publication No. JP-A-08-245668
[Patent Document 5] WO 2005/090357A1
[Patent Document 6] WO 2005/080368A2
[Patent Document 7] Japanese Patent Application Publication No. JP-A-11-335384
[Non-patent Document 8] K. Matsumoto, Y. Sawada, B. Saito, K. Sakai and T. Katsuki, Angew. Chem. Int. Ed. (2005), 44, 4935-4939.

DISCLOSURE OF THE INVENTION

Problem to be Solved by the Invention

A process for producing an optically active chromene oxide compound which is an important intermediate for a benzopyran compound effective in the treatment of arrhythmia is provided.

Means for Solving the Problem

As the result of an intensive investigation of process for producing an optically active chromene oxide compound which is an important intermediate for a benzopyran compound effective in the treatment of arrhythmia, the inventors of the present invention have discovered that an optically active chromene oxide compound can be produced in high enantio-selectivity and high chemical yield by using an optically active titanium complex as a catalyst, and have accomplished the present invention.

According to a first aspect of the present invention, a process for producing an optically active chromene oxide compound represented by formula (14), formula (15), formula (16) or formula (17):

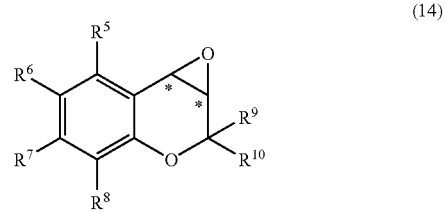

(14)

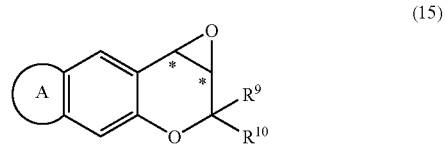

(15)

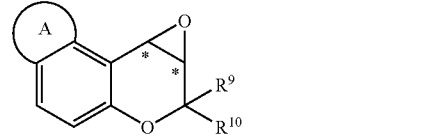

(16)

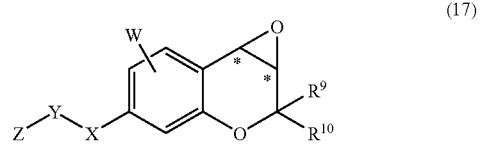

(17)

(in which $R^5$, $R^6$, $R^7$, $R^8$, $R^9$, $R^{10}$, A, W, X, Y and Z are the same as described below and an absolute configuration of the carbon atoms indicated by * are (R) or (S)), the process includes:

asymmetrically epoxidizing a chromene compound represented by the formula (10), formula (11), formula (12) or formula (13) with an oxidizing reagent in a solvent;

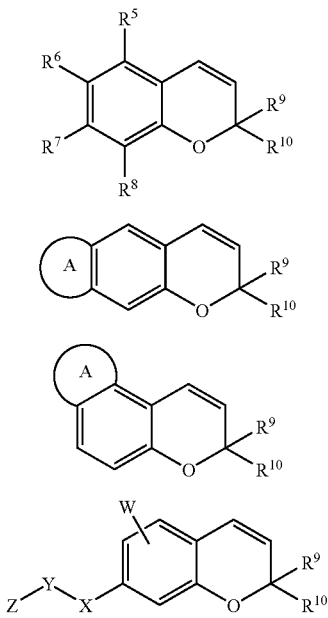

(in which $R^5$, $R^6$, $R^7$ and $R^8$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom, $C_{6-10}$ aryl group (the $C_{6-10}$ aryl group may be optionally substituted with a halogen atom, hydroxy group, cyano group, nitro group, $C_{1-4}$ alkyl group or $C_{1-4}$ alkoxy group)), $C_{1-4}$ alkylcarbonyl(N—$C_{1-4}$ alkyl)amino group (the alkylcarbonyl(N-alkyl)amino group may be optionally substituted with a halogen atom), $C_{1-4}$ alkoxycarbonyl group (the alkoxycarbonyl group may be optionally substituted with a halogen atom), $C_{6-10}$ arylcarbonylamino group (the arylcarbonylamino group may be substituted with a halogen atom, $C_{1-4}$ alkyl group, $C_{1-4}$ alkoxy group, cyano group or nitro group), $C_{6-10}$ arylcarbonyl (N—$C_{1-4}$ alkyl)amino group (the arylcarbonyl(N-alkyl)amino group may be substituted with a halogen atom, $C_{1-4}$ alkyl group, $C_{1-4}$ alkoxy group, cyano group or nitro group), benzylcarbonylamino group, formyl group, carbamoyl group, $C_{1-4}$ alkylsulfonyl group, $C_{6-10}$ arylsulfony group (the alkylsulfonyl group and arylsulfony group may be substituted with a halogen atom, $C_{1-4}$ alkyl group, $C_{1-4}$ alkoxy group, cyano group or nitro group), sulfamoyl group, $C_{1-4}$ alkylsulfonamide group, $C_{6-10}$ arylsulfonamide group (the alkylsulfonamide group and arylsulfonamide group may be substituted with a halogen atom, $C_{1-4}$ alkyl group, $C_{1-4}$ alkoxy group, cyano group or nitro group), bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis($C_{6-10}$ arylsulfone)imide group (arylsulfone of the bis (arylsulfone)imide group may be substituted with a halogen atom, $C_{1-4}$ alkyl group, $C_{1-4}$ alkoxy group, cyano group or nitro group), or (N,N'—($C_{1-4}$ alkylsulfone) ($C_{6-10}$ arylsulfone))imide group (alkylsulfone and arylsulfone of the (N,N'-(alkylsulfone) (arylsulfone))imide group may be substituted with a halogen atom, $C_{1-4}$ alkyl group, $C_{1-4}$ alkoxy group, cyano group or nitro group);

$R^9$ and $R^{10}$ in the formula (10) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

$R^9$ and $R^{10}$ in the formula (11) and formula (12) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

partial ring structure A in the formula (11) and formula (12) represents a partial structure being represented by 5-, 6- or 7-membered ring forming a fused ring with a benzene ring part (each of the 5-, 6- or 7-membered ring may be optionally substituted with h $R^{11}$ ($R^{11}$ is a halogen atom, hydroxy group, $C_{1-6}$ alkyl group (the alkyl group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-6}$ alkoxy group (the alkoxy group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), nitro group, cyano group, formyl group, formamide group, carbamoyl group, sulfo group, sulfoamino group, sulfamoyl group, sulfonyl group, amino group, carboxyl group, $C_{1-6}$ alkylamino group, di-$C_{1-6}$ alkylamino group, $C_{1-6}$ alkylcarbonylamino group, $C_{1-6}$ alkylsulfonamide group, $C_{6-14}$ arylsulfonamide group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, $C_{1-6}$ alkylsulfonyl group, $C_{6-14}$ arylsulfonyl group, or $C_{6-14}$ arylcarbonyl group (the alkylamino group, dialkylamino group, alkylcarbonylamino group, alkylsulfonamide group, arylsulfonamide group, alkylaminocarbonyl group, dialkylaminocarbonyl group, alkylcarbonyl group, alkoxycarbonyl group, alkylsulfonyl group, arylsulfonyl group, and arylcarbonyl group may be optionally substituted with a halogen atom); h is an integer of 1 to 6 and when h is an integer of 2 to 6, each $R^{11}$ may be the same or different); 1 to 3 of oxygen atom(s), nitrogen atom(s) or sulfur atom(s) can be contained singly or in combination as constituent atoms of the ring; the number of unsaturated bond(s) in the ring containing unsaturated bond(s) in benzene ring condensed is 1, 2 or 3 and carbon atom(s) composing the ring may be carbonyl or thiocarbonyl);

X in the formula (13) represents $NR^{20}$ ($R^{20}$ means a hydrogen atom or $C_{1-4}$ alkyl group);

Y in the formula (13) represents a bond, SO or $SO_2$;

Z in the formula (13) represents a $C_{1-4}$ alkyl group (the alkyl group may be optionally substituted with 1 to 5 halogen atom(s) or a phenyl group (the phenyl group may be optionally substituted with a $C_{1-4}$ alkyl group)) or phenyl group (the phenyl group may be optionally substituted with a $C_{1-4}$ alkyl group);

W in the formula (13) represents a hydrogen atom, hydroxy group, $C_{1-6}$ alkoxy group (the alkoxy group may be optionally substituted with a halogen atom), halogen atom, $C_{1-4}$ alkyl group or $C_{1-6}$ alkylsulfonamide group (the alkyl group and alkylsulfonamide group may be optionally substituted with a halogen atom); and $R^9$ and $R^{10}$ in the formula (13) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom or $C_{1-6}$ alkoxy group (the alkoxy group may be optionally substituted with a halogen atom) or hydroxy group) or $C_{1-6}$ alkoxy group (the alkoxy group may be optionally substituted with a halogen atom)));

by using any of optically active titanium complexes represented by the formula (1), formula (1'), formula (2), formula (2'), formula (3), formula (3'), formula (4) and formula (4') as a catalyst, (1)
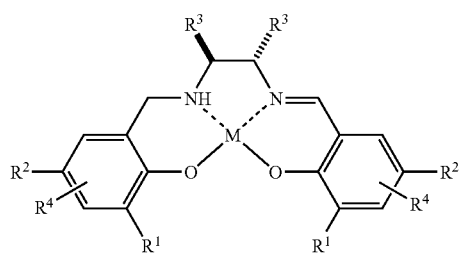

(1')
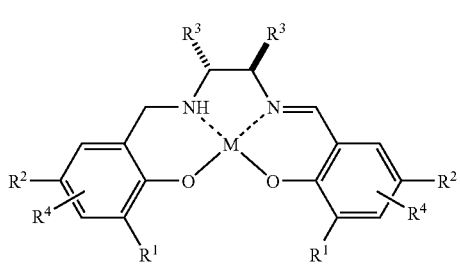

(2)
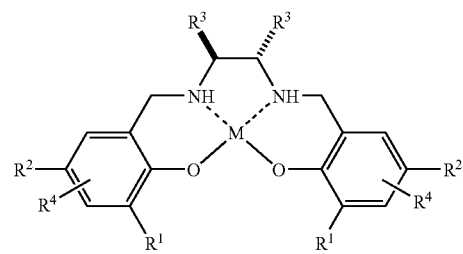

(2')
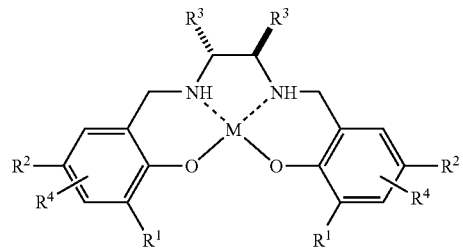

(3)
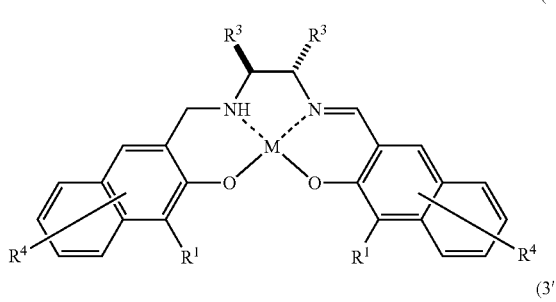

(3')
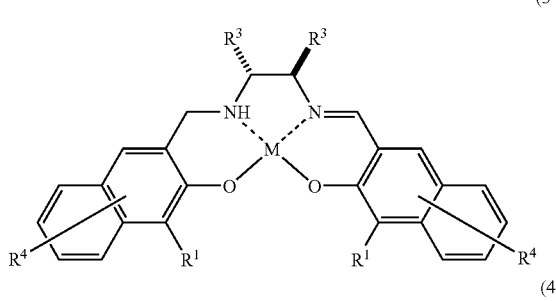

(4)
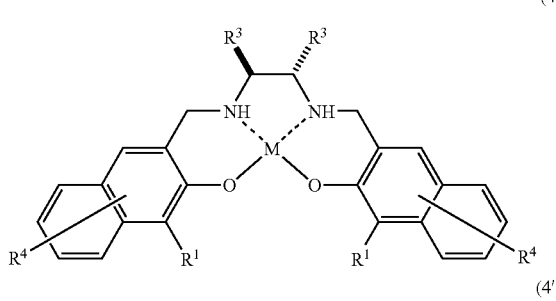

(4')
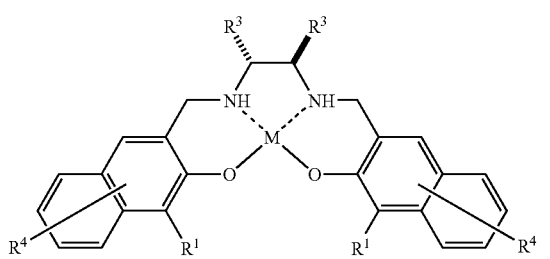

in which R¹ in the formula (1), formula (1'), formula (2), formula (2'), formula (3), formula (3'), formula (4) and formula (4') represents a hydrogen atom, halogen atom, $C_{1-4}$ alkyl group, $C_{1-4}$ alkoxy group, $C_{6-12}$ aryloxy group, or $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group, and is optically active or optically non-active);

R² represents a hydrogen atom, halogen atom, $C_{1-4}$ alkyl group, $C_{1-4}$ alkoxy group, $C_{6-12}$ aryloxy group, or $C_{6-18}$ aryl group;

R³ represents a $C_{1-4}$ alkyl group, $C_{6-18}$ aryl group, or $C_{3-5}$ bivalent group when two R³ form a ring together;

R⁴ each independently represent a hydrogen atom, halogen atom, $C_{1-4}$ alkyl group, $C_{1-4}$ alkoxy group, nitro group or cyano group;

M represents $TiJ^1J^2$ (in $TiJ^1J^2$, Ti represents a titanium atom, and $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group,

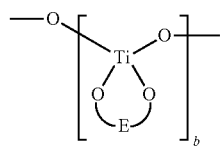

(5)

(in which, in partial structure of O-E-O, O represents an oxygen atom and O-E-O is represented by following formula (6) in formula (1); O-E-O is represented by following formula (6') in formula (1'); O-E-O is represented by following formula (7) in formula (2); O-E-O is represented by following formula (7') in formula (2'); O-E-O is represented by following formula (8) in formula (3); O-E-O is represented by following formula (8') in formula (3'); O-E-O is represented by following formula (9) in formula (4); and O-E-O is represented by following formula (9') in formula (4');

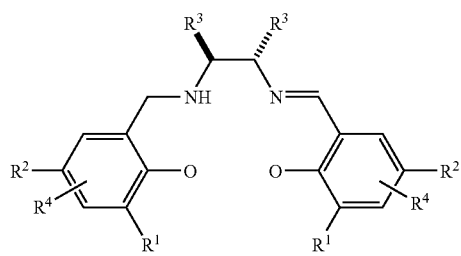

(6)

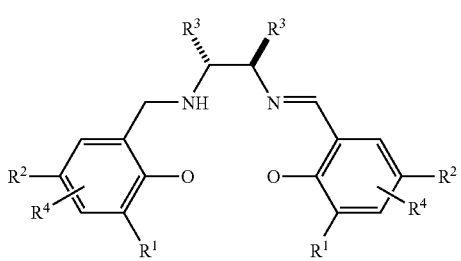

(6')

-continued

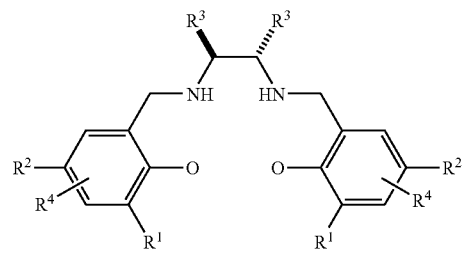

(7)

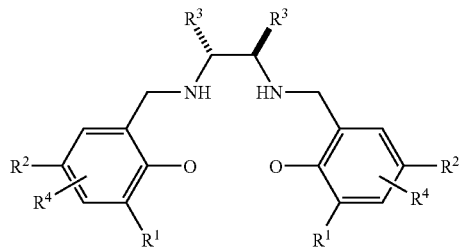

(7')

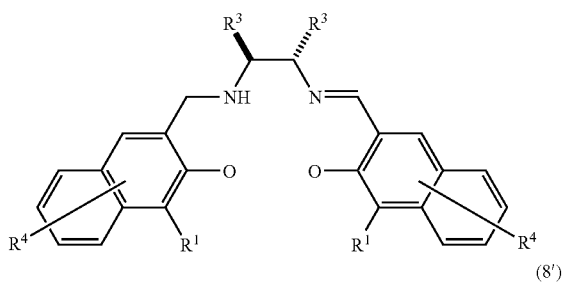

(8)

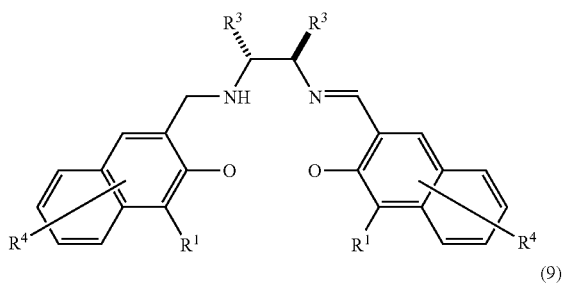

(8')

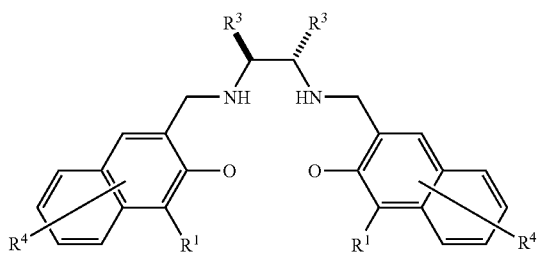

(9)

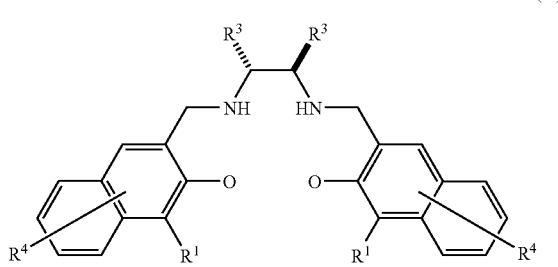

(9')

b represents an integer of 1 to 10; and $R^1$, $R^2$, $R^3$ and $R^4$ are the same as described above));

according to a second aspect, the process for producing an optically active chromene oxide compound according to the first aspect, in which the chromene compound represented by the formula (10) is asymmetrically epoxidized in a solvent with oxidizing reagent by using an optically active titanium complex represented by any of the formula (1), formula (1'), formula (2), formula (2'), formula (3), formula (3'), formula (4) and formula (4') as a catalyst;

in which $R^5$ and $R^6$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom), $C_{1-4}$ alkylcarbonyl(N—$C_{1-4}$ alkyl)amino group (the alkylcarbonyl(N-alkyl)amino group may be optionally substituted with a halogen atom), $C_{6-10}$ arylcarbonyl(N—$C_{1-4}$ alkyl)amino group (the arylcarbonyl(N-alkyl)amino group may be substituted with a halogen atom, $C_{1-4}$ alkyl group, $C_{1-4}$ alkoxy group, cyano group or nitro group), carbamoyl group, bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis($C_{6-10}$ arylsulfone) imide group (arylsulfone of the bis(arylsulfone)imide group may be substituted with a halogen atom, $C_{1-4}$ alkyl group, $C_{1-4}$ alkoxy group, cyano group or nitro group), or (N,N'—($C_{1-4}$alkylsulfone) ($C_{6-10}$ arylsulfone))imide group (alkylsulfone and arylsulfone of the (N,N'-(alkylsulfone) (arylsulfone))imide group may be substituted with a halogen atom, $C_{1-4}$ alkyl group, $C_{1-4}$ alkoxy group, cyano group or nitro group);

$R^7$ in the formula (10) represents a hydrogen atom, cyano group, nitro group, bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis($C_{6-10}$ arylsulfone) imide group (arylsulfone of the bis (arylsulfone)imide group may be substituted with a halogen atom, $C_{1-4}$ alkyl group, $C_{1-4}$ alkoxy group, cyano group or nitro group), or (N,N'—($C_{1-4}$ alkylsulfone)($C_{6-10}$ arylsulfone))imide group (alkylsulfone and arylsulfone of the (N,N'-(alkylsulfone)(arylsulfone))imide group may be substituted with a halogen atom, $C_{1-4}$ alkyl group, $C_{1-4}$ alkoxy group, cyano group or nitro group);

$R^8$ in the formula (10) represents a hydrogen atom, nitro group, or $C_{1-4}$ alkyl group (the alkyl group may be optionally substituted with a halogen atom); and $R^9$ and $R^{10}$ in the formula (10) represent a $C_{1-6}$ alkyl group (the alkyl group may be optionally substituted with a halogen atom); according to a third aspect, the process for producing an optically active chromene oxide compound according to the second aspect, in which $R^5$ and $R^6$ in the formula (10) each independently represent a hydrogen atom, nitro group, fluorine atom, methoxy group, methylcarbonylamino group or methylcarbonyl(N-ethyl)amino group; $R^7$ in the formula (10) represents a hydrogen atom, nitro group or bis($C_{1-4}$ alkylsulfone)imide group; $R^8$ in the formula (10) represents a hydrogen atom, nitro group or trifluoromethyl group; and $R^9$ and $R^{10}$ in the formula (10) represent a methyl group;

according to a fourth aspect, the process for producing an optically active chromene oxide compound according to the first aspect, in which the chromene compound represented by the formula (11) or (12) whose partial ring structure A is represented by any of the formula (a), formula (b), formula (c), formula (d), formula (e), formula (f), formula (g), formula (h), formula (i), formula (j), formula (k), formula (l), formula (m), formula (n), formula (o), formula (p), formula (q), formula (r), formula (s), formula (t), formula (u), formula (v), formula (w), formula (x), formula (y), formula (z), formula (aa), formula (ab), formula (ac), formula (ad), formula (ae), formula (af), formula (ag), and formula (ah) is asymmetrically epoxidized in a solvent with oxidizing reagent by using any of the optically active titanium complexes represented by the formula (1), formula (1'), formula (2), formula (2'), formula (3), formula (3'), formula (4) and formula (4') as a catalyst,

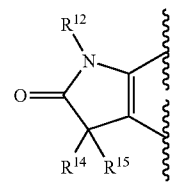
(a)

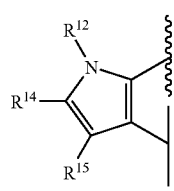
(b)

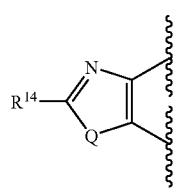
(c)

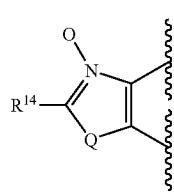
(d)

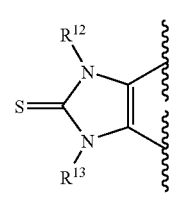
(e)

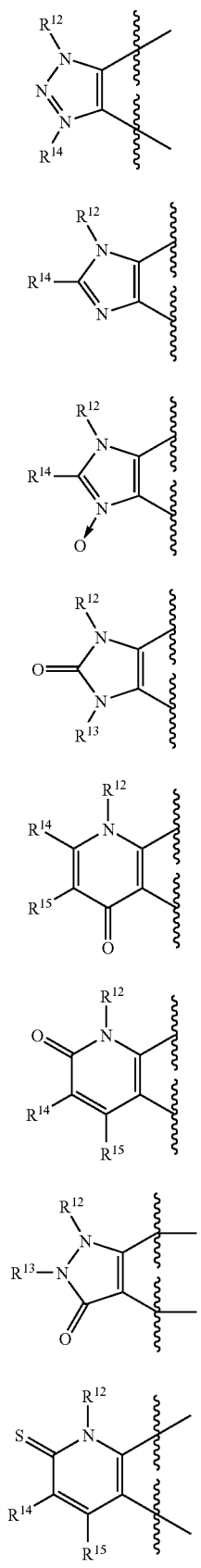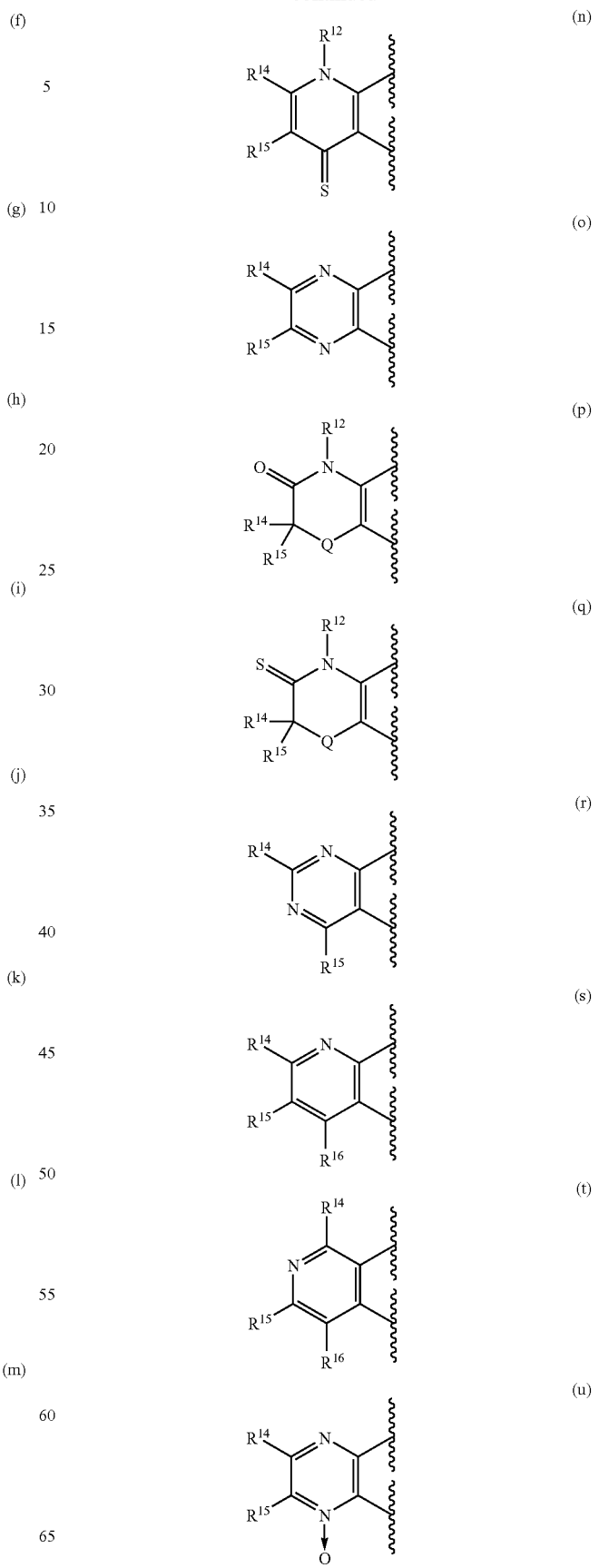

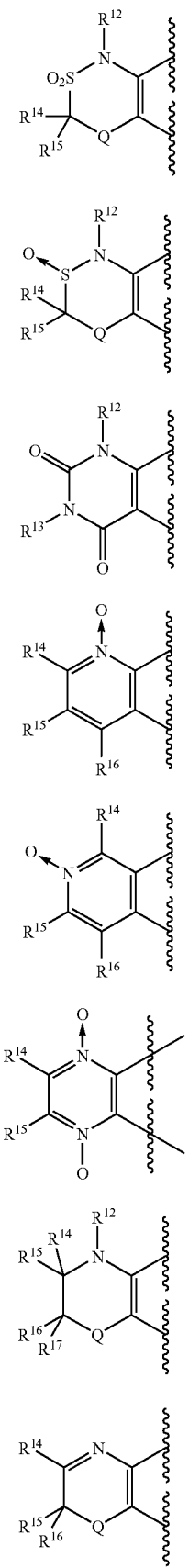
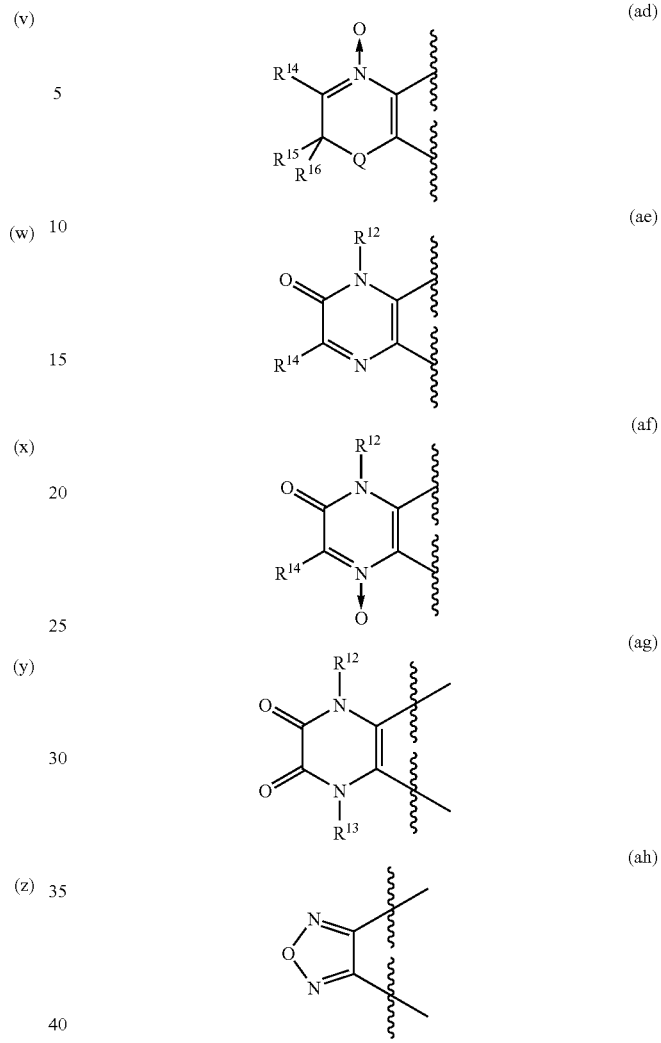

(in which $R^{12}$ and $R^{13}$ in the formula (a), formula (b), formula (e), formula (f), formula (g), formula (h), formula (i), formula (o), formula (k), formula (l), formula (m), formula (n), formula (p), formula (q), formula (v), formula (w), formula (x), formula (ab), formula (ae), formula (af) and formula (ag) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group or $C_{2-9}$ heteroaryl group (each of the aryl group and heteroaryl group may be optionally substituted with q $R^{18}$ ($R^8$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom) or $C_{2-9}$ heteroarylcarbonyl group), $C_{6-14}$ aryl group, $C_{2-9}$ heteroaryl group (each of the aryl group and heteroaryl group may be optionally substituted with q $R^{18}$ ($R^{18}$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, $C_{6-14}$ arylsulfonyl group, $C_{2-9}$ heteroarylsulfonyl group (each of the arylsulfonyl group and heteroarylsulfonyl group may be optionally substituted with q $R^{18}$ ($R^{18}$ represents the same meaning of $R^{11}$; q represents an integer of 1 to 3, and each $R^{18}$ may be the same or different when q is 2 or 3)), carboxyl group, $C_{6-14}$ arylcarbonyl group, or $C_{2-9}$ heteroarylcarbonyl group (each of the arylcarbonyl group and heteroarylcarbonyl group may be optionally substituted with q $R^{18}$ ($R^{18}$ represents the same meaning of $R^{11}$; q represents an integer of 1 to 3, and each $R^{18}$ may be the same or different when q is 2 or 3));

$R^{14}$, $R^{15}$, $R^{16}$ and $R^{17}$ in the formula (a), formula (b), formula (c), formula (d), formula (f), formula (g), formula (h), formula (j), formula (k), formula (m), formula (n), formula (o), formula (p), formula (q), formula (r), formula (s), formula (t), formula (u), formula (v), formula (w), formula (y), formula (z), formula (aa), formula (ab), formula (ac), formula (ad), formula (ae) and formula (af) each independently represent a hydrogen atom, halogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom), or $C_{2-9}$ heteroarylcarbonyl group), $C_{3-8}$ cycloalkyl group (the cycloalkyl group may be optionally substituted with a halogen atom, $C_{1-6}$ alkoxy group (the alkoxy group may be optionally substituted with a halogen atom), amino group or hydroxy group), $C_{1-6}$ alkoxy group (the alkoxy group may be optionally substituted with a halogen atom, $C_{1-6}$ alkoxy group (the alkoxy group may be optionally substituted with a halogen atom), carboxyl group, amino group, hydroxy group, $C_{6-14}$ aryl group or $C_{2-9}$ heteroaryl group (each of the aryl group and heteroaryl group may be optionally substituted with r $R^{19}$ ($R^{19}$ represents the same meaning of $R^{11}$; r represents the same meaning of q))), $C_{1-6}$ thioalkoxy group (the thioalkoxy group may be optionally substituted with a halogen atom, $C_{1-6}$ alkoxy group (the alkoxy group may be optionally substituted with a halogen atom), carboxyl group, hydroxy group, $C_{6-14}$ aryl group or $C_{2-9}$ heteroaryl group (each of the aryl group and heteroaryl group may be optionally substituted with r $R^{19}$ ($R^{19}$ represents the same meaning of $R^{11}$; r represents the same meaning of q))), hydroxy group, $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), $C_{1-6}$ alkylcarbonyloxy group, nitro group, cyano group, formyl group, formamide group, amino group, sulfo group, $C_{1-6}$ alkylamino group, di-$C_{1-6}$ alkylamino group, $C_{6-14}$ arylamino group, $C_{2-9}$ heteroarylamino group (each of the arylamino group and the heteroarylamino group may be optionally substituted with r $R^{19}$ ($R^{19}$ represents the same meaning of $R^{11}$; r represents the same meaning of q)), $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{6-14}$ arylcarbonyl group, $C_{2-9}$ heteroarylcarbonyl group (each of the arylcarbonyl group and heteroarylcarbonyl group may be optionally substituted with r $R^{19}$ ($R^{19}$ represents the same meaning of $R^{11}$; r represents the same meaning of q)), $C_{1-6}$ alkoxycarbonyl group, sulfamoyl group, $C_{1-6}$ alkylsulfonyl group, $C_{6-14}$ arylsulfonyl group, $C_{2-9}$ heteroarylsulfonyl group (each of the arylsulfonyl group and heteroarylsulfonyl group may be optionally substituted with r $R^{19}$ ($R^{19}$ represents the same meaning of $R^{11}$; r represents the same meaning of q)), carboxyl group or $C_{2-9}$ heterocyclyl group (the heterocyclyl group may be optionally substituted with a halogen atom, $C_{1-6}$ alkyl group (the alkyl group may be optionally substituted with a halogen atom, $C_{1-6}$ alkoxy group (the alkoxy group may be optionally substituted with a halogen atom), amino group, carboxyl group or hydroxy group), $C_{1-6}$ alkoxy group (the alkoxy group may be optionally substituted with a halogen atom), $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, sulfamoyl group, $C_{1-6}$ alkylsulfonyl group, carboxyl group or $C_{6-14}$ arylcarbonyl group); and Q in the formula (c), formula (d), formula (p), formula (q), formula (v), formula (w), formula (ab), formula (ac) and formula (ad) represents O (oxygen atom), S (sulfur atom), SO (sulfinyl group) or $SO_2$ (sulfonyl group));

according to a fifth aspect, the process for producing an optically active chromene oxide compound according to the fourth aspect, in which $R^9$ and $R^{10}$ in the formula (11) or the formula (12) are methyl group;

according to a sixth aspect, the process for producing an optically active chromene oxide compound according to the fourth or fifth aspect, in which A in the formula (11) or the formula (12) is represented by the following formula (a), formula (b), formula (i), formula (k), formula (o), formula (p), formula (s), formula (v), formula (y), formula (ae), formula (ag) and formula (ah),

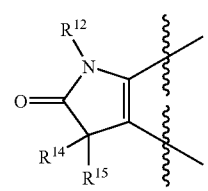

(a)

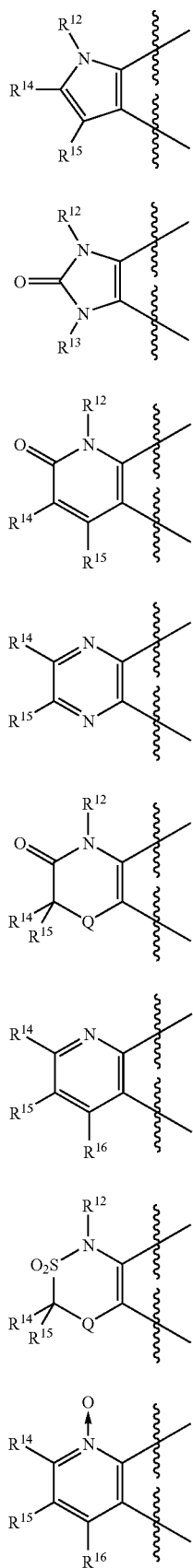

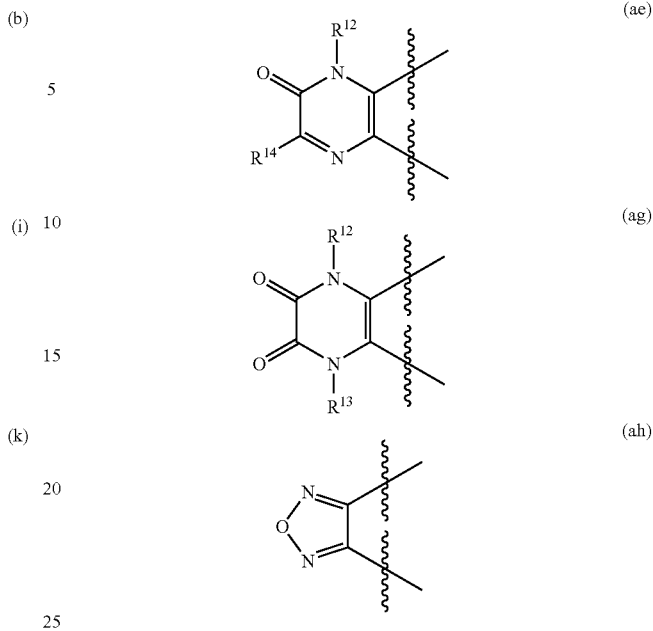

(in which $R^{12}$, $R^{13}$, $R^{14}$, $R^{15}$ and $R^{16}$ are the same as in the fourth aspect);

according to a seventh aspect, the process for producing an optically active chromene oxide compound according to the sixth aspect, in which A in the formula (11) or the formula (12) represents the formula (a), formula (b), formula (1), formula (k), formula (o), formula (p), formula (s), formula (v), formula (y), formula (ae), formula (ag) and formula (ah); $R^{12}$ and $R^{13}$ in the formula (a), formula (b), formula (i), formula (k), formula (p), formula (v), formula (ae) and formula (ag) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group or hydroxy group), and $R^{14}$, $R^{15}$ and $R^{16}$ in the formula (a), formula (b), formula (k), formula (o), formula (p), formula (s), formula (v), formula (y) and formula (ae) each independently represent a hydrogen atom, halogen atom or $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group or $C_{1-6}$ alkoxycarbonyl group); and Q represents O (oxygen atom);

according to an eighth aspect, the process for producing an optically active chromene oxide compound according to the seventh aspect, in which A in the formula (11) or the formula (12) represents the formula (a), formula (b), formula (1), formula (k), formula (o), formula (p), formula (s), formula (v), formula (y), formula (ae), formula (ag) or formula (ah), and $R^{12}$ and $R^{13}$ in the formula (a), formula (b), formula (i), formula (k), formula (p), formula (v), formula (ae) and formula (ag) each independently represent a hydrogen atom or methyl group, and $R^{14}$, $R^{15}$ and $R^{16}$ in the formula (a), formula (b), formula (k), formula (o), formula (p), formula (s), formula (v), formula (y) and formula (ae) each independently represent a hydrogen atom, halogen atom or $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group or $C_{1-6}$ alkoxycarbonyl group); and Q represents O (oxygen atom);

according to a ninth aspect, the process for producing an optically active chromene oxide compound according to the first aspect, in which the chromene compound represented by the formula (13) is asymmetrically epoxidized in a solvent with oxidizing reagent by using an optically active titanium complex represented by any of formula (1), formula (1'), formula (2), formula (2'), formula (3), formula (3'), formula (4) and formula (4') as a catalyst, and both $R^9$ and $R^{10}$ in the formula (13) represent a methyl group;

according to a tenth aspect, the process for producing an optically active chromene oxide compound according to the ninth aspect, in which W in the formula (13) represents a hydrogen atom, hydroxy group, methoxy group, chlorine atom, bromine atom, methyl group, ethyl group or methanesulfonamide group;

according to an eleventh aspect, the process for producing an optically active chromene oxide compound according to the ninth or tenth aspect, in which Y in the formula (13) represents $SO_2$ (sulfonyl group) and Z represents $C_{1-4}$ alkyl group;

according to a twelfth aspect, the process for producing an optically active chromene oxide compound according to the tenth aspect, in which Y in the formula (13) represents a bond and Z represents a $C_{1-4}$ alkyl group;

according to a thirteenth aspect, the process for producing an optically active chromene oxide compound according to the first aspect, in which $R^1$ in the formula (1), formula (1'), formula (2), formula (2'), formula (3), formula (3'), formula (4) and formula (4') represents a $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group and is optically active or optically non-active);

$R^2$ represents a hydrogen atom, halogen atom, $C_{1-4}$ alkyl group, $C_{1-4}$ alkoxy group, $C_{6-12}$ aryloxy group or $C_{6-18}$ aryl group;

$R^3$ represents a $C_{1-4}$ alkyl group, $C_{6-18}$ aryl group or $C_{3-5}$ bivalent group when two $R^3$ form a ring together;

$R^4$ each independently represents a hydrogen atom, halogen atom, $C_{1-4}$ alkyl group, $C_{1-4}$ alkoxy group, nitro group or cyano group; and M represents $TiJ^1J^2$, (in which Ti is titanium atom; $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group, (in which, in partial structure of O-E-O, O represents an oxygen atom and O-E-O is represented by the formula (6) in formula (1); O-E-O is represented by the formula (6') in formula (1'); O-E-O is represented by the formula (7) in formula (2); O-E-O is represented by the formula (7') in formula (2'); O-E-O is represented by the formula (8) in formula (3); O-E-O is represented by the formula (8') in formula (3'); O-E-O is represented by the formula (9) in formula (4); O-E-O is represented by the formula (9') in formula (4'); b represents an integer of 1 to 10; and $R^1$, $R^2$, $R^3$ and $R^4$ are the same as described above));

according to a fourteenth aspect, the process for producing an optically active chromene oxide compound according to the thirteenth aspect, in which $R^1$ in the formula (1), formula (1'), formula (2), formula (2'), formula (3), formula (3'), formula (4) and formula (4') is phenyl group (the phenyl group may be optionally substituted with a $C_{1-4}$ alkyl group (the alkyl group may be optionally substituted with a halogen atom), benzyloxy group or $C_{1-7}$ alkoxy group), or naphthyl group (the naphthyl group may be optionally substituted with a $C_{1-4}$ alkyl group (the alkyl group may be optionally substituted with a halogen atom), $C_{1-7}$ alkoxy group or phenyl group);

$R^2$ represents a hydrogen atom;

$R^3$ represents a $C_{3-5}$ bivalent group when two $R^3$ form a ring together;

$R^4$ represents a hydrogen atom; and

M represents $TiJ^1J^2$, (in which Ti is titanium atom; $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group, (in which, in partial structure of O-E-O, O represents an oxygen atom and O-E-O is represented by the formula (6) in formula (1); O-E-O is represented by the formula (6') in formula (1'); O-E-O is represented by the formula (7) in formula (2); O-E-O is represented by the formula (7') in formula (2'); O-E-O is represented by the formula (8) in formula (3); O-E-O is represented by the formula (8') in formula (3'); O-E-O is represented by the formula (9) in formula (4); O-E-O is represented by the formula (9') in formula (4'); b represents an integer of 1 to 10; and $R^1$, $R^2$, $R^3$ and $R^4$ are the same as described above));

according to a fifteenth aspect, the process for producing an optically active chromene oxide compound according to any one of the first to fourteenth aspects, in which a used amount of the optically active titanium complex to an amount of chromene compound represented by the formula (10), formula (11), formula (12) or formula (13) is 0.001 to 100 mol %;

according to a sixteenth aspect, the process for producing an optically active chromene oxide compound according to any one of the first to fourteenth aspects, in which the solvent used for the asymmetric epoxidation is a halogen-type solvent, an aromatic hydrocarbon-type solvent, an ester-type solvent, an ether-type solvent, a nitrile-type solvent, an alcohol-type solvent or a mixture thereof;

according to a seventeenth aspect, the process for producing an optically active chromene oxide compound according to any one of the first to fourteenth aspects, in which the oxidizing reagent used for the asymmetric epoxidization reaction is iodosobenzene, sodium hypochlorite, m-chloroperbenzoic acid, Oxone (registered trademark of E. I. du Pont de Nemours and Company), hydrogen peroxide aqueous solution, urea-hydrogen peroxide adduct (UHP), oxaziridine, N-methylmorpholineoxide (NMO), t-butylhydroperoxide (TBHP), cumenehydroperoxide (CHP) or a mixture thereof;

according to an eighteenth aspect, the process for producing an optically active chromene oxide compound according to the seventeenth aspect, in which the oxidizing reagent used for the asymmetric epoxidization reaction is hydrogen peroxide aqueous solution, urea-hydrogen peroxide adduct (UHP) or mixture thereof;

according to a nineteenth aspect, the process for producing an optically active chromene oxide compound according to the eighteenth aspect, in which the oxidizing reagent used for the asymmetric epoxidation is hydrogen peroxide aqueous solution and a concentration thereof is 1 to 100% by mass;

according to a twentieth aspect, the process for producing an optically active chromene oxide compound according to any one of the first to fourteenth aspects, in which a used amount of the oxidizing reagent used for the asymmetric epoxidation to an amount of chromene compound represented by the formula (10), formula (11), formula (12) or formula (13) is 1 to 10 equivalent;

according to a twenty-first aspect, the process for producing an optically active chromene oxide compound according to the twentieth aspect, in which an addition method of the oxidizing reagent used for the asymmetric epoxidation is fractionated addition or continuous addition;

according to a twenty-second aspect, the process for producing an optically active chromene oxide compound according to the twenty-first aspect, in which the addition method of the oxidizing reagent used for the asymmetric epoxidation is the continuous addition and the addition rate is 0.01 to 40,000 equivalent per hour;

according to a twenty-third aspect, the process for producing an optically active chromene oxide compound according to the twenty-first aspect, in which the addition method of the oxidizing reagent used for the asymmetric epoxidation is fractionated addition and the number of fractions is in a range of 2 to 100;

according to a twenty-fourth aspect, the process for producing an optically active chromene oxide compound according to any one of the first to twenty-third aspects, in which a reaction temperature of the asymmetric epoxidation is from 0° C. to a reflux temperature of the solvent used; and according to a twenty-fifth aspect, the process for producing an optically active chromene oxide compound according to any one of the first to twenty-fourth aspects, in which a pressure of the asymmetric epoxidation in a reacting system is in a range of 10 kPa to 1,100 kPa.

Effects of the Invention

According to the present invention, an optically active chromene oxide compound which is an important intermediate for a benzopyran compound being effective in the treatment of arrhythmia can be efficiently produced.

BEST MODES FOR CARRYING OUT THE INVENTION

As used herein, "n" means normal; "i" means iso; "s" means secondary; "t" means tertiary; "c" means cyclo; "o" means ortho; "m" means meta and "p" means para.

The present invention will be described below in detail. In the present invention, a titanium complex used for an asymmetric epoxidation of a chromene compound with an oxidizing reagent is represented by the following formula (1), formula (1'), formula (2), formula (2'), formula (3), formula (3'), formula (4) and formula (4'):

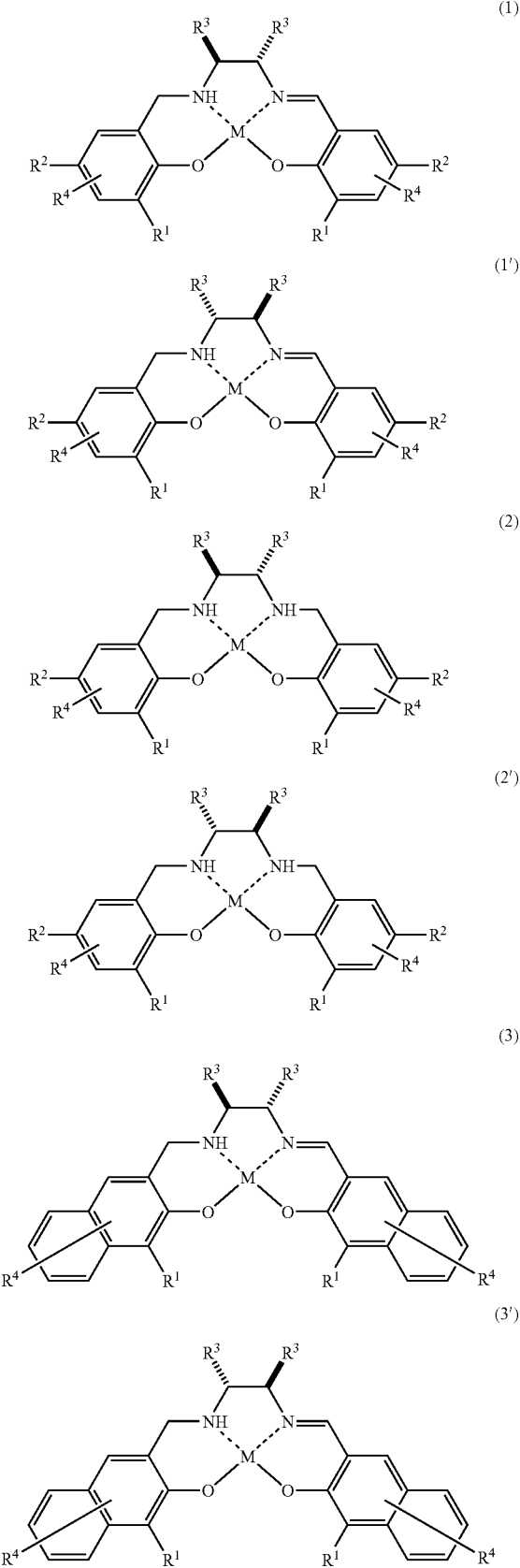

(4)

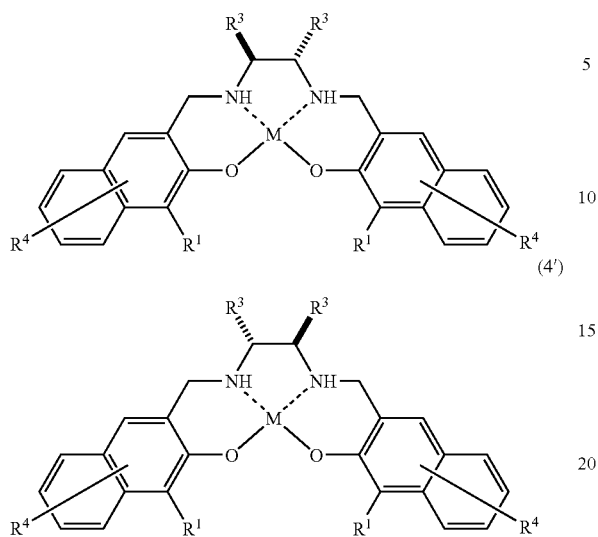

(4')

in which R¹ in the formula (1), formula (1'), formula (2), formula (2'), formula (3), formula (3'), formula (4) or formula (4') represents a hydrogen atom, halogen atom, $C_{1-4}$ alkyl group, $C_{1-4}$ alkoxy group, $C_{6-12}$ aryloxy group, or $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group), and is optically active or optically non-active;

R² represents a hydrogen atom, halogen atom, $C_{1-4}$ alkyl group, $C_{1-4}$ alkoxy group, $C_{6-12}$ aryloxy group or $C_{6-18}$ aryl group;

R³ represents a $C_{1-4}$ alkyl group, $C_{6-18}$ aryl group or $C_{3-5}$ bivalent group when two R³ form a ring together;

R⁴ each independently represents a hydrogen atom, halogen atom, $C_{1-4}$ alkyl group, $C_{1-4}$ alkoxy group, nitro group or cyano group;

M represents $TiJ^1J^2$ (in $TiJ^1J^2$, Ti represents titanium, and $J^1$ and $J^2$ each independently represent a halogen atom or $C_{1-4}$ alkoxide group, or $J^1$ and $J^2$ are bonded together to represent an oxygen atom, or $J^1$ and $J^2$ are bonded together to form a ring represented by the formula (5) of bivalent group, (5)

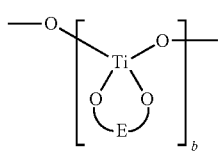

in which, in partial structure of O-E-O, O represents an oxygen atom and O-E-O is represented by following formula (6) in formula (1); O-E-O is represented by following formula (6') in formula (1'); O-E-O is represented by following formula (7) in formula (2); O-E-O is represented by following formula (7') in formula (2'); O-E-O is represented by following formula (8) in formula (3); O-E-O is represented by following formula (8') in formula (3'); O-E-O is represented by following formula (9) in formula (4); O-E-O is represented by following formula (9') in formula (4'); and (6)

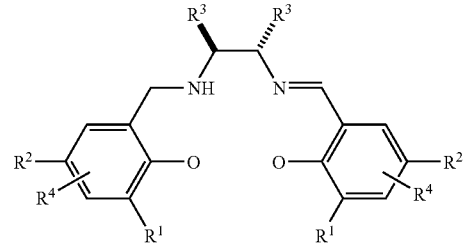

(6')

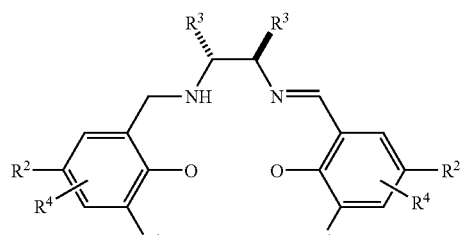

(7)

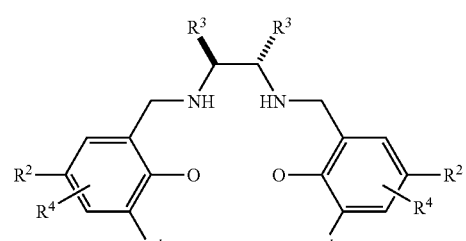

(7')

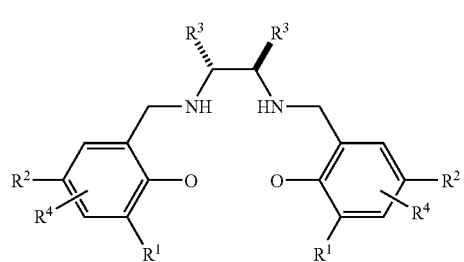

(8)

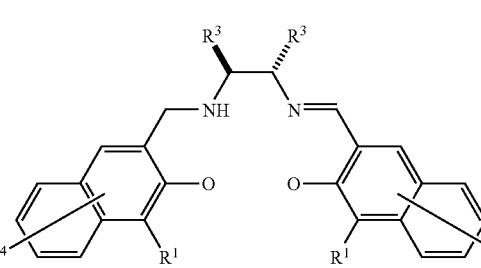

(8')

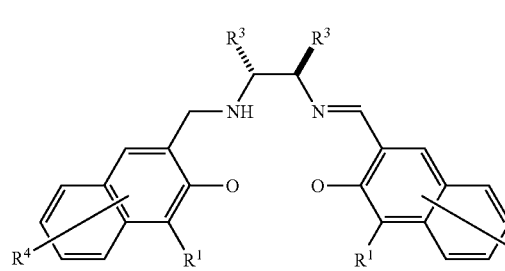

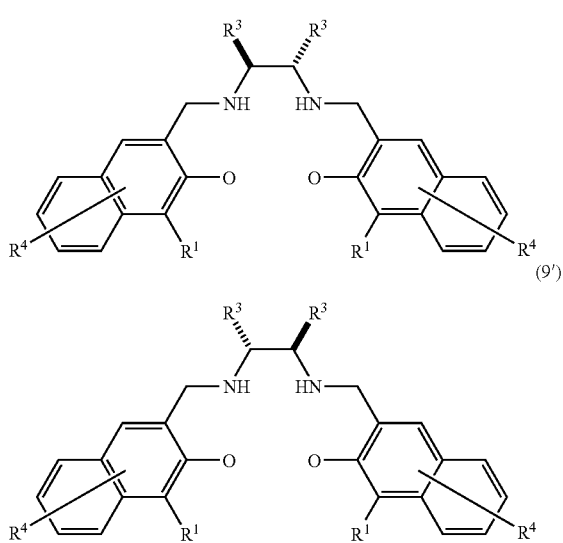

b represents an integer of 1 to 10; and $R^1$, $R^2$, $R^3$ and $R^4$ are the same as described above.

Each substituted group in the formula (1), formula (1'), formula (2), formula (2'), formula (3), formula (3'), formula (4) and formula (4') will be described below.

$R^1$ in the formula (1), formula (1'), formula (2), formula (2'), formula (3), formula (3'), formula (4) and formula (4') is hydrogen atom, halogen atom, $C_{1-4}$ alkyl group, $C_{1-4}$ alkoxy group, $C_{6-12}$ aryloxy group or $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group, and is optically active or optically non-active).

$R^1$ in the above-mentioned formula (1), formula (1'), formula (2), formula (2'), formula (3), formula (3'), formula (4) and formula (4') will be specifically described.

Examples of the halogen atom include a fluorine atom, chlorine atom, bromine atom and iodine atom;

examples of the $C_{1-4}$ alkyl group include a methyl group, ethyl group, n-propyl group, i-propyl group, n-butyl group, i-butyl group, s-butyl group and t-butyl group;

examples of the $C_{1-4}$ alkoxy group include a methoxy group, ethoxy group, n-propoxy group, i-propoxy group, c-propoxy group, n-butoxy group, i-butoxy group, s-butoxy group, t-butoxy group and c-butoxy group;

examples of the $C_{6-12}$ aryloxy group include a phenyloxy group, 1-naphthyloxy group, 2-naphthyloxy group, 2-biphenylyloxy group, 3-biphenylyloxy group and 4-biphenylyloxy group; and examples of the $C_{6-22}$ aryl group (the aryl group may be optionally substituted with a $C_{1-4}$ alkyl group (the alkyl group may be optionally substituted with a halogen atom), $C_{1-7}$ alkoxy group, or benzyloxy group, and is optically active or optically non-active) include a phenyl group, 2-methylphenyl group, 2-trifluoromethylphenyl group, 4-methylphenyl group, 2-ethylphenyl group, 2-pentafluoroethylphenyl group, 3,5-dimethylphenyl group, 2-methoxyphenyl group, 3-methoxyphenyl group, 4-methoxyphenyl group, 2-ethoxyphenyl group, 2-i-propoxyphenyl group, 2-benzyloxyphenyl group, 3,5-dimethoxyphenyl group, 1-naphthyl group, 2-naphthyl group, 2-biphenylyl group, 3-biphenylyl group, 4-biphenylyl group, 2-methyl-1-naphthyl group, 2-phenyl-1-naphthyl group, 2-methoxy-1-naphthyl group, 2-(3,5-dimethylphenyl)-1-naphthyl group, 2-(4-methylphenyl)-1-naphthyl group, 2-(o-biphenylyl)-1-naphthyl group, 2-(m-biphenylyl)-1-naphthyl group and 2-(p-biphenylyl)-1-naphthyl group. The above-mentioned $C_{6-22}$ aryl group may be optically active or optically non-active.

$R^1$ in the formula (1), formula (1'), formula (2), formula (2'), formula (3), formula (3'), formula (4) and formula (4') is preferably hydrogen atom, fluorine atom, chlorine atom, bromine atom, iodine atom, methyl group, ethyl group, n-propyl group, i-propyl group, n-butyl group, i-butyl group, s-butyl group, t-butyl group, methoxy group, ethoxy group, n-propoxy group, i-propoxy group, c-propoxy group, n-butoxy group, i-butoxy group, s-butoxy group, t-butoxy group, c-butoxy group, phenyloxy group, 1-naphthyloxy group, 2-naphthyloxy group, phenyl group, 2-methylphenyl group, 2-trifluoromethylphenyl group, 4-methylphenyl group, 2-ethylphenyl group, 3,5-dimethylphenyl group, 2-methoxyphenyl group, 3-methoxyphenyl group, 4-methoxyphenyl group, 2-ethoxyphenyl group, 2-i-propoxyphenyl group, 2-benzyloxyphenyl group, 3,5-dimethoxyphenyl group, 1-naphthyl group, 2-naphthyl group, 2-biphenylyl group, 3-biphenylyl group, 4-biphenylyl group, 2-phenyl-1-naphthyl group, 2-methoxy-1-naphthyl group, 2-(m-biphenylyl)-1-naphthyl group and 2-(p-biphenylyl)-1-naphthyl group. Of these atoms and groups, phenyl group, 2-methylphenyl group, 2-trifluoromethylphenyl group, 2-ethylphenyl group, 2-methoxyphenyl group, 2-benzyloxyphenyl group, 1-naphthyl group, 2-naphthyl group, 2-biphenylyl group, 2-phenyl-1-naphthyl group, 2-methoxy-1-naphthyl group, 2-(m-biphenylyl)-1-naphthyl group and 2-(p-biphenylyl)-1-naphthyl group (the 2-phenyl-1-naphthyl group, 2-methoxy-1-naphthyl group, 2-(m-biphenylyl)-1-naphthyl group or 2-(p-biphenylyl)-1-naphthyl group are optically active or optically non-active) are more preferable for $R^1$, and among these atoms and groups, phenyl group, 2-methylphenyl group, 2-trifluoromethylphenyl group, 2-methoxyphenyl group, 2-benzyloxyphenyl group and 2-phenyl-1-naphthyl group are much more preferable for $R^1$.

$R^2$ in the formula (1), formula (1'), formula (2), formula (2'), formula (3), formula (3'), formula (4) and formula (4') represents a hydrogen atom, halogen atom, $C_{1-4}$ alkyl group, $C_{1-4}$ alkoxy group, $C_{6-12}$ aryloxy group or $C_{6-18}$ aryl group.

$R^2$ in the formula (1), formula (1'), formula (2), formula (2'), formula (3), formula (3'), formula (4) and formula (4') will be specifically described.

Examples of the halogen atom include a fluorine atom, chlorine atom, bromine atom and iodine atom;

examples of the $C_{1-4}$ alkyl group include a methyl group, ethyl group, n-propyl group, i-propyl group, n-butyl group, i-butyl group, s-butyl group and t-butyl group;

examples of the $C_{1-4}$ alkoxy group include a methoxy group, ethoxy group, n-propoxy group, i-propoxy group, c-propoxy group, n-butoxy group, i-butoxy group, s-butoxy group, t-butoxy group and c-butoxy group;

examples of the $C_{6-12}$ aryloxy group include a phenyloxy group, 1-naphthyloxy group, 2-naphthyloxy group, 2-biphenylyloxy group, 3-biphenylyloxy group and 4-biphenylyloxy group; and examples of the $C_{6-18}$ aryl group include a phenyl group, 3,5-dimethylphenyl group, 4-methylphenyl group, 1-naphthyl group, 2-naphthyl group, 2-biphenylyl group, 2-phenyl-1-naphthyl group, 2-methyl-1-naphthyl group, 2-(3,5-dimethylphenyl)-1-naphthyl group, 2-(4-methylphenyl)-1-naphthyl group and 2-methoxy-1-naphthyl group.

$R^2$ in the formula (1), formula (1'), formula (2), formula (2'), formula (3), formula (3'), formula (4) and formula (4') is preferably hydrogen atom, fluorine atom, chlorine atom, bromine atom, iodine atom, methyl group, ethyl group, n-propyl group, i-propyl group, n-butyl group, t-butyl group, methoxy group, phenyloxy group, 1-naphthyloxy group, 2-naphthyloxy group, phenyl group, 3,5-dimethylphenyl group, 4-methylphenyl group, 3,5-dimethoxyphenyl group, 4-methoxyphenyl group, 1-naphthyl group, 2-naphthyl group, 2-biphenylyl group, 3-biphenylyl group, 4-biphenylyl group and 2-methoxy-1-naphthyl group. Of these atoms and groups, hydrogen atom, fluorine atom, chlorine atom, bromine atom, iodine atom, methyl group, ethyl group, n-propyl group, i-propyl group, n-butyl group, t-butyl group, methoxy group, phenyloxy group, phenyl group, 1-naphthyl group, 2-naphthyl group and 2-biphenylyl group are more preferable for $R^2$ and among these atoms and groups, hydrogen atom is much more preferable for $R^2$.

$R^3$ in the formula (1), formula (1'), formula (2), formula (2'), formula (3), formula (3'), formula (4) and formula (4') represents a $C_{1-4}$ alkyl group, $C_{6-18}$ aryl group, or $C_{3-5}$ bivalent group when two $R^3$ form a ring together.

$R^3$ in the formula (1), formula (1'), formula (2), formula (2'), formula (3), formula (3'), formula (4) and formula (4') will be specifically described.

Examples of the $C_{1-4}$ alkyl include a methyl group, ethyl group, n-propyl group, i-propyl group, n-butyl group, i-butyl group, s-butyl group and t-butyl group;

examples of the $C_{6-18}$ aryl group include a phenyl group, 3,5-dimethylphenyl group, 2,4,6-trimethylphenyl group, 4-methylphenyl group, 1-naphthyl group, 2-biphenylyl group, 2-phenyl-1-naphthyl group, 2-methyl-1-naphthyl group, 2-(3,5-dimethylphenyl)-1-naphthyl group, 2-(4-methylphenyl)-1-naphthyl group, and 2-methoxy-1-naphthyl group; and when two $R^3$ form a ring together, they are a $C_{3-5}$ bivalent group and examples of the bivalent group include a trimethylene group and tetramethylene group.

$R^3$ in the formula (1), formula (1'), formula (2), formula (2'), formula (3), formula (3'), formula (4) and formula (4') is preferably phenyl group, 3,5-dimethylphenyl group, 2,4,6-trimethylphenyl group, 4-methylphenyl group and tetramethylene group formed by bonding two $R^3$, and among these groups, tetramethylene group formed by bonding two $R^3$ each other is more preferable for $R^3$.

$R^4$ in the formula (1), formula (1'), formula (2), formula (2'), formula (3), formula (3'), formula (4) and formula (4') is hydrogen atom, halogen atom, $C_{1-4}$ alkyl group, $C_{1-4}$ alkoxy group, nitro group or cyano group.

$R^4$ in the formula (1), formula (1'), formula (2), formula (2'), formula (3), formula (3'), formula (4) and formula (4') will be specifically described.

Examples of the halogen atom include a fluorine atom, chlorine atom, bromine atom and iodine atom; and examples of the $C_{1-4}$ alkyl group include a methyl group, ethyl group, n-propyl group, i-propyl group, n-butyl group, i-butyl group, s-butyl group and t-butyl group; and examples of the $C_{1-4}$ alkoxy group include a methoxy group, ethoxy group, n-propoxy group, i-propoxy group, n-butoxy group, i-butoxy group, s-butoxy group and t-butoxy group.

$R^4$ in the formula (1), formula (1'), formula (2), formula (2'), formula (3), formula (3'), formula (4) and formula (4') is preferably hydrogen atom, fluorine atom, chlorine atom, bromine atom, methyl group, ethyl group, n-propyl group, i-propyl group, n-butyl group, i-butyl group, s-butyl group, t-butyl group, methoxy group, ethoxy group, n-propoxy group, i-propoxy group, n-butoxy group, i-butoxy group, s-butoxy group and t-butoxy group. Of these atoms and groups, hydrogen atom is more preferable for $R^4$.

M in the formula (1), formula (1'), formula (2), formula (2'), formula (3), formula (3'), formula (4) and formula (4') represents $TiJ^1J^2$ (in $TiJ^1J^2$, Ti represents a titanium atom, and $J^1$ and $J^2$ each independently represent a halogen atom or $C_{1-4}$ alkoxide group, or $J^1$ and $J^2$ are bonded together to represent an oxygen atom, or $J^1$ and $J^2$ are bonded together to form a ring represented by the formula (5) of bivalent group,

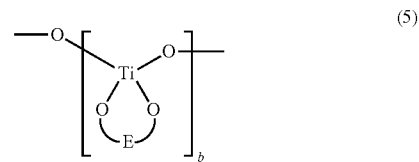

in which, in partial structure of O-E-O, O represents an oxygen atom and O-E-O is represented by following formula (6) in formula (1); O-E-O is represented by following formula (6') in formula (1'); O-E-O is represented by following formula (7) in formula (2); O-E-O is represented by following formula (7') in formula (2'); O-E-O is represented by following formula (8) in formula (3); O-E-O is represented by following formula (8') in formula (3'); O-E-O is represented by following formula (9) in formula (4); O-E-O is represented by following formula (9') in formula (4'); and

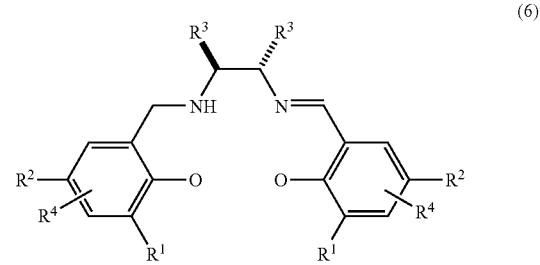

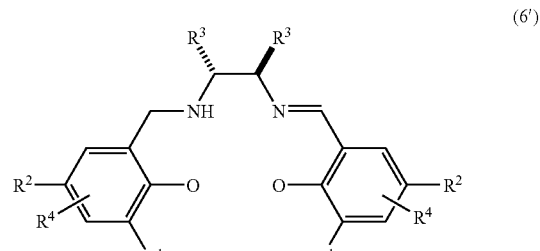

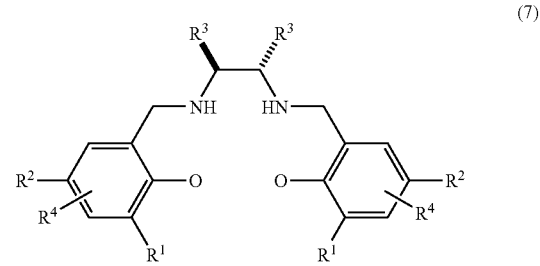

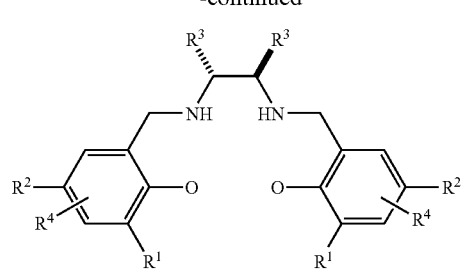
(7')

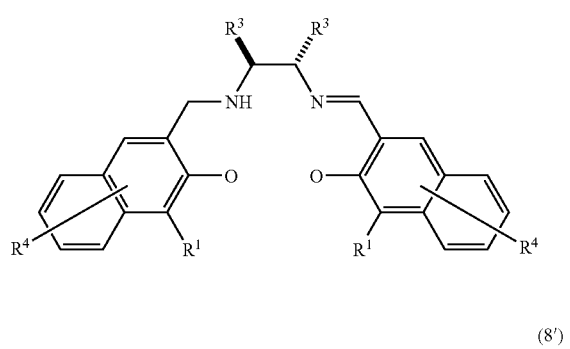
(8)

(8')

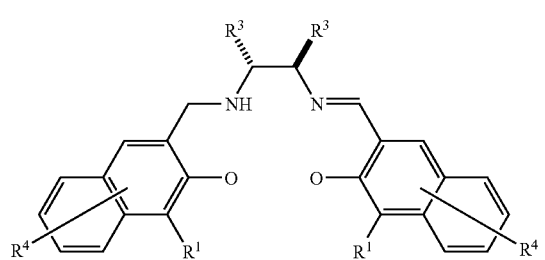
(9)

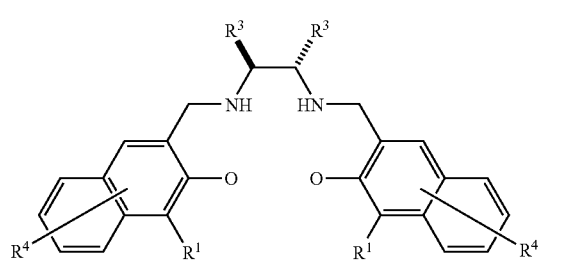
(9')

b represents an integer of 1 to 10; $R^1$, $R^2$, $R^3$ and $R^4$ are the same as described above.

When $J^1$ and $J^2$ are bonded together to represent an oxygen atom, the formula (1), formula (1'), formula (2), formula (2'), formula (3), formula (3'), formula (4) and formula (4') are mononuclear oxotitanium complexes as whole molecular structures, and when $J^1$ and $J^2$ are bonded together to form a ring represented by the formula (5) of bivalent group, the formula (1), formula (1'), formula (2), formula (2'), formula (3), formula (3'), formula (4) and formula (4') are (b+1) nuclear μ-oxotitanium complexes of multinuclear complexes as whole molecular structures.

In addition, when the formula (1), formula (1'), formula (2), formula (2'), formula (3), formula (3'), formula (4) and formula (4') are the oxotitanium complexes or the (b+1) nuclear μt-oxotitanium complexes, an optically active titanium complex may be a mixture of these oxotitanium complexes or (b+1) nuclear μ-oxotitanium complexes in which b is any one state of 1 to 10.

Preferable $J^1$ and $J^2$ are when $J^1$ and $J^2$ are bonded together to represent an oxygen atom, or $J^1$ and $J^2$ are bonded together to form a ring represented by the formula (5) of bivalent group. In such cases, an optically active titanium complex is a mononuclear oxotitanium complex or a (b+1) nuclear μ-oxotitanium complex (in which b is an integer of 1 to 10).

Moreover, optically active titanium complexes according to the present invention are categorized into optically active titanium-salalen complexes represented by the formula (1), formula (1'), formula (3) and formula (3'), and titanium-salan complexes represented by the above-mentioned formula (2), formula (2'), formula (4) and formula (4'), and combinations of preferable substitution groups and structures of whole molecules will be described.

The optically active titanium-salalen complexes represented by the above-mentioned formula (1), formula (1'), formula (3) and formula (3') represents $J^1$ and $J^2$ are bonded together to form a ring represented by the formula (5) of bivalent group, and it is preferable that b is 1 in the formula (5). In this case, the formula (1), formula (1'), formula (3) and formula (3') are binuclear μ-oxotitanium complexes represented by the following formula (18) and formula (18') as whole molecular structures.

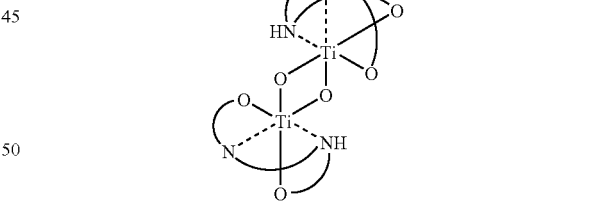
(18)

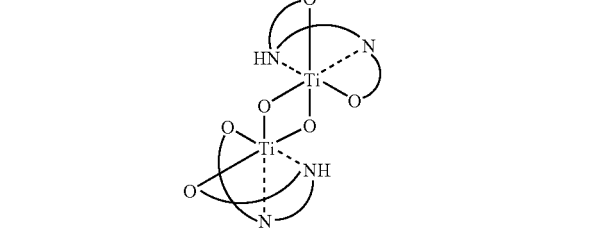
(18')

(in which, O—NH—N—O is the following formula (19) in the formula (1), following formula (19') in the formula (1'), following formula (20) in the formula (2) and following formula (20') in the formula (2')), and

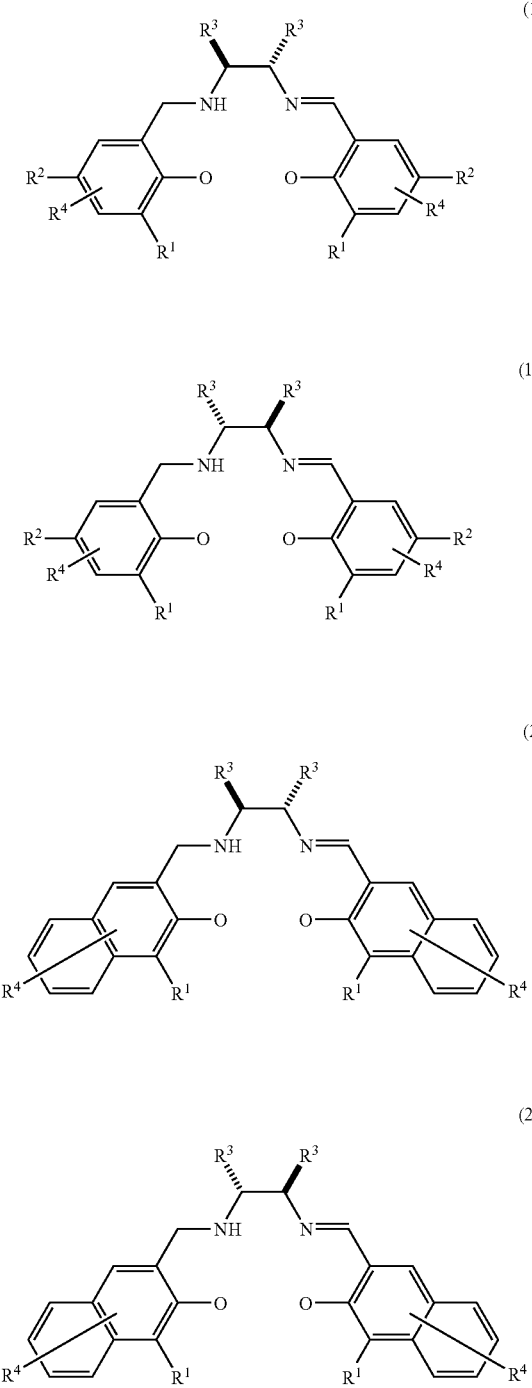

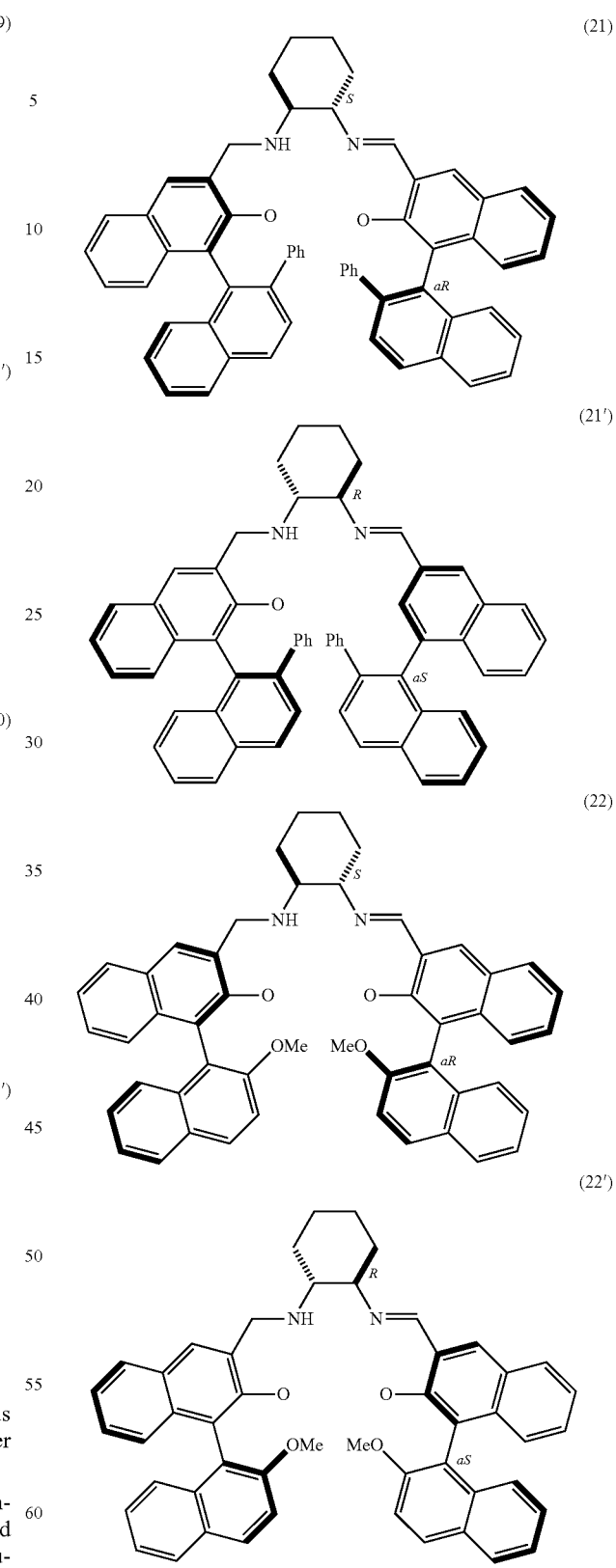

(in which $R^1$, $R^2$, $R^3$ and $R^4$ are the same as previous definitions) the complex of the formula (18') is an enantiomer of the complex of the formula (18)).

Of the optically active titanium-salalen complexes, combinations of particularly preferable substitution groups and structures of whole molecules will be described. A particularly preferable optically active titanium-salalen complexes are represented by the formula (18) and formula (18'), and the partial structures of O—NH—N—O in the formulae which are represented by the following formula (21), (21'), (22) or (22')

are a binuclear (aRSΔ,aRSΔ)-di-μ-oxotitanium complex and a binuclear (aSRΔ,aSRΔ)-di-μ-oxotitanium complex.

Combinations of particularly preferable substitution groups of the optically active titanium-salan complexes represented by the formula (2), formula (2'), formula (4) and formula (4') include mononuclear oxotitanium complexes represented by the following formulae (23), (23'), (24) and (24'),

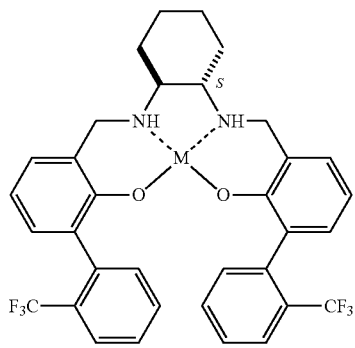
(23)

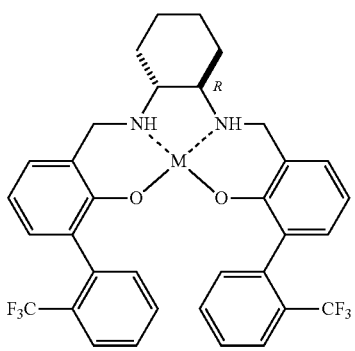
(23')

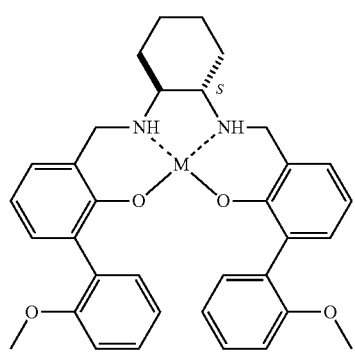
(24)

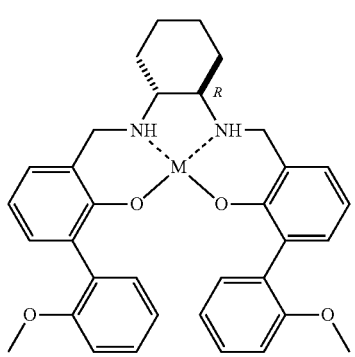
(24')

(in which M represents $TiJ^1J^2$, and $J^1$ and $J^2$ are bonded together to represent an oxygen atom, or $J^1$ and $J^2$ are bonded together to form a ring represented by the formula (5) of bivalent group, in which b is an integer of 1 to 10, and partial structures of O-E-O are represented by the following formula (25), (25'), (26) or (26')

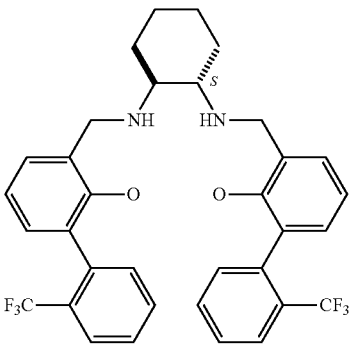
(25)

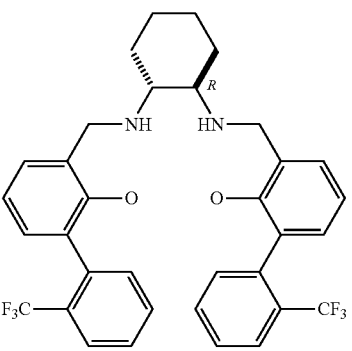
(25')

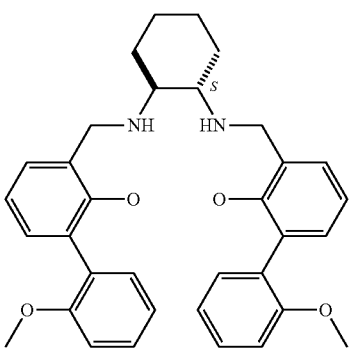
(26)

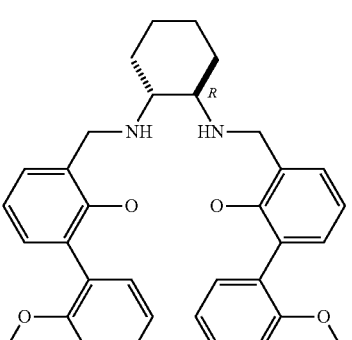
(26')

or μ-oxotitanium oligomer which is formed by bonding (b+1) pieces of mononuclear oxotitanium complexes (b is an integer of 1 to 10).

Then, a process for producing optically active titanium complexes represented by the formula (1), formula (1'), formula (2), formula (2'), formula (3), formula (3'), formula (4) and formula (4') will be described.

Salen ligands represented by the formula (29), formula (29'), formula (31) and formula (31') which are the ligands of titanium-salan complexes represented by the formula (2), formula (2'), formula (4) and formula (4') respectively can be produced by reducing salen compounds represented by the following formula (28), formula (28'), formula (30) and formula (30'), respectively.

Examples of reducing agents include sodium borohydride ($NaBH_4$), sodium borocyanohydride ($NaBH_3CN$) and lithium aluminum hydride ($LiAlH_4$), and sodium borohydride ($NaBH_4$) is preferable.

Salen Ligand (28)

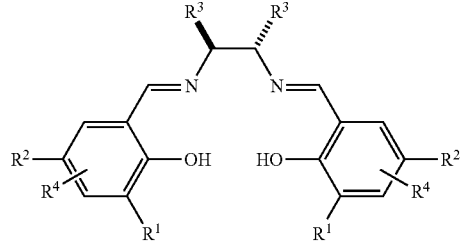

Salen Ligand (28')

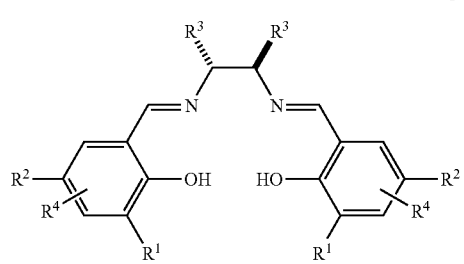

Salen Ligand (29)

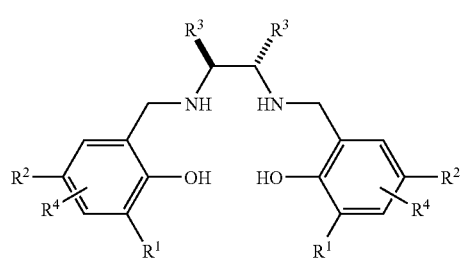

Salen Ligand (29')

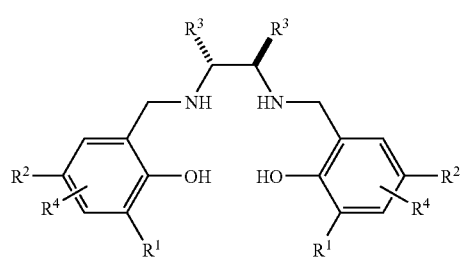

Salen Ligand (30)

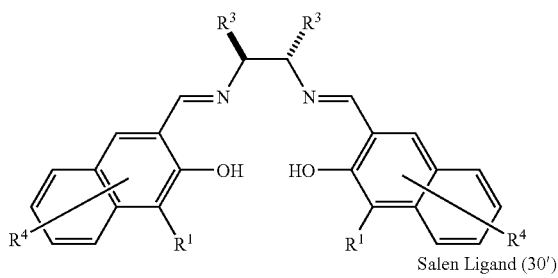

Salen Ligand (30')

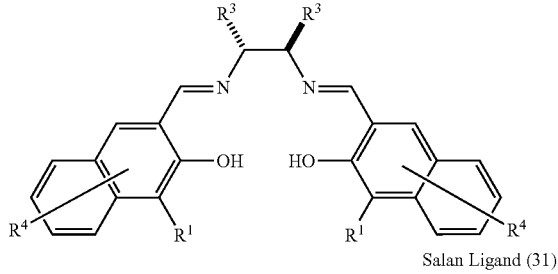

Salen Ligand (31)

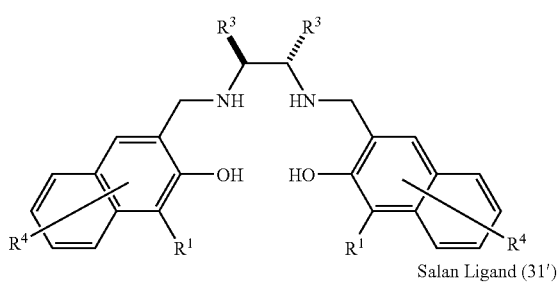

Salen Ligand (31')

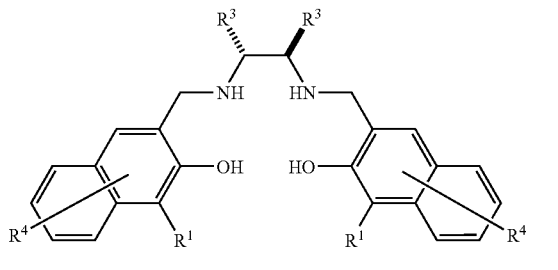

Optically active titanium salan complexes represented by the formula (2), formula (2'), formula (4) and formula (4') can be produced by reacting the corresponding salan ligands with a titanium alkoxide, titanium tetrachloride or titanium tetrabromide in an organic solvent such as dichloromethane, and then treating the resultant mixture with water or a water-containing solvent (a mixed solvent made by containing 0.1 to 100% by mass of water in an organic solvent, and examples of an organic solvent for use include THF, methanol and i-propanol). A used amount of water is preferably in the range of 1 to 1,000 mols and more preferably in the range of 1 to 10 mols to an equivalent of the above-mentioned salan ligand.

In addition, the above-mentioned optically active titanium-salan complex is generated in situ, and asymmetric epoxidation of a chromene compound can also be conducted without isolating the complex as a catalyst.

On this occasion, addition of water can also be conducted by adding hydrogenperoxide aqueous solution used as an oxidation agent.

As titanium compounds, titanium alkoxides are preferable, and examples of the titanium alkoxides include titanium tetramethoxide, titanium tetraethoxide, titanium tetra-n-propoxide, titanium tetra-i-propoxide, titanium tetra-n-butoxide and titanium tetra-t-butoxide. Of these titanium alkoxides, titanium tetra-i-propoxide (Ti(Oi-Pr)$_4$) is more preferable. A used amount of a titanium alkoxide is preferably in the range of 1 to 2 mols per mol of the above-mentioned salan ligand.

Optically active titanium salalen complexes represented by the formula (1), formula (1'), formula (3) and formula (3') can be produced by the method described in Non-patent Document 8 (Angew. Chem. Int. Ed. (2005), 44, 4935-4939). That is, the salalen complex can be produced by reacting the corresponding salen ligand with a titanium alkoxide; forming a titanium complex with reducing one of two imino bonds in the salen ligand by using Meerwein-Ponndrof-Verley (MPV) reduction reaction; and after completion of the reaction, treating the resultant mixture with water or a water-containing solvent (a mixed solvent made by containing 0.1 to 100% by mass of water in an organic solvent, and examples of an organic solvent for use include THF, methanol and i-propanol).

In addition, the above-mentioned optically active titanium-salalen complex is generated in situ, and asymmetric epoxidation of a chromene compound can also be conducted without isolating the complex as a catalyst.

Examples of the titanium alkoxides include titanium tetramethoxide, titanium tetraethoxide, titanium tetra-n-propoxide, titanium tetra-i-propoxide, titanium tetra-n-butoxide and tetra-t-butoxide. Of these titanium alkoxides, titanium tetra-i-propoxide (Ti(Oi-Pr)$_4$) is preferable. Used amount of a titanium alkoxide is preferably in a range of 1 to 2 mols per mol of the above-mentioned salan ligand. Used amount of water is preferably in a range of 1 to 1000 mols and more preferably in a range of 1 to 10 mols to an equivalent of the above-mentioned salan ligand.

Examples of reaction solvents used in the production of the optically active titanium complex include an aprotic organic solvent, a protic organic solvent or a mixture thereof. Examples of the aprotic organic solvent include a halogen-type solvent, an aromatic hydrocarbon-type solvent, an ester-type solvent, an ether-type solvent or a nitrile type-solvent, and specifically include dichloromethane, chloroform, 1,2-dichloroethane, chlorobenzene, toluene, ethyl acetate, tetrahydrofuran, diethylether, butyronitrile, propionitrile and acetonitrile. Examples of the protic organic solvent include an alcohol type solvent, and specifically include ethanol, i-propanol and t-butanol.

A preferable reaction solvent is dichloromethane, 1,2-dichloroethane, chlorobenzene, toluene and ethyl acetate of the aprotic organic solvent.

In a producing process of the present invention, one of the enantiomers of a chromene oxide compound can be produced in high selectivity by asymmetric epoxidation of a chromene compound, which is a starting material, using an optically active titanium complex of the formula (1), formula (1'), formula (2), formula (2'), formula (3), formula (3'), formula (4) and formula (4'). Specifically, one of the two enantiomers of an optically active chromene oxide compound can be selectively produced by using any of the complex of the formula (1) and of the complex of the formula (1'); one of the two enantiomers of an optically active chromene oxide compound can be selectively produced by using any of the complex of the formula (2) and of the complex of the formula (2'); one of the two enantiomers of an optically active chromene oxide compound can be selectively produced by using any of the complex of the formula (3) and of the complex of the formula (3'); and one of the two enantiomers of an optically active chromene oxide compound can be selectively produced by using any of the complex of the formula (4) and of the complex of the formula (4').

A process for producing an optically active chromene oxide compound according to the present invention will now be described.

This process is a process for producing an optically active chromene oxide compound represented by the formula (14), formula (15) formula (16) or formula (17),

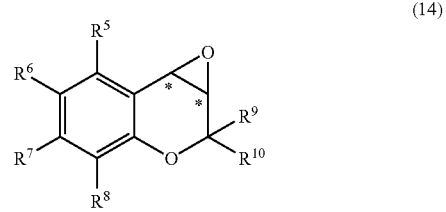

(14)

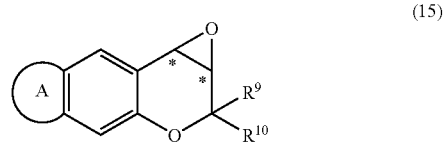

(15)

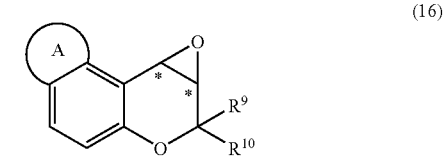

(16)

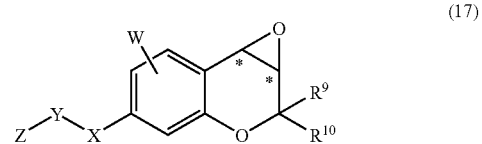

(17)

in which $R^5$, $R^6$, $R^7$, $R^8$, $R^9$, $R^{10}$, A, W, X, Y and Z are the same as described below and an absolute configuration of the carbon atoms indicated by * are (R) or (S); by dissolving a chromene compound represented by the formula (10), formula (11), formula (12) or formula (13) and an optically active titanium complex represented by the formula (1), formula (1'), formula (2), formula (2'), formula (3), formula (3'), formula (4) and formula (4') into an organic solvent under nitrogen atmosphere or air atmosphere, and by asymmetric epoxidation by adding an oxidizing agent to the reaction solution and stirring,

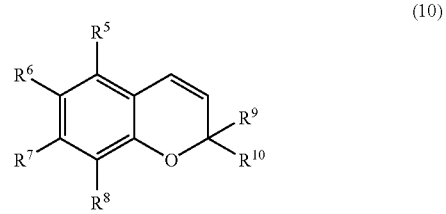

(10)

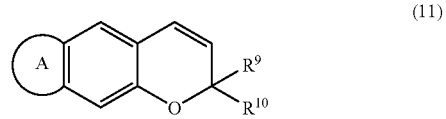

(11)

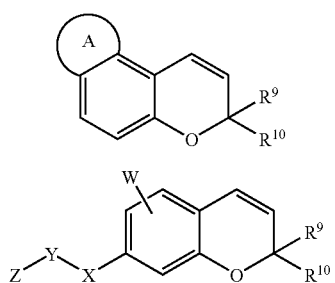

in which $R^5$, $R^6$, $R^7$ and $R^8$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom, phenyl group (the phenyl group may be optionally substituted with a halogen atom, hydroxy group, cyano group, nitro group, $C_{1-4}$ alkyl group or $C_{1-4}$ alkoxy group)), $C_{1-4}$ alkylcarbonyl(N—$C_{1-4}$ alkyl)amino group (the alkylcarbonyl(N-alkyl)amino group may be optionally substituted with a halogen atom), $C_{1-4}$ alkoxycarbonyl group (the alkoxycarbonyl group may be optionally substituted with a halogen atom), $C_{6-10}$ arylcarbonylamino group (the arylcarbonylamino may be optionally substituted with a halogen atom, $C_{1-4}$ alkyl group, $C_{1-4}$ alkoxy group, cyano group or nitro group), $C_{6-10}$ arylcarbonyl(N—$C_{1-4}$ alkyl)amino group (the arylcarbonyl(N-alkyl)amino group may be substituted with a halogen atom, $C_{1-4}$ alkyl group, $C_{1-4}$ alkoxy group, cyano group or nitro group), benzylcarbonylamino group, formyl group, carbamoyl group, $C_{1-4}$ alkylsulfonyl group, $C_{6-10}$ arylsulfony group (the alkylsulfonyl group and arylsulfony group may be substituted with a halogen atom, $C_{1-4}$ alkyl group, $C_{1-4}$ alkoxy group, cyano group or nitro group), sulfamoyl group, $C_{1-4}$ alkylsulfonamide group, $C_{6-10}$ arylsulfonamide group (the alkylsulfonamide group and arylsulfonamide group may be substituted with a halogen atom, $C_{1-4}$ alkyl group, $C_{1-4}$ alkoxy group, cyano group or nitro group), bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis($C_{6-10}$ arylsulfone)imide group (arylsulfone of the bis (arylsulfone)imide group may be substituted with a halogen atom, $C_{1-4}$ alkyl group, $C_{1-4}$ alkoxy group, cyano group or nitro group), or (N,N'—($C_{1-4}$ alkylsulfone) ($C_{6-10}$ arylsulfone))imide group (alkylsulfone and arylsulfone of the (N,N'-(alkylsulfone) (arylsulfone))imide group may be substituted with a halogen atom, $C_{1-4}$ alkyl group, $C_{1-4}$ alkoxy group, cyano group or nitro group);

$R^9$ and $R^{10}$ in the formula (10) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

$R^9$ and $R^{10}$ in the formula (11) and formula (12) each independently represent hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

partial ring structure A in the formula (11) and formula (12) represents a partial structure being represented by 5-, 6- or 7-membered ring forming a fused ring with benzene ring part (each of the 5-, 6- or 7-membered ring may be optionally substituted with h $R^{11}$ ($R^{11}$ may be optionally substituted with a halogen atom, hydroxyl group, $C_{1-6}$ alkyl group (the alkyl group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-6}$ alkoxy group (the alkoxy group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), nitro group, cyano group, formyl group, formamide group, carbamoyl group, sulfo group, sulfoamino group, sulfamoyl group, sulfonyl group, amino group, carboxyl group, $C_{1-6}$ alkylamino group, di-$C_{1-6}$ alkylamino group, $C_{1-6}$ alkylcarbonylamino group, $C_{1-6}$ alkylsulfonamide group, $C_{6-14}$ arylsulfonamide group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, $C_{1-6}$ alkylsulfonyl group, $C_{6-14}$ arylsulfonyl group, or $C_{6-14}$ arylcarbonyl group (the alkylamino group, dialkylamino group, alkylcarbonylamino group, alkylsulfonamide group, arylsulfonamide group, alkylaminocarbonyl group, dialkylaminocarbonyl group, alkylcarbonyl group, alkoxycarbonyl group, alkylsulfonyl group, arylsulfonyl group, or arylcarbonyl group may be optionally substituted with a halogen atom);

h is an integer of 1 to 6 and when h is an integer of 2 to 6, each $R^{11}$ may be the same or different); 1 to 3 of oxygen atom(s), nitrogen atom(s) or sulfur atom(s) can be contained singly or in combination as constituent atoms of the ring; the number of unsaturated bond(s) containing unsaturated bond(s) in benzene ring condensed is 1, 2 or 3 and carbon atom(s) composing the ring may be carbonyl group or thionyl group); X in the formula (13) represents $NR^{20}$ ($R^{20}$ means hydrogen atom or $C_{1-4}$ alkyl group); Y in the formula (13) represents a chemical bonding, SO or $SO_2$; Z in the formula (13) represents a $C_{1-4}$ alkyl group (the alkyl group may be optionally substituted with 1 to 5 halogen atom(s) or a phenyl group (the phenyl group may be optionally substituted with a $C_{1-4}$ alkyl group)) or phenyl group (the phenyl group may be optionally substituted with a $C_{1-4}$ alkyl group); W in the formula (13) represents a hydrogen atom, hydroxy group, $C_{1-6}$ alkoxy group (the alkoxy group may be optionally substituted with a halogen atom), halogen atom, $C_{1-4}$ alkyl group or $C_{1-6}$ alkylsulfonamide group (the alkyl group and alkylsulfonamide group may be optionally substituted with a halogen atom); and $R^9$ and $R^{10}$ in the formula (13) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom or $C_{1-6}$ alkoxy group (the alkoxy group may be optionally substituted with a halogen atom) or hydroxy group) or $C_{1-6}$ alkoxy group (the alkoxy group may be optionally substituted with a halogen atom)). This optically active chromene oxide compound can be produced by a method shown in the reaction formula 1.

Reaction formula 1

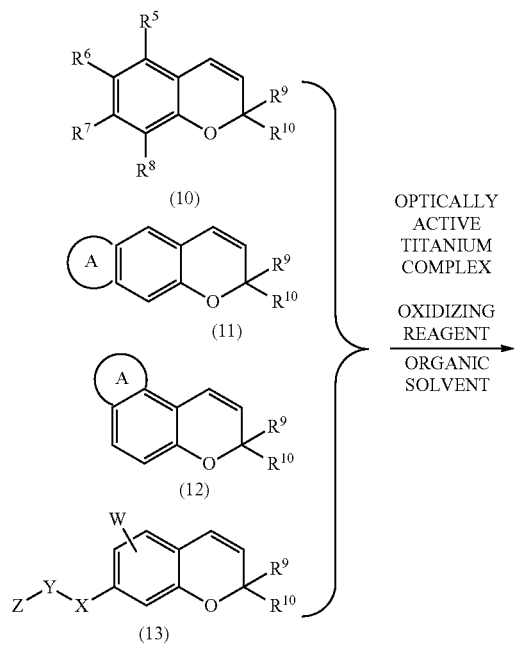

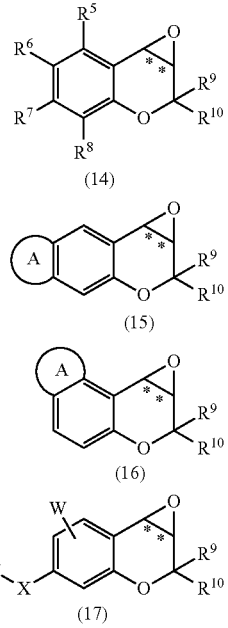

The reaction formula 1, in which $R^5$, $R^6$, $R^7$, $R^8$, $R^9$, $R^{10}$, A, W, X, Y and Z are the same as described above and an absolute configuration of the carbon atoms indicated by * is (R) or (S), illustrates a process for producing an optically active chromene oxide compound represented by the formula (14), formula (15), formula (16) and formula (17) by treating a chromene compound represented by the formula (10), formula (11), formula (12) and formula (13), respectively, with an oxidizing agent and an optically active titanium complex.

A chromene compound represented by the formula (10), formula (11), formula (12) and formula (13), which is a starting material of the present invention, can be synthesized using following general synthesis methods for benzopyran ring. Synthesis of the fused ring in the formula (11) and formula (12) can be achieved by using the following various synthesis methods for heterocycles arbitrarily in combination with synthesis methods for benzopyran ring.

General Synthesis Methods for Benzopyran Ring

A benzopyran ring can be synthesized according to the known processes (the processes described in J. M. Evans, et al., J. Med. Chem. 1984, 27, 1127., J. Med. Chem. 1986, 29, 2194., J. T. North, et al., J. Org. Chem. 1995, 60, 3397., Japanese Patent Application Publication Nos. JP-A-56-57785, JP-A-56-57786, JP-A-58-188880, JP-A-2-141, JP-A-10-87650 and JP-A-11-209366, and other references)

Indole and Oxyindole

Indole and oxyindole can be synthesized according to the known processes (the processes described in T. Sakamoto, et al., Heterocycles, 1986, 24, 31., M. Belley, et al., Synthesis, 2001, 222., A. D. Cross, et al., J. Chem. Soc., 1961, 2714 and other references).

Imidazolinone

Imidazolinone can be synthesized according to the known process (The process described in J. Kitteringham, et. al., Synthetic Commun., 2000, 30, 1937).

Quinoline

Quinoline can be synthesized according to the known processes (the processes described in S. Imor, et al., Synthetic Commun., 1996, 26, 2197., Y. Kitahara, et al., Tetrahedron, 1997, 53, 6001., A. G. Osborne, et al., J. Chem. Soc. Perkin Trans. 1993, 1, 181., R. T. Shuman, et al., J. Org. Chem., 1990, 55, 738., T. Sakamoto, et al., Chem. Pharm. Bull., 1981, 29, 2485., Y. Tsuji, et al., J. Org. Chem., 1987, 52, 1673., Z. Song, et al., J. Heterocyclic Chem., 1993, 30, 17. and other references).

Quinolinone

Quinolinone can be synthesized according to the known processes (the processes described in M. R. Sabol, et al., Synthetic Commun., 2000, 30, 427., Z-Y. Yang, et al., Tetrahedron Lett., 1999, 40, 4505., H-B Sun, et al., Synthesis, 1997, 1249., A. Guiotto, et al., J. Heterocyclic Chem., 1989, 26, 917., K. Konno, et al., Heterocycles, 1986, 24, 2169., E. Fernandez, et al., Synthesis, 1995, 1362 and other references).

Benzothiazole and Triazole

Benzothiazole and triazole can be synthesized according to the known processes (the processes described in N B. Ambati, et al., Synthetic Commun., 1997, 27, 1487., D. E. Burton, et al., J. Chem. Soc (C)., 1968, 1268. and other references).

Quinoxaline and Quinoxalinone

Quinoxaline and quinoxalinone can be synthesized according to the known processes (the processes described in J. H. Liu, et al., J. Org. Chem., 2000, 65, 3395., J. J. Li, et al., Tetrahedron Lett., 1999, 40, 4507., Y. Ahmed, et al., Bull. Chem. Soc. Jpn., 1987, 60, 1145. and other references).

Benzoxazinone

Benzoxazinone can be synthesized according to the known processes (the processes described in G. H. Jones, et al., J. Med. Chem., 1987, 30, 295., J. L. Wright, et al., J. Med. Chem., 2000, 43, 3408., M. Kluge, et al., J. Heterocyclic Chem., 1995, 32, 395. and other references).

Compounds represented by the formula (35) and (36) can be obtained by reacting the compound (33) with the compound (34) (Reference: Y. Tsuji, et al., J. Org. Chem., 1987, 52, 1673).

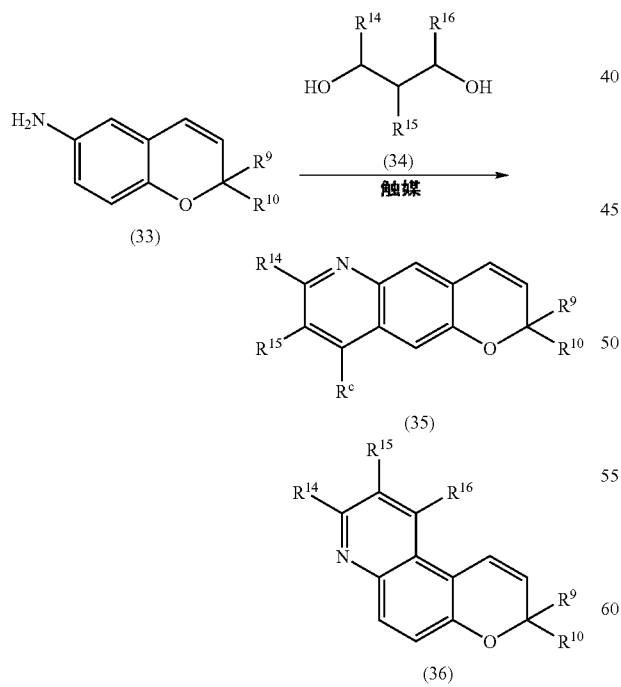

Compounds represented by the formula (35) and (36) can also be obtained by reacting the compound (33) with the compound (37) in the presence of an acid catalyst (References: Y. Kitahara, et al., Tetrahedron, 1997, 53, 6001., Z. Song, et al., J. Heterocyclic Chem., 1993, 30, 17).

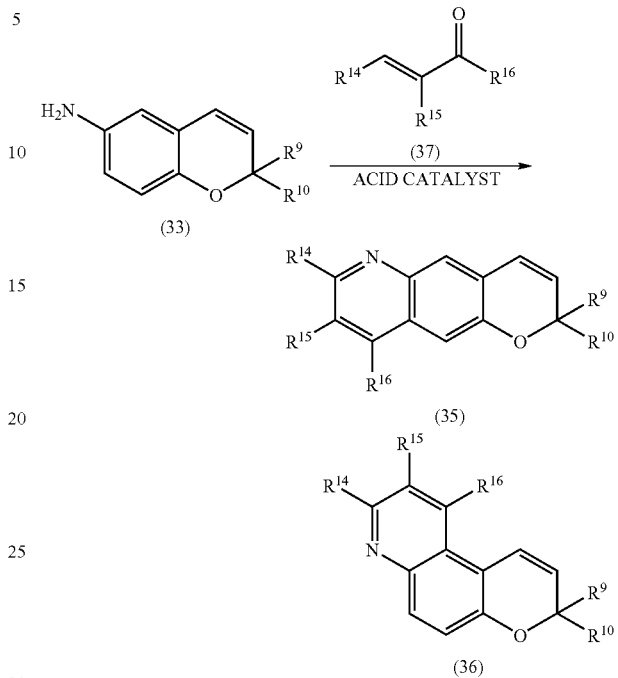

A chromene compound represented by the following formula (40) can be synthesized from a compound (38) and obtained by reducing nitro group of the compound (38) to obtain an amine compound (39) with platinum/carbon catalyst, and then mesylating the amino group of the compound (39).

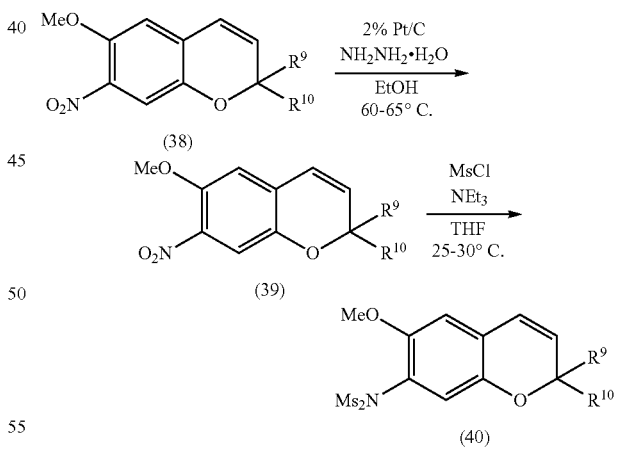

Each substitution group of chromene compounds represented by the formula (10), formula (11), formula (12) and formula (13) will be specifically described.

Each substitution group of the formula (10) will be described. Each $R^5$, $R^6$, $R^7$ and $R^8$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom, $C_{6-10}$ aryl group (the $C_{6-10}$ aryl group may be optionally substituted with a halogen atom, hydroxy group, cyano group, nitro group, $C_{1-4}$ alkyl group or $C_{1-4}$ alkoxy group)), $C_{1-4}$ alkylcarbonyl(N—$C_{1-4}$ alkyl) amino group (the alkylcarbonyl(N-alkyl)amino group may be optionally substituted with a halogen atom), $C_{1-4}$ alkoxycarbonyl group (the alkoxycarbonyl group may be optionally substituted with a halogen atom), $C_{6-10}$ arylcarbonylamino group (the arylcarbonylamino group may be optionally substituted with a halogen atom, $C_{1-4}$ alkyl group, $C_{1-4}$ alkoxy group, cyano group or nitro group), $C_{6-10}$ arylcarbonyl(N—$C_{1-4}$ alkyl)amino group (the arylcarbonyl(N-alkyl)amino group may be optionally substituted with a halogen atom, $C_{1-4}$ alkyl group, $C_{1-4}$ alkoxy group, cyano group or nitro group), benzylcarbonylamino group, formyl group, carbamoyl group, $C_{1-4}$ alkylsulfonyl group (the alkylsulfonyl group may be optionally substituted with a halogen atom), $C_{6-10}$ arylsulfony group (the arylsulfony group may be optionally substituted with a halogen atom, $C_{1-4}$ alkyl group, $C_{1-4}$ alkoxy, group cyano group or nitro group), sulfamoyl group, $C_{1-4}$ alkylsulfonamide group, $C_{6-10}$ arylsulfonamide group (the alkylsulfonamide group and arylsulfonamide group may be optionally substituted with a halogen atom, $C_{1-4}$ alkyl group, $C_{1-4}$ alkoxy group, cyano group or nitro group), bis($C_{1-4}$ alkylsulfone)imide group (alkylsulfone of the bis(alkylsulfone)imide group may be optionally substituted with a halogen atom, $C_{1-4}$ alkyl group, $C_{1-4}$ alkoxy group, cyano group or nitro group), bis($C_{6-10}$ arylsulfone)imide group (arylsulfone of the bis(arylsulfone)imide group may be optionally substituted with a halogen atom, $C_{1-4}$ alkyl group, $C_{1-4}$ alkoxy group, cyano group or nitro group), or (N,N'—($C_{1-4}$ alkylsulfone) ($C_{6-10}$ arylsulfone))imide group (alkylsulfone and arylsulfone of the (N,N'-(alkylsulfone) (arylsulfone))imide group may be optionally substituted with a halogen atom, $C_{1-4}$ alkyl group, $C_{1-4}$ alkoxy group, cyano group or nitro group).

Each substitution group of $R^5$, $R^6$, $R^7$ and $R^8$ in formula (10) will be specifically described.

Examples of the halogen atom include a fluorine atom, chlorine atom, bromine atom and iodine atom; examples of the $C_{1-4}$ alkyl group include a methyl group, trifluoromethyl group, trichloromethyl group, ethyl group, n-propyl group, i-propyl group, c-propyl group, n-butyl group, i-butyl group, s-butyl group, t-butyl group and c-butyl group; examples of the $C_{1-4}$ alkoxy group include a methoxy group, trifluoromethoxy group, trichloromethoxy group, ethoxy group, n-propoxy group, i-propoxy group, c-propoxy group, n-butoxy group, i-butoxy group, s-butoxy group, t-butoxy group and c-butoxy group; examples of the $C_{1-4}$ alkylcarbonylamino group include a methylcarbonylamino group, trifluoromethylcarbonylamino group, trichloromethylcarbonylamino group, ethylcarbonylamino group, n-propylcarbonylamino group, i-propylcarbonylamino group, c-propylcarbonylamino group, n-butylcarbonylamino group, i-butylcarbonylamino group, s-butylcarbonylamino group, t-butylcarbonylamino group, c-butylcarbonylamino group, p-methoxyphenylmethylcarbonylamino group, p-nitrophenylmethylcarbonylamino group and p-methoxyphenylethylcarbonylamino group; examples of the $C_{1-4}$ alkylcarbonyl(N—$C_{1-4}$ alkyl)amino group include a methylcarbonyl (N-methyl)amino group, trifluoromethylcarbonyl(N-methyl) amino group, methylcarbonyl(N-ethyl)amino group, trifluoromethylcarbonyl(N-ethyl)amino group, ethylcarbonyl(N-ethyl)amino group, n-propylcarbonyl(N-ethyl)amino group, i-propylcarbonyl(N-ethyl)amino group, c-propylcarbonyl(N-ethyl)amino group, n-butylcarbonyl(N-ethyl)amino group, i-butylcarbonyl(N-ethyl)amino group, s-butylcarbonyl(N-ethyl)amino group, t-butylcarbonyl(N-ethyl)amino group and c-butylcarbonyl(N-ethyl)amino group; examples of the $C_{1-4}$ alkoxycarbonyl group include a methoxycarbonyl group, trifluoromethoxycarbonyl group, ethoxycarbonyl group, n-propoxycarbonyl group, i-propoxycarbonyl group, c-propoxycarbonyl group, n-butoxycarbonyl group, i-butoxycarbonyl group, s-butoxycarbonyl group, t-butoxycarbonyl group and c-butoxycarbonyl group; examples of the $C_{6-10}$ arylcarbonylamino group include a phenylcarbonylamino group, 1-naphthylcarbonylamino group and 2-naphthylcarbonylamino group; examples of the $C_{6-10}$ arylcarbonyl(N—$C_{1-4}$ alkyl)amino group include a phenylcarbonyl (N-methyl) amino group, phenylcarbonyl(N-ethyl)amino group, 1-naphthylcarbonyl(N-ethyl)amino group and 2-naphthylcarbonyl(N-ethyl)amino group; examples of the $C_{1-4}$ alkylsulfonyl group include a methanesulfonyl group, trifluoromethanesulfonyl group, ethanesulfonyl group, n-propanesulfonyl group, i-propanesulfonyl group, c-propanesulfonyl group, n-butanesulfonyl group, i-butanesulfonyl group, s-butanesulfonyl group, t-butanesulfonyl group and c-butanesulfonyl group; examples of the $C_{6-10}$ arylsulfonyl group include benzenesulfonyl group, p-fluorobenzenesulfonyl group, p-toluenesulfonyl group, 1-naphthalenesulfonyl group and 2-naphthalenesulfonyl group; examples of the $C_{1-4}$ alkylsulfonamide group include a methanesulfonamide group, trifluoromethanesulfonamide group, ethanesulfonamide group, n-propanesulfonamide group, i-propanesulfonamide group, c-propanesulfonamide group, n-butanesulfonamide group, i-butanesulfonamide group, s-butanesulfonamide group, t-butanesulfonamide group and c-butanesulfonamide group; examples of the $C_{6-10}$ arylsulfonamide group include a benzenesulfonamide group, p-fluorobenzenesulfonamide group, p-toluenesulfonamide group, 1-naphthalenesulfonamide group and 2-naphthalenesulfonamide group; examples of the bis($C_{1-4}$ alkylsulfone)imide group include a bis(methanesulfone)imide group, bis(trifluoromethanesulfone)imide group, bis(ethanesulfone)imide group, bis(n-propanesulfone)imide group, bis(1-propanesulfone)imide group, bis(c-propanesulfone)imide group, bis (n-butanesulfone)imide group, bis(1-butanesulfone)imide group, bis(s-butanesulfone)imide group, bis(t-butanesulfone)imide group and bis(c-butanesulfone)imide group; examples of the bis($C_{6-10}$ arylsulfone)imide group include a bis(benzenesulfone)imide group, bis(p-fluorobenzenesulfone)imide group, bis(p-toluenesulfone)imide group, bis (1-naphthalenesulfone)imide group and bis(2-naphthalenesulfone)imide group; and examples of the (N,N'—($C_{1-4}$ alkylsulfone)($C_{6-10}$ arylsulfone))imide group include a (N,N'-(methane)(benzene))imide group, (N,N'-(trifluoromethane)(benzene))imide group, (N,N'-(trifluoromethane) (p-fluorobenzene))imide group, (N,N'-(ethane)(benzene)) imide group, (N,N'-(methane)(p-toluene))imide group, (N,N'-(trifluoromethane)(p-toluene))imide group, (N,N'-(ethane)(p-toluene))imide group, (N,N'-(methane)(1-naphthalene))imide group, (N,N'-(trifluoromethane)(1-naphthalene))imide group, (N,N'-(ethane)(1-naphthalene))imide group, (N,N'-(methane)(2-naphthalene))imide group, (N,N'-(trifluoromethane)(2-naphthalene))imide group and (N,N'-(ethane)(2-naphthalene))imide group.

$R^5$ and $R^6$ in the formula (10) independently preferably represent a hydrogen atom, cyano group, nitro group, fluorine atom, chlorine atom, bromine atom, iodine atom, methyl group, trifluoromethyl group, ethyl group, n-propyl group, i-propyl group, c-propyl group, n-butyl group, i-butyl group, s-butyl group, t-butyl group, c-butyl group, methoxy group, trifluoromethoxy group, ethoxy group, n-propoxy group, i-propoxy group, c-propoxy group, n-butoxy group, i-butoxy group, s-butoxy group, t-butoxy group, c-butoxy group, methylcarbonylamino group, trifluoromethylcarbonylamino group, ethylcarbonylamino group, n-propylcarbonylamino group, i-propylcarbonylamino group, c-propylcarbonylamino group, n-butylcarbonylamino group, i-butylcarbonylamino group, s-butylcarbonylamino group, t-butylcarbonylamino group, c-butylcarbonylamino group, methylcarbonyl(N-methyl)amino group, trifluoromethylcarbonyl(N-methyl)amino group, methylcarbonyl(N-ethyl)amino group, trifluoromethylcarbonyl(N-ethyl)amino group, ethylcarbonyl(N-ethyl)amino group, n-propylcarbonyl(N-ethyl)amino group, i-propylcarbonyl(N-ethyl)amino group, c-propylcarbonyl(N-ethyl)amino group, n-butylcarbonyl(N-ethyl)amino group, i-butylcarbonyl(N-ethyl)amino group, s-butylcarbonyl(N-ethyl)amino group, t-butylcarbonyl(N-ethyl)amino group, c-butylcarbonyl(N-ethyl)amino group, methoxycarbonyl group, trifluoromethoxycarbonyl group, ethoxycarbonyl group, n-propoxycarbonyl group, i-propoxycarbonyl group, phenylcarbonylamino group, 1-naphthylcarbonylamino group, 2-naphthylcarbonylamino group, phenylcarbonyl(N-methyl)amino group, phenylcarbonyl(N-ethyl)amino group, 1-naphthylcarbonyl(N-ethyl)amino group, 2-naphthylcarbonyl(N-ethyl)amino group, benzylcarbonylamino group, formyl group, carbamoyl group, methanesulfonamide group, trifluoromethanesulfonamide group, ethanesulfonamide group, n-propanesulfonamide group, i-propanesulfonamide group, c-propanesulfonamide group, n-butanesulfonamide group, i-butanesulfonamide group, s-butanesulfonamide group, t-butanesulfonamide group, c-butanesulfonamide group, bis(methanesulfone)imide group, bis(trifluoromethanesulfone)imide group, bis(ethanesulfone)imide group, bis(n-propanesulfone)imide group, bis(1-propanesulfone)imide group, bis(c-propanesulfone)imide group, bis(n-butanesulfone)imide group, bis(1-butanesulfone)imide group, bis(s-butanesulfone)imide group, bis(t-butanesulfone)imide group, bis(c-butanesulfone)imide group, bis(benzenesulfone)imide group, bis(p-toluenesulfone)imide group, bis(1-naphthalenesulfone)imide group, bis(2-naphthalenesulfone)imide group, (N,N'-(methane)(benzene))imide group, (N,N'-(trifluoromethane)(benzene))imide group, (N,N'-(ethane)(benzene))imide group, (N,N'-(methane)(p-toluene))imide group, (N,N'-(trifluoromethane)(p-toluene))imide group, (N,N'-(ethane)(p-toluene))imide group, (N,N'-(methane)(1-naphthalene))imide group, (N,N'-(trifluoromethane)(1-naphthalene))imide group, (N,N'-(ethane)(1-naphthalene))imide group, (N,N'-(methane)(2-naphthalene))imide group, (N,N'-(trifluoromethane)(2-naphthalene))imide group and (N,N'-(ethane)(2-naphthalene))imide group, and more preferable hydrogen atom, nitro group, fluorine atom, chlorine atom, methoxy group, methylcarbonylamino group, methylcarbonyl(N-ethyl)amino group, bis(trifluoromethanesulfone)imide group, (N,N'-(trifluoromethane)(benzene))imide group and (N,N'-(trifluoromethane)(p-toluene))imide group.

$R^7$ in the formula (10) preferably represents a hydrogen atom, cyano group, nitro group, methanesulfonamide group, trifluoromethanesulfonamide group, ethanesulfonamide group, n-propanesulfonamide group, i-propanesulfonamide group, c-propanesulfonamide group, n-butanesulfonamide group, i-butanesulfonamide group, s-butanesulfonamide group, t-butanesulfonamide group, c-butanesulfonamide group, bis(methanesulfone)imide group, bis(trifluoromethanesulfone)imide group, bis(ethanesulfone)imide group, bis(n-propanesulfone)imide group, bis(i-propanesulfone)imide group, bis(c-propanesulfone)imide group, bis(n-butanesulfone)imide group, bis(i-butanesulfone)imide group, bis(s-butanesulfone)imide group, bis(t-butanesulfone)imide group, bis(c-butanesulfone)imide group, bis(benzenesulfone)imide group, bis(p-toluenesulfone)imide group, bis(1-naphthalenesulfone)imide group, bis(2-naphthalenesulfone)imide group, (N,N'-(methane)(benzene))imide group, (N,N'-(trifluoromethane)(benzene))imide group, (N,N'-(trifluoromethane)(p-fluorobenzene))imide group, (N,N'-(ethane)(benzene))imide group, (N,N'-(methane)(p-toluene))imide group, (N,N'-(trifluoromethane)(p-toluene))imide group, (N,N'-(ethane)(p-toluene))imide group, (N,N'-(methane)(1-naphthalene))imide group, (N,N'-(trifluoromethane)(1-naphthalene))imide group, (N,N'-(ethane)(1-naphthalene))imide group, (N,N'-(methane)(2-naphthalene))imide group, (N,N'-(trifluoromethane)(2-naphthalene))imide group and (N,N'-(ethane)(2-naphthalene))imide group, and more preferable hydrogen atom, nitro group, bis(methanesulfone)imide group, bis(trifluoromethanesulfone)imide group, (N,N'-(trifluoromethane)(benzene))imide group and (N,N'-(trifluoromethane)(p-toluene))imide group.

$R^8$ in the formula (10) is preferably hydrogen atom, fluorine atom, chlorine atom, cyano group, nitro group, methyl group, trifluoromethyl group, ethyl group, n-propyl group, i-propyl group, c-propyl group, n-butyl group, i-butyl group, s-butyl group, t-butyl group and c-butyl group, and more preferably hydrogen atom, fluorine atom, nitro group, methyl group and trifluoromethyl group.

$R^9$ and $R^{10}$ in the formula (10) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom)).

Each substitution group of $R^9$ and $R^{10}$ in the formula (10) will be specifically described. Examples of the $C_{1-6}$ alkyl group include a methyl group, trifluoromethyl group, ethyl group, n-propyl group, i-propyl group, n-butyl group, i-butyl group, s-butyl group, t-butyl group, 1-pentyl group, 2-pentyl group, 3-pentyl group, i-pentyl group, neopentyl group, 2,2-dimethylpropyl group, 1-hexyl group, 2-hexyl group, 3-hexyl group, 1-methyl-n-pentyl group, 1,1,2-trimethyl-n-propyl group, 1,2,2-trimethyl-n-propyl group and 3,3-dimethyl-n-butyl group; and examples of the $C_{6-14}$ aryl group include a phenyl group, o-biphenylyl group, m-biphenylyl group, p-biphenylyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group and 9-phenanthryl group.

$R^9$ and $R^{10}$ in the formula (10) are preferably hydrogen atom, methyl group, trifluoromethyl group, ethyl group and phenyl group, and more preferably methyl group.

Each substitution group in the formula (11) and formula (12) will be described.

$R^9$ and $R^{10}$ in the formula (11) and formula (12) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom)).

Each substitution group of $R^9$ and $R^{10}$ in the formula (11) and formula (12) will be specifically described.

Examples of the $C_{1-6}$ alkyl group include a methyl group, trifluoromethyl group, ethyl group, n-propyl group, i-propyl group, n-butyl group, i-butyl group, s-butyl group, t-butyl group, 1-pentyl group, 2-pentyl group, 3-pentyl group, i-pentyl group, neopentyl group, 2,2-dimethylpropyl group, 1-hexyl group, 2-hexyl group, 3-hexyl group, 1-methyl-n-pentyl group, 1,1,2-trimethyl-n-propyl group, 1,2,2-trimethyl-n-propyl group and 3,3-dimethyl-n-butyl group; and examples of the $C_{6-14}$ aryl group include a phenyl group, o-biphenylyl group, m-biphenylyl group, p-biphenylyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group and 9-phenanthryl group.

$R^9$ and $R^{10}$ in the formula (11) and formula (12) are preferably hydrogen atom, methyl group, trifluoromethyl group, ethyl group and phenyl group, and more preferably methyl group.

Partial ring structure A in the formula (11) and formula (12) will be described. The partial ring structure A means that a partial structure is represented by 5-, 6- or 7-membered ring forming a fused ring with benzene ring part (each of the 5-, 6- or 7-membered ring may be optionally substituted with h $R^{11}$ ($R^{11}$ may be optionally substituted with a halogen atom, hydroxy group, $C_{1-6}$ alkyl group (the alkyl group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-6}$ alkoxy group (the alkoxy group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), nitro group, cyano group, formyl group, formamide group, carbamoyl group, sulfo group, sulfoamino group sulfamoyl group, sulfonyl group, amino group, carboxyl group, $C_{1-6}$ alkylamino group, di-$C_{1-6}$ alkylamino group, $C_{1-6}$ alkylcarbonylamino group, $C_{1-6}$ alkylsulfonamide group, $C_{6-14}$ arylsulfonamide group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, $C_{1-6}$ alkylsulfonyl group, $C_{6-14}$ arylsulfonyl group, or $C_{6-14}$ arylcarbonyl group (the alkylamino group, dialkylamino group, alkylcarbonylamino group, alkylsulfonamide group, arylsulfonamide group, alkylaminocarbonyl group, dialkylaminocarbonyl group, alkylcarbonyl group, alkoxycarbonyl group, alkylsulfonyl group, arylsulfonyl group, or arylcarbonyl group may be optionally substituted with a halogen atom); h is an integer of 1 to 6 and when h is an integer of 2 to 6, each $R^{11}$ may be the same or different); 1 to 3 of oxygen atom(s), nitrogen atom(s) or sulfur atom(s) can be contained singly or in combination as constituent atoms of the ring; the number of unsaturated bond(s) containing unsaturated bond(s) in benzene ring condensed is 1, 2 or 3 and carbon atom(s) composing the ring may be carbonyl or thiocarbonyl).

The $R^{11}$ will be specifically described.

Examples of the halogen atom include a fluorine atom, chlorine atom, bromine atom and iodine atom;

examples of the $C_{1-6}$ alkyl group include a methyl group, trifluoromethyl group, ethyl group, n-propyl group, i-propyl group, n-butyl group, i-butyl group, s-butyl group, t-butyl group, 1-pentyl group, 2-pentyl group, 3-pentyl group, i-pentyl group, neopentyl group, 2,2-dimethylpropyl group, 1-hexyl group, 2-hexyl group, 3-hexyl group, 1-methyl-n-pentyl group, 1,1,2-trimethyl-n-propyl group, 1,2,2-trimethyl-n-propyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, trifluoromethylcarbonylaminomethyl group, ethylcarbonylaminomethyl group, methylcarbonylaminoethyl group, ethylcarbonylaminoethyl group, methoxycarbonylmethyl group, trifluoromethoxycarbonylmethyl group, ethoxycarbonylmethyl group, methoxycarbonylethyl group and ethoxycarbonylethyl group;

examples of the $C_{1-6}$ alkoxy group include a methoxy group, trifluoromethoxy group, ethoxy group, n-propoxy group, i-propoxy group, n-butoxy group, i-butoxy group, s-butoxy group, t-butoxy group, 1-pentyloxy group, 2-pentyloxy group, 3-pentyloxy group, i-pentyloxy group, neopentyloxy group, 2,2-dimethylpropoxy group, 1-hexyloxy group, 2-hexyloxy group, 3-hexyloxy group, 1-methyl-n-pentyloxy group, 1,1,2-trimethyl-n-propoxy group, 1,2,2-trimethyl-n-propoxy group, 3,3-dimethyl-n-butoxy group, methylcarbonyloxymethoxy group, ethylcarbonyloxymethoxy group, methylcarbonyloxyethoxy group, ethylcarbonyloxyethoxy group, methylcarbonylaminomethoxy group, trifluoromethylcarbonylaminomethoxy group, ethylcarbonylaminomethoxy group, methylcarbonylaminoethoxy group, ethylcarbonylaminoethoxy group, methoxycarbonylmethoxy group, trifluoromethoxycarbonylmethoxy group, ethoxycarbonylmethoxy group, methoxycarbonylethoxy group and ethoxycarbonylethoxy group;

examples of the $C_{1-6}$ alkylamino group includes a methylamino group, trifluoromethylamino group, ethylamino group, n-propylamino group, i-propylamino group, c-propylamino group, n-butylamino group, i-butylamino group, s-butylamino group, t-butylamino group, c-butylamino group, 1-pentylamino group, 2-pentylamino group, 3-pentylamino group, i-pentylamino group, neopentylamino group, t-pentylamino group, c-pentylamino group, 1-hexylamino group, 2-hexylamino group, 3-hexylamino group, c-hexylamino group, 1-methyl-n-pentylamino group, 1,1,2-trimethyl-n-propylamino group, 1,2,2-trimethyl-n-propylamino group and 3,3-dimethyl-n-butylamino group;

examples of the di-$C_{1-6}$ alkylamino group include a dimethylamino group, di-(trifluoromethyl)amino group, diethylamino group, di-n-propylamino group, di-i-propylamino group, di-c-propylamino group, di-n-butylamino group, di-1-butylamino group, di-s-butylamino group, di-t-butylamino group, di-c-butylamino group, di-1-pentylamino group, di-2-pentylamino group, di-3-pentylamino group, di-1-pentylamino group, di-neopentylamino group, di-t-pentylamino group, di-c-pentylamino group, di-1-hexylamino group, di-2-hexylamino group, di-3-hexylamino group, di-c-hexylamino group, di-(1-methyl-n-pentyl)amino group, di-(1,1,2-trimethyl-n-propyl)amino group, di-(1,2,2-trimethyl-n-propyl) amino group, and di-(3,3-dimethyl-n-butyl)amino group, methyl(ethyl)amino group, methyl(n-propyl)amino group, methyl(i-propyl)amino group, methyl(c-propyl)amino group, methyl(n-butyl)amino group, methyl(1-butyl)amino group, methyl(s-butyl)amino group, methyl(t-butyl)amino group, methyl(c-butyl)amino group, ethyl(n-propyl)amino group, ethyl(i-propyl)amino group, ethyl(c-propyl)amino group, ethyl(n-butyl)amino group, ethyl(1-butyl)amino group, ethyl(s-butyl)amino group, ethyl(t-butyl)amino group, ethyl(c-butyl)amino group, n-propyl(i-propyl)amino group, n-propyl(c-propyl)amino group, n-propyl(n-butyl) amino group, n-propyl(i-butyl)amino group, n-propyl(s-butyl)amino group, n-propyl(t-butyl)amino group, n-propyl(c-butyl)amino group, i-propyl(c-propyl)amino group, i-propyl (n-butyl)amino group, i-propyl(i-butyl)amino group, i-propyl(s-butyl)amino group, i-propyl(t-butyl)amino group, i-propyl(c-butyl)amino group, c-propyl(n-butyl)amino group, c-propyl(i-butyl)amino group, c-propyl(s-butyl) amino group, c-propyl(t-butyl)amino group, c-propyl(c-butyl)amino group, n-butyl(i-butyl)amino group, n-butyl(s-butyl)amino group, n-butyl(t-butyl)amino group, n-butyl(c-butyl)amino group, i-butyl(s-butyl)amino group, i-butyl(t-butyl)amino group, i-butyl(c-butyl)amino group, s-butyl(t-butyl)amino group, s-butyl(c-butyl)amino group and t-butyl (c-butyl)amino group;

examples of the $C_{1-6}$ alkylcarbonylamino group include a methylcarbonylamino group, trifluoromethylcarbonylamino group, ethylcarbonylamino group, n-propylcarbonylamino group, i-propylcarbonylamino group, n-butylcarbonylamino group, i-butylcarbonylamino group, s-butylcarbonylamino group, t-butylcarbonylamino group, 1-pentylcarbonylamino group, 2-pentylcarbonylamino group, 3-pentylcarbonylamino group, i-pentylcarbonylamino group, neopentylcarbonylamino, t-pentylcarbonylamino group, 1-hexylcarbonylamino group, 2-hexylcarbonylamino group and 3-hexylcarbonylamino group;

examples of the $C_{1-6}$ alkylsulfonamide group include a methanesulfonamide group, trifluoromethanesulfonamide group, ethanesulfonamide group, n-propanesulfonamide group, i-propanesulfonamide group, n-butanesulfonamide group, i-butanesulfonamide group, s-butanesulfonamide group, t-butanesulfonamide group, 1-pentanesulfonamide group, 2-pentanesulfonamide group, 3-pentanesulfonamide group, i-pentanesulfonamide group, neopentanesulfonamide group, t-pentanesulfonamide group, 1-hexanesulfonamide group, 2-hexanesulfonamide group and 3-hexanesulfonamide group;

examples of the $C_{6-14}$ arylsulfonamide group include a benzenesulfonamide group, p-toluenesulfonamide group, o-biphenylsulfonamide group, m-biphenylsulfonamide group, p-biphenylsulfonamide group, 1-naphthalenesulfonamide group, 2-naphthalenesulfonamide group, 1-anthracenesulfonamide group, 2-anthracenesulfonamide group, 9-anthracenesulfonamide group, 1-phenanthrenesulfonamide group, 2-phenanthrenesulfonamide group, 3-phenanthrenesulfonamide group, 4-phenanthrenesulfonamide group and 9-phenanthrenesulfonamide group;

examples of the $C_{1-6}$ alkylaminocarbonyl group include a methylaminocarbonyl group, trifluoromethylaminocarbonyl group, ethyaminocarbonyl group, n-propylaminocarbonyl group, i-propylaminocarbonyl group, n-butylaminocarbonyl group, i-butylaminocarbonyl group, s-butyaminocarbonyl group, t-butylaminocarbonyl group, 1-pentylaminocarbonyl group, 2-pentylaminocarbonyl group, 3-pentylaminocarbonyl group, i-pentylaminocarbonyl group, neopentylaminocarbonyl group, t-pentylaminocarbonyl group, 1-hexylaminocarbonyl group, 2-hexylaminocarbonyl group and 3-hexylaminocarbonyl group;

examples of the di-$C_{1-6}$ alkylaminocarbonyl group include a dimethylaminocarbonyl group, di-(trifluoromethyl)aminocarbonyl group, diethylaminocarbonyl group, di-n-propylaminocarbonyl group, di-1-propylaminocarbonyl group, di-c-propylaminocarbonyl group, di-n-butylaminocarbonyl group, di-i-butylaminocarbonyl group, di-s-butylaminocarbonyl group, di-t-butylaminocarbonyl group, di-c-butylaminocarbonyl group, di-1-pentylaminocarbonyl group, di-2-pentylaminocarbonyl group, di-3-pentylaminocarbonyl group, di-1-pentylaminocarbonyl group, di-neopentylaminocarbonyl group, di-t-pentylaminocarbonyl group, di-c-pentylaminocarbonyl group, di-1-hexylaminocarbonyl group, di-2-hexylaminocarbonyl group, di-3-hexylaminocarbonyl group, di-c-hexylaminocarbonyl group, di-(1-methyl-n-pentyl)aminocarbonyl group, di-(1,1,2-trimethyl-n-propyl)aminocarbonyl group, di-(1,2,2-trimethyl-n-propyl) aminocarbonyl group, di-(3,3-dimethyl-n-butyl) aminocarbonyl group, methyl(ethyl)aminocarbonyl group, trifluoromethyl(ethyl)aminocarbonyl group, methyl(n-propyl)aminocarbonyl group, methyl(i-propyl)aminocarbonyl group, methyl(c-propyl)aminocarbonyl group, methyl(n-butyl)aminocarbonyl group, methyl(i-butyl)aminocarbonyl group, methyl(s-butyl)aminocarbonyl group, methyl(t-butyl) aminocarbonyl group, methyl(c-butyl)aminocarbonyl group, ethyl(n-propyl)aminocarbonyl group, ethyl(i-propyl)aminocarbonyl group, ethyl(c-propyl)aminocarbonyl group, ethyl(n-butyl)aminocarbonyl group, ethyl(i-butyl)aminocarbonyl group, ethyl(s-butyl)aminocarbonyl group, ethyl(t-butyl)aminocarbonyl group, ethyl(c-butyl)aminocarbonyl group, n-propyl(i-propyl)aminocarbonyl group, n-propyl(c-propyl)aminocarbonyl group, n-propyl(n-butyl)aminocarbonyl group, n-propyl(i-butyl)aminocarbonyl group, n-propyl(s-butyl)aminocarbonyl group, n-propyl(t-butyl) aminocarbonyl group, n-propyl(c-butyl)aminocarbonyl group, i-propyl(c-propyl)aminocarbonyl group, i-propyl(n-butyl)aminocarbonyl group, i-propyl(i-butyl)aminocarbonyl group, i-propyl(s-butyl)aminocarbonyl group, i-propyl(t-butyl)aminocarbonyl group, i-propyl(c-butyl)aminocarbonyl group, c-propyl(n-butyl)aminocarbonyl group, c-propyl(i-butyl)aminocarbonyl group, c-propyl(s-butyl)aminocarbonyl group, c-propyl(t-butyl)aminocarbonyl group, c-propyl (c-butyl)aminocarbonyl group, n-butyl(i-butyl) aminocarbonyl group, n-butyl(s-butyl)aminocarbonyl group, n-butyl(t-butyl)aminocarbonyl group, n-butyl(c-butyl)aminocarbonyl group, i-butyl(s-butyl)aminocarbonyl group, i-butyl(t-butyl)aminocarbonyl group, i-butyl(c-butyl)aminocarbonyl group, s-butyl(t-butyl)aminocarbonyl group, s-butyl(c-butyl)aminocarbonyl group and t-butyl(c-butyl) aminocarbonyl group;

examples of the $C_{1-6}$ alkylcarbonyl group include a methylcarbonyl group, trifluoromethylcarbonyl group, ethycarbonyl group, n-propylcarbonyl group, i-propylcarbonyl group, n-butylcarbonyl group, i-butylcarbonyl group, s-butycarbonyl group, t-butylcarbonyl group, 1-pentylcarbonyl group, 2-pentylcarbonyl group, 3-pentylcarbonyl group, i-pentylcarbonyl group, neopentylcarbonyl group, t-pentylcarbonyl group, 1-hexylcarbonyl group, 2-hexylcarbonyl group and 3-hexylcarbonyl group;

examples of the $C_{1-6}$ alkoxycarbonyl group include a methoxycarbonyl group, trifluoromethoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, 1-pentyloxycarbonyl group, 2-pentyloxycarbonyl group, 3-pentyloxycarbonyl group, i-pentyloxycarbonyl group, neopentyloxycarbonyl group, t-pentyloxycarbonyl group, 1-hexyloxycarbonyl group, 2-hexyloxycarbonyl group and 3-hexyloxycarbonyl group;

examples of the $C_{1-6}$ alkylsulfonyl group include a methanesulfonyl group, trifluoromethanesulfonyl group, ethanesulfonyl group, n-propanesulfonyl group and n-butanesulfonyl group;

examples of the $C_{6-14}$ arylsulfonyl group include a benzenesulfonyl group, p-fluorobenzenesulfonyl group, p-toluenesulfonyl group, o-biphenylsulfonyl group, m-biphenylsulfonyl group, p-biphenylsulfonyl group, 1-naphthalenesulfonyl group, 2-naphthalenesulfonyl group, 1-anthracenesulfonyl group, 2-anthracenesulfonyl group, 9-anthracenesulfonyl group, 1-phenanthrenesulfonyl group, 2-phenanthrenesulfonyl group, 3-phenanthrenesulfonyl group, 4-phenanthrenesulfonyl group and 9-phenanthrenesulfonyl group; and examples of the $C_{6-14}$ arylcarbonyl group include a phenylcarbonyl group, p-fluorophenylcarbonyl group, o-biphenylylcarbonyl group, m-biphenylylcarbonyl group, p-biphenylylcarbonyl group, 1-naphthylcarbonyl group, 2-naphthylcarbonyl group, 1-anthrylcarbonyl group, 2-anthrylcarbonyl group, 9-anthrylcarbonyl group, 1-phenanthrylcarbonyl group, 2-phenanthrylcarbonyl group, 3-phenanthrylcarbonyl group, 4-phenanthrylcarbonyl group and 9-phenanthrylcarbonyl group.

Preferable atoms and groups of the above-mentioned $R^{11}$ will be specifically described.

$R^{11}$ is preferably fluorine atom, chlorine atom, bromine atom, methyl group, trifluoromethyl group, ethyl group, n-propyl group, i-propyl group, n-butyl group, n-pentyl group, i-pentyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, trifluoromethylcarbonylaminomethyl group, ethylcarbonylaminomethyl group, methylcarbonylaminoethyl group, ethylcarbonylaminoethyl group, methoxycarbonylmethyl group, trifluoromethoxycarbonylmethyl group, ethoxycarbonylmethyl group, methoxycarbonylethyl group, ethoxycarbonylethyl group, methoxy group, trifluoromethoxy group, ethoxy group, n-propoxy group, i-propoxy group, 3,3-dimethyl-n-butoxy group, methylcarbonyloxymethoxy group, ethylcarbonyloxymethoxy group, methylcarbonyloxyethoxy group, ethylcarbonyloxyethoxy group, methylcarbonylaminomethoxy group, trifluoromethylcarbonylaminomethoxy group, ethylcarbonylaminomethoxy group, methylcarbonylaminoethoxy group, ethylcarbonylaminoethoxy group, methoxycarbonylmethoxy group, trifluoromethoxycarbonylmethoxy group, ethoxycarbonylmethoxy group, methoxycarbonylethoxy group, ethoxycarbonylethoxy group, methylamino group, trifluoromethylamino group, ethylamino group, n-propylamino group, i-propylamino group, n-butylamino group, dimethylamino group, di-(trifluoromethyl)amino group, diethylamino group, di-n-propylamino group, di-i-propylamino group, di-n-butylamino group, methylcarbonylamino group, trifluoromethylcarbonylamino group, ethylcarbonylamino group, n-propylcarbonylamino group, i-propylcarbonylamino group, n-butylcarbonylamino group, methanesulfonamide group, trifluoromethanesulfonamide group, ethanesulfonamide group, n-propanesulfonamide group, i-propanesulfonamide group, n-butanesulfonamide group, benzenesulfonamide group, p-toluenesulfonamide group, methylaminocarbonyl group, trifluoromethylaminocarbonyl group, ethyaminocarbonyl group, n-propylaminocarbonyl group, i-propylaminocarbonyl group, n-butylaminocarbonyl group, dimethylaminocarbonyl group, di-(trifluoromethyl)aminocarbonyl group, diethylaminocarbonyl group, di-n-propylaminocarbonyl, di-i-propylaminocarbonyl group, di-c-propylaminocarbonyl group, di-n-butylaminocarbonyl group, methyl(ethyl)aminocarbonyl group, trifluoromethyl(ethyl)aminocarbonyl group, methylcarbonyl group, trifluoromethylcarbonyl group, ethycarbonyl group, n-propylcarbonyl group, i-propylcarbonyl group, n-butylcarbonyl group, methoxycarbonyl group, trifluoromethoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, methanesulfonyl group, trifluoromethanesulfonyl group, ethanesulfonyl group, benzenesulfonyl group, o-biphenylsulfonyl group, m-biphenylsulfonyl group, p-biphenylsulfonyl group, 1-naphthalenesulfonyl group, 2-naphthalenesulfonyl group, phenylcarbonyl group, o-biphenylylcarbonyl group, m-biphenylylcarbonyl group, p-biphenylylcarbonyl group, 1-naphthylcarbonyl group, 2-naphthylcarbonyl group, hydroxy group, nitro group, cyano group, formyl group, formamide group, carbamoyl group, sulfoamino group, sulfamoyl group, amino group and carboxyl group.

Each substitution group of $R^{12}$, $R^{13}$, $R^{14}$, $R^{15}$, $R^{16}$ and $R^{17}$ in the formula (a), formula (b), formula (c), formula (d), formula (e), formula (f), formula (g), formula (h), formula (i), formula (j), formula (k), formula (l), formula (m), formula (n), formula (o), formula (p), formula (q), formula (r), formula (s), formula (t), formula (u), formula (v), formula (w), formula (x), formula (y), formula (z), formula (aa), formula (ab), formula (ac), formula (ad), formula (ae), formula (af), formula (ag), and formula (ah) will be described,

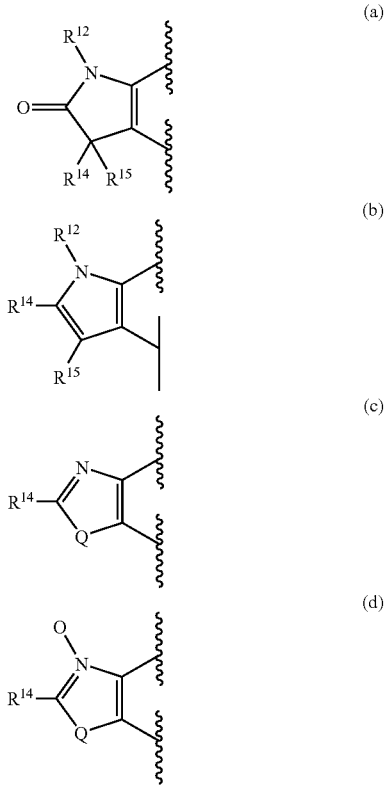

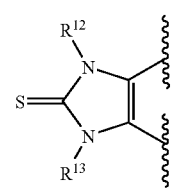(e)
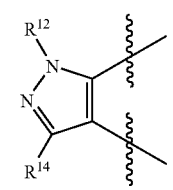(f)
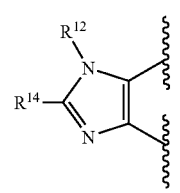(g)
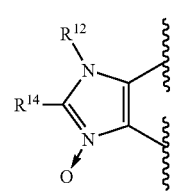(h)
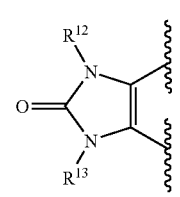(i)
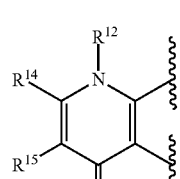(j)
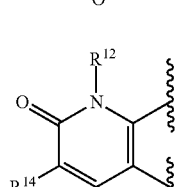(k)
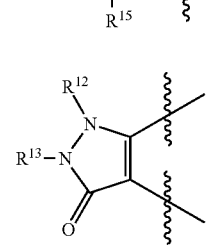(l)
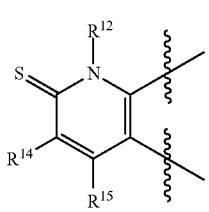(m)
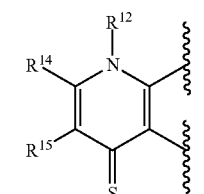(n)
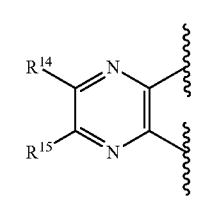(o)
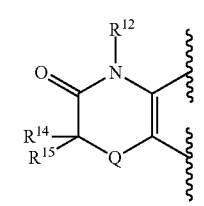(p)
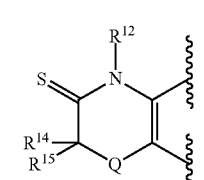(q)
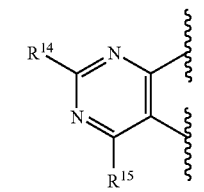(r)
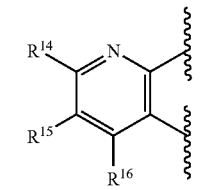(s)
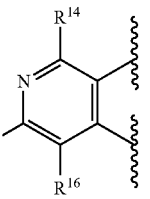(t)

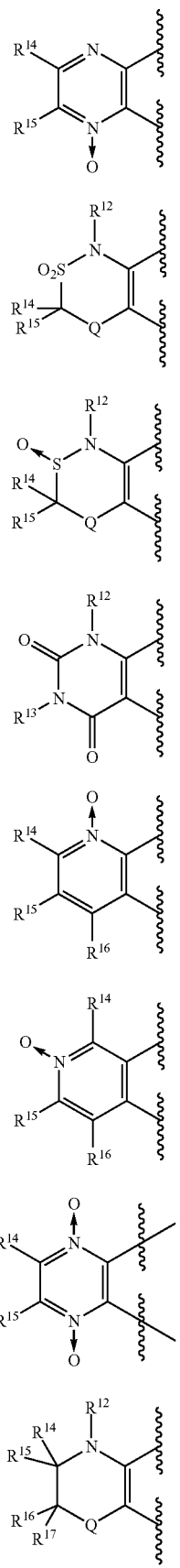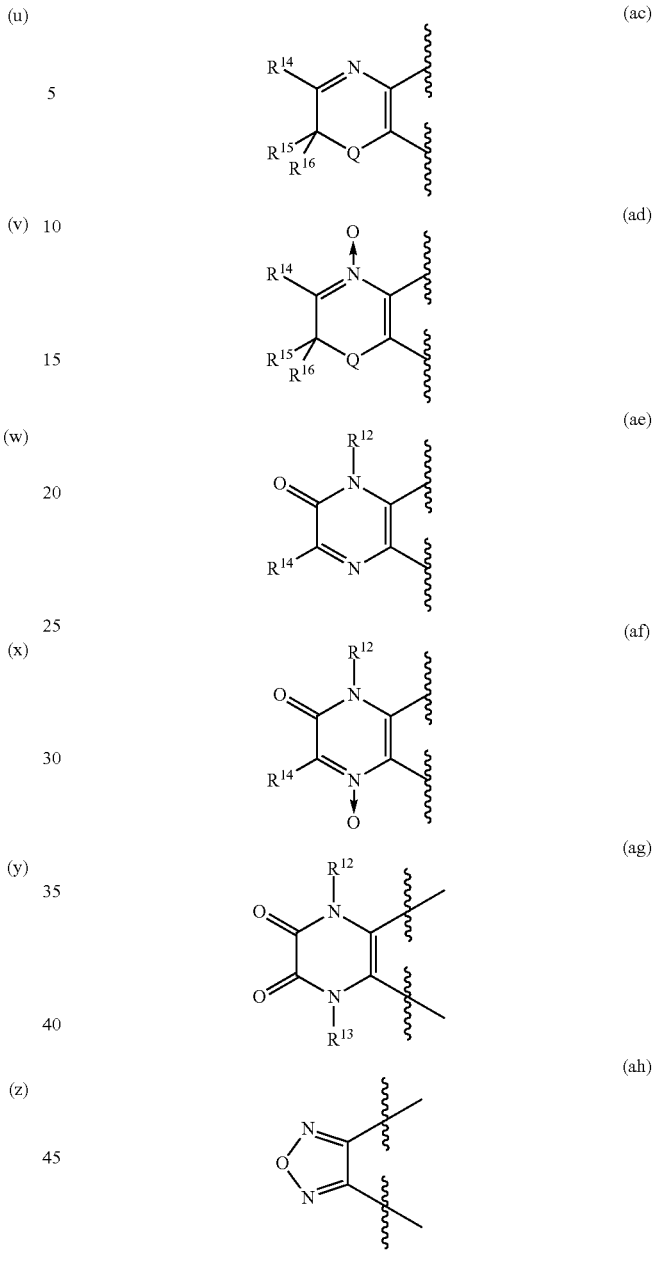

in which partial ring structure A in the formula (11) and formula (12) is represented by the formula (a), formula (b), formula (c), formula (d), formula (e), formula (f), formula (g), formula (h), formula (i), formula (j), formula (k), formula (l), formula (m), formula (n), formula (o), formula (p), formula (q), formula (r), formula (s), formula (t), formula (u), formula (v), formula (w), formula (x), formula (y), formula (z), formula (aa), formula (ab), formula (ac), formula (ad), formula (ae), formula (af), formula (ag), and formula (ah).

First, $R^{12}$ and $R^{13}$ in the formula (a), formula (b), formula (e), formula (f), formula (g), formula (h), formula (i), formula (j), formula (k), formula (l), formula (m), formula (n), formula (p), formula (q), formula (v), formula (w), formula (x), formula (ab), formula (ae), formula (af) and formula (ag) will be described.

$R^{12}$ and $R^{13}$ in the formula (a), formula (b), formula (e), formula (f), formula (g), formula (h), formula (i), formula (j), formula (k), formula (l), formula (m), formula (n), formula (p), formula (q), formula (v), formula (w), formula (x), formula (ab), formula (ae), formula (af) and formula (ag) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group or $C_{2-9}$ heteroaryl group (any of the aryl group and heteroaryl group may be optionally substituted with q $R^{18}$ ($R^{18}$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom) or may be optionally substituted with a $C_{2-9}$ heteroarylcarbonyl group), $C_{6-14}$ aryl group, $C_{2-9}$ heteroaryl group (the aryl group and heteroaryl group may be optionally substituted with q $R^{18}$ ($R^{18}$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, $C_{6-14}$ arylsulfonyl group, $C_{2-9}$ heteroarylsulfonyl group (the arylsulfonyl group and heteroarylsulfonyl group may be optionally substituted with q $R^{18}$ ($R^{18}$ represents the same meaning of $R^{11}$; q represents an integer of 1 to 3, and each $R^{18}$ may be the same or different when q is 2 or 3)), carboxyl group, $C_{6-14}$ arylcarbonyl group, or $C_{2-9}$ heteroarylcarbonyl group (the arylcarbonyl group and heteroarylcarbonyl group may be optionally substituted with q $R^{18}$ ($R^{18}$ represents the same meaning of $R^{11}$; q represents an integer of 1 to 3, and each $R^{18}$ may be the same or different when q is 2 or 3)).

Each substitution group of $R^{12}$ and $R^{13}$ in the formula (a), formula (b), formula (e), formula (f), formula (g), formula (h), formula (i), formula (j), formula (k), formula (l), formula (m), formula (n), formula (p), formula (q), formula (v), formula (w), formula (x), formula (ab), formula (ae), formula (af) and formula (ag) will be specifically described.

Examples of the $C_{1-6}$ alkyl group include a methyl group, trifluoromethyl group, ethyl group, n-propyl group, i-propyl group, n-butyl group, i-butyl group, s-butyl group, t-butyl group, n-pentyl group, 2-pentyl group, 3-pentyl group, i-pentyl group, neopentyl group, 2,2-dimethylpropyl group, n-hexyl group, 2-hexyl group, 3-hexyl group, 1-methyl-n-pentyl group, 1,1,2-trimethyl-n-propyl group, 1,2,2-trimethyl-n-propyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, trifluoromethylcarbonylaminomethyl group, ethylcarbonylaminomethyl group, methylcarbonylaminoethyl group, ethylcarbonylaminoethyl group, methoxycarbonylmethyl group, ethoxycarbonylmethyl group, methoxycarbonylethyl group and ethoxycarbonylethyl group; and examples of the $C_{6-14}$ aryl group include a phenyl group, o-biphenylyl group, m-biphenylyl group, p-biphenylyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group and 9-phenanthryl group.

Examples of the $C_{2-9}$ heteroaryl group include $C_{2-6}$ monocyclic heterocyclic group having up to 5- to 7-membered ring which can contain 1 to 3 oxygen atom(s), nitrogen atom(s), sulfur atom(s) and a combination thereof and $C_{5-9}$ fused bicyclic heterocyclic group having up to 8 to 10 of constituent atoms.

Examples of the $C_{2-6}$ monocyclic heterocyclic group of up to 5 to 7 membered ring include a 2-thienyl group, 3-thienyl group, 2-furyl group, 3-furyl group, 2-pyranyl group, 3-pyranyl group, 4-pyranyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isoxazolyl group, 4-isoxazolyl group, 5-isoxazolyl group, 2-pyridyl group, 3-pyridyl group, 4-pyridyl group, 2-pyradinyl group, 2-pyrimidinyl group, 4-pyrimidinyl group, 5-pyrimidinyl group, 3-pyridazinyl group, 4-pyridazinyl group, 2-1,3,4-oxadiazolyl group, 2-1,3,4-thiadiazolyl group, 3-1,2,4-oxadiazolyl group, 5-1,2,4-oxadiazolyl group, 3-1,2,4-thiadiazolyl group, 5-1,2,4-thiadiazolyl group, 3-1,2,5,-oxadiazolyl group and 3-1,2,5-thiadiazolyl group; and examples of the $C_{5-9}$ fused bicyclic heterocyclic group having up to 8 to 10 of constituent atoms include a 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromenyl group, 4-chromenyl group, 5-chromenyl group, 6-chromenyl group, 7-chromenyl group, 8-chromenyl group, 1-indolidinyl group, 2-indolidinyl group, 3-indolidinyl group, 5-indolidinyl group, 6-indolidinyl group, 7-indolidinyl group, 8-indolidinyl group, 1-isoindolyl group, 2-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 1-purinyl group, 2-purinyl group, 3-purinyl group, 6-purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthaladinyl group, 5-phthaladinyl group, 6-phthaladinyl group, 1-2,7-naphthyridinyl group, 3-2,7-naphthyridinyl group, 4-2,7-naphthyridinyl group, 1-2,6-naphthyridinyl group, 3-2,6-naphthyridinyl group, 4-2,6-naphthyridinyl group, 2-1,8-naphthyridinyl group, 3-1,8-naphthyridinyl group, 4-1,8-naphthyridinyl group, 2-1,7-naphthyridinyl group, 3-1,7-naphthyridinyl group, 4-1,7-naphthyridinyl group, 5-1,7-naphthyridinyl group, 6-1,7-naphthyridinyl group, 8-1,7-naphthyridinyl group, 2-1,6-naphthyridinyl group, 3-1,6-naphthyridinyl group, 4-1,6-naphthyridinyl group, 5-1,6-naphthyridinyl group, 7-1,6-naphthyridinyl group, 8-1,6-naphthyridinyl group, 2-1,5-naphthyridinyl group, 3-1,5-naphthyridinyl group, 4-1,5-naphthyridinyl group, 6-1,5-naphthyridinyl group, 7-1,5-naphthyridinyl group, 8-1,5-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group and 7-pteridinyl group.

Examples of the $C_{1-6}$ alkylaminocarbonyl group include a methylaminocarbonyl group, ethylaminocarbonyl group, n-propylaminocarbonyl group, i-propylaminocarbonyl group, n-butylaminocarbonyl group, i-butylaminocarbonyl group, s-butylaminocarbonyl group, t-butylaminocarbonyl group, 1-pentylaminocarbonyl group, 2-pentylaminocarbonyl group, 3-pentylaminocarbonyl group, i-pentylaminocarbonyl group, neopentylaminocarbonyl, t-pentylaminocarbonyl group, 1-hexylaminocarbonyl group, 2-hexylaminocarbonyl group and 3-hexylaminocarbonyl group;

examples of the di-$C_{1-6}$ alkylaminocarbonyl group include a dimethylaminocarbonyl group, diethylaminocarbonyl group, di-n-propylaminocarbonyl, di-i-propylaminocarbonyl group, di-c-propylaminocarbonyl group, di-n-butylaminocarbonyl group, di-i-butylaminocarbonyl group, di-s-butylaminocarbonyl group, di-t-butylaminocarbonyl group, di-c-butylaminocarbonyl group, di-1-pentylaminocarbonyl group, di-2-pentylaminocarbonyl group, di-3-pentylaminocarbonyl group, di-1-pentylaminocarbonyl group, di-neopentylaminocarbonyl group, di-t-pentylaminocarbonyl group, di-c-pentylaminocarbonyl group, di-1-hexylaminocarbonyl group, di-2-hexylaminocarbonyl group, di-3-hexylaminocarbonyl group, di-c-hexylaminocarbonyl group, di-(1-methyl-n-pentyl)aminocarbonyl group, di-(1,1,2-trimethyl-n-propyl)aminocarbonyl group, di-(1,2,2-trimethyl-n-propyl)aminocarbonyl group, di-(3,3-dimethyl-n-butyl)aminocarbonyl group, methyl(ethyl)aminocarbonyl group, methyl(n-propyl)aminocarbonyl group, methyl(i-propyl)aminocarboriyl group, methyl(c-propyl)aminocarbonyl group, methyl(n-butyl)aminocarbonyl group, methyl(i-butyl) aminocarbonyl group, methyl(s-butyl)aminocarbonyl group, methyl(t-butyl)aminocarbonyl group, methyl(c-butyl)aminocarbonyl group, ethyl(n-propyl)aminocarbonyl group, ethyl(i-propyl)aminocarbonyl group, ethyl(c-propyl)aminocarbonyl group, ethyl(n-butyl)aminocarbonyl group, ethyl (i-butyl)aminocarbonyl group, ethyl(s-butyl)aminocarbonyl group, ethyl(t-butyl)aminocarbonyl group, ethyl(c-butyl) aminocarbonyl group, n-propyl(i-propyl)aminocarbonyl group, n-propyl(c-propyl)aminocarbonyl group, n-propyl(n-butyl)aminocarbonyl group, n-propyl(i-butyl)aminocarbonyl group, n-propyl(s-butyl)aminocarbonyl group, n-propyl(t-butyl)aminocarbonyl group, n-propyl(c-butyl)aminocarbonyl group, i-propyl(c-propyl)aminocarbonyl group, i-propyl (n-butyl)aminocarbonyl group, i-propyl(i-butyl) aminocarbonyl group, i-propyl(s-butyl)aminocarbonyl group, i-propyl(t-butyl)aminocarbonyl group, i-propyl(c-butyl)aminocarbonyl group, c-propyl(n-butyl)aminocarbonyl group, c-propyl(i-butyl)aminocarbonyl group, c-propyl(s-butyl)aminocarbonyl group, c-propyl(t-butyl)aminocarbonyl group, c-propyl(c-butyl)aminocarbonyl group, n-butyl(i-butyl)aminocarbonyl group, n-butyl(s-butyl)aminocarbonyl group, n-butyl(t-butyl)aminocarbonyl group, n-butyl(c-butyl)aminocarbonyl group, i-butyl(s-butyl)aminocarbonyl group, i-butyl(t-butyl)aminocarbonyl group, i-butyl(c-butyl) aminocarbonyl group, s-butyl(t-butyl)aminocarbonyl group, s-butyl(c-butyl)aminocarbonyl group and t-butyl(c-butyl) aminocarbonyl group;

examples of the $C_{1-6}$ alkylcarbonyl group include a methylcarbonyl group, ethylcarbonyl group, n-propylcarbonyl group, i-propylcarbonyl group, n-butylcarbonyl group, i-butylcarbonyl group, s-butylcarbonyl group, t-butylcarbonyl group, 1-pentylcarbonyl group, 2-pentylcarbonyl group, 3-pentylcarbonyl group, i-pentylcarbonyl group, neopentylcarbonyl group, t-pentylcarbonyl group, 1-hexylcarbonyl group, 2-hexylcarbonyl group and 3-hexylcarbonyl group;

examples of the $C_{3-8}$ cycloalkylcarbonyl group include a c-propylcarbonyl group, c-butylcarbonyl group, 1-methyl-c-propylcarbonyl group, 2-methyl-c-propylcarbonyl group, c-pentylcarbonyl group, 1-methyl-c-butylcarbonyl group, 2-methyl-c-butylcarbonyl group, 3-methyl-c-butylcarbonyl group, 1,2-dimethyl-c-propylcarbonyl group, 2,3-dimethyl-c-propylcarbonyl group, 1-ethyl-c-propylcarbonyl group, 2-ethyl-c-propylcarbonyl group, c-hexylcarbonyl group, c-heptylcarbonyl group, c-octylcarbonyl group, 1-methyl-c-hexylcarbonyl group, 2-methyl-c-hexylcarbonyl group, 3-methyl-c-hexylcarbonyl group, 1,2-dimethyl-c-hexylcarbonyl group, 2,3-dimethyl-c-propylcarbonyl group, 1-ethyl-c-propylcarbonyl group, 1-methyl-c-pentylcarbonyl group, 2-methyl-c-pentylcarbonyl group, 3-methyl-c-pentylcarbonyl group, 1-ethyl-c-butylcarbonyl group, 2-ethyl-c-butylcarbonyl group, 3-ethyl-c-butylcarbonyl group, 1,2-dimethyl-c-butylcarbonyl group, 1,3-dimethyl-c-butylcarbonyl group, 2,2-dimethyl-c-butylcarbonyl group, 2,3-dimethyl-c-butylcarbonyl group, 2,4-dimethyl-c-butylcarbonyl group, 3,3-dimethyl-c-butylcarbonyl group, 1-n-propyl-c-propylcarbonyl group, 2-n-propyl-c-propylcarbonyl group, 1-i-propyl-c-propylcarbonyl group, 2-i-propyl-c-propylcarbonyl group, 1,2,2-trimethyl-c-propylcarbonyl group, 1,2,3-trimethyl-c-propylcarbonyl group, 2,2,3-trimethyl-c-propylcarbonyl group, 1-ethyl-2-methyl-c-propylcarbonyl group, 2-ethyl-1-methyl-c-propylcarbonyl group, 2-ethyl-2-methyl-c-propylcarbonyl group and 2-ethyl-3-methyl-c-propylcarbonyl group;

examples of the $C_{1-6}$ alkoxycarbonyl group include a methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, 1-pentyloxycarbonyl group, 2-pentyloxycarbonyl group, 3-pentyloxycarbonyl group, i-pentyloxycarbonyl group, neopentyloxycarbonyl group, t-pentyloxycarbonyl group, 1-hexyloxycarbonyl group, 2-hexyloxycarbonyl group and 3-hexyloxycarbonyl group;

examples of the $C_{1-6}$ alkylsulfonyl group include a methanesulfonyl group, trifluoromethanesulfonyl group and ethanesulfonyl group; and examples of the $C_{6-14}$ arylsulfonyl group include a benzenesulfonyl group, o-biphenylsulfonyl group, m-biphenylsulfonyl group, p-biphenylsulfonyl group, 1-naphthalenesulfonyl group, 2-naphthalenesulfonyl group, 1-anthracenesulfonyl group, 2-anthracenesulfonyl group, 9-anthracenesulfonyl group, 1-phenanthrenesulfonyl group, 2-phenanthrenesulfonyl group, 3-phenanthrenesulfonyl group, 4-phenanthrenesulfonyl group and 9-phenanthrenesulfonyl group.

Examples of the $C_{2-9}$ heteroarylsulfonyl group include a $C_{2-6}$ monocyclic heterocyclic sulfonyl group of up to 5- to 7-membered ring which can contain 1 to 3 oxygen atom(s), nitrogen atom(s), sulfur atom(s) and a combination thereof and $C_{5-9}$ fused bicyclic heterocyclic sulfonyl group having up to 8 to 10 of constituent atoms.

Examples of the $C_{2-6}$ monocyclic heterocyclic sulfonyl group of up to 5- to 7-membered ring include a 2-thienylsulfonyl group, 3-thienylsulfonyl group, 2-furylsulfonyl group, 3-furylsulfonyl group, 2-pyranylsulfonyl group, 3-pyranylsulfonyl group, 4-pyranylsulfonyl group, 1-pyrrolylsulfonyl group, 2-pyrrolylsulfonyl group, 3-pyrrolylsulfonyl group, 1-imidazolylsulfonyl group, 2-imidazolylsulfonyl group, 4-imidazolylsulfonyl group, 1-pyrazolylsulfonyl group, 3-pyrazolylsulfonyl group, 4-pyrazolylsulfonyl group, 2-thiazolylsulfonyl group, 4-thiazolylsulfonyl group, 5-thiazolylsulfonyl group, 3-isothiazolylsulfonyl group, 4-isothiazolylsulfonyl group, 5-isothiazolylsulfonyl group, 2-oxazolylsulfonyl group, 4-oxazolylsulfonyl group, 5-oxazolylsulfonyl group, 3-isoxazolylsulfonyl group, 4-isoxazolylsulfonyl group, 5-isoxazolylsulfonyl group, 2-pyridylsulfonyl group, 3-pyridylsulfonyl group, 4-pyridylsulfonyl group, 2-pyradinylsulfonyl group, 2-pyrimidinylsulfonyl group, 4-pyrimidinylsulfonyl group, 5-pyrimidinylsulfonyl group, 3-pyridazinylsulfonyl group, 4-pyridazinylsulfonyl group, 2-1,3,4-oxadiazolylsulfonyl group, 2-1,3,4-thiadiazolylsulfonyl group, 3-1,2,4-oxadiazolylsulfonyl group, 5-1,2,4-oxadiazolylsulfonyl group, 3-1,2,4-thiadiazolylsulfonyl group, 5-1,2,4-thiadiazolylsulfonyl group, 3-1,2,5,-oxadiazolylsulfonyl group and 3-1,2,5-thiadiazolylsulfonyl group.

Examples of the $C_{5-9}$ fused bicyclic heterocycle sulfonyl group having up to 8 to 10 of constituent atoms include a 2-benzofuranylsulfonyl group, 3-benzofuranylsulfonyl group, 4-benzofuranylsulfonyl group, 5-benzofuranylsulfonyl group, 6-benzofuranylsulfonyl group, 7-benzofuranylsulfonyl group, 1-isobenzofuranylsulfonyl group, 4-isobenzofuranylsulfonyl group, 5-isobenzofuranylsulfonyl group, 2-benzothienylsulfonyl group, 3-benzothienylsulfonyl group, 4-benzothienylsulfonyl group, 5-benzothienylsulfonyl group, 6-benzothienylsulfonyl group, 7-benzothienylsulfonyl group, 1-isobenzothienylsulfonyl group, 4-isobenzothienylsulfonyl group, 5-isobenzothienylsulfonyl group, 2-chromenylsulfonyl group, 3-chromenylsulfonyl group, 4-chromenylsulfonyl group, 5-chromenylsulfonyl group, 6-chromenylsulfonyl group, 7-chromenylsulfonyl group, 8-chromenylsulfonyl group, 1-indolidinylsulfonyl group, 2-indolidinylsulfonyl group, 3-indolidinylsulfonyl group, 5-indolidinylsulfonyl group, 6-indolidinylsulfonyl group, 7-indolidinylsulfonyl group, 8-indolidinylsulfonyl group, 1-isoindolylsulfonyl group, 2-isoindolylsulfonyl group, 4-isoindolylsulfonyl group, 5-isoindolylsulfonyl group, 1-indolylsulfonyl group, 2-indolylsulfonyl group, 3-indolylsulfonyl group, 4-indolylsulfonyl group, 5-indolylsulfonyl group, 6-indolylsulfonyl group, 7-indolylsulfonyl group, 1-indazolylsulfonyl group, 2-indazolylsulfonyl group, 3-indazolylsulfonyl group, 4-indazolylsulfonyl group, 5-indazolylsulfonyl group, 6-indazolylsulfonyl group, 7-indazolylsulfonyl group, 1-purinylsulfonyl group, 2-purinylsulfonyl group, 3-purinylsulfonyl group, 6-purinylsulfonyl group, 7-purinylsulfonyl group, 8-purinylsulfonyl group, 2-quinolylsulfonyl group, 3-quinolylsulfonyl group, 4-quinolylsulfonyl group, 5-quinolylsulfonyl group, 6-quinolylsulfonyl group, 7-quinolylsulfonyl group, 8-quinolylsulfonyl group, 1-isoquinolylsulfonyl group, 3-isoquinolylsulfonyl group, 4-isoquinolylsulfonyl group, 5-isoquinolylsulfonyl group, 6-isoquinolylsulfonyl group, 7-isoquinolylsulfonyl group, 8-isoquinolylsulfonyl group, 1-phthaladinylsulfonyl group, 5-phthaladinylsulfonyl group, 6-phthaladinylsulfonyl group, 1-2,7-naphthyridinylsulfonyl group, 3-2,7-naphthyridinylsulfonyl group, 4-2,7-naphthyridinylsulfonyl group, 1-2,6-naphthyridinylsulfonyl group, 3-2,6-naphthyridinylsulfonyl group, 4-2,6-naphthyridinylsulfonyl group, 2-1,8-naphthyridinylsulfonyl group, 3-1,8-naphthyridinylsulfonyl group, 4-1,8-naphthyridinylsulfonyl group, 2-1,7-naphthyridinylsulfonyl group, 3-1,7-naphthyridinylsulfonyl group, 4-1,7-naphthyridinylsulfonyl group, 5-1,7-naphthyridinylsulfonyl group, 6-1,7-naphthyridinylsulfonyl group, 8-1,7-naphthyridinylsulfonyl group, 2-1,6-naphthyridinylsulfonyl group, 3-1,6-naphthyridinylsulfonyl group, 4-1,6-naphthyridinylsulfonyl group, 5-1,6-naphthyridinylsulfonyl group, 7-1,6-naphthyridinylsulfonyl group, 8-1,6-naphthyridinylsulfonyl group, 2-1,5-naphthyridinylsulfonyl group, 3-1,5-naphthyridinylsulfonyl group, 4-1,5-naphthyridinylsulfonyl group, 6-1,5-naphthyridinylsulfonyl group, 7-1,5-naphthyridinylsulfonyl group, 8-1,5-naphthyridinylsulfonyl group, 2-quinoxalinylsulfonyl group, 5-quinoxalinylsulfonyl group, 6-quinoxalinylsulfonyl group, 2-quinazolinylsulfonyl group, 4-quinazolinylsulfonyl group, 5-quinazolinylsulfonyl group, 6-quinazolinylsulfonyl group, 7-quinazolinylsulfonyl group, 8-quinazolinylsulfonyl group, 3-cinnolinylsulfonyl group, 4-cinnolinylsulfonyl group, 5-cinnolinylsulfonyl group, 6-cinnolinylsulfonyl group, 7-cinnolinylsulfonyl group, 8-cinnolinylsulfonyl group, 2-pteridinylsulfonyl group, 4-pteridinylsulfonyl group, 6-pteridinylsulfonyl group and 7-pteridinylsulfonyl group.

Examples of the $C_{6-14}$ arylcarbonyl group include a phenylcarbonyl group, o-biphenylylcarbonyl group, m-biphenylylcarbonyl group, p-biphenylylcarbonyl group, 1-naphthylcarbonyl group, 2-naphthylcarbonyl group, 1-anthrylcarbonyl group, 2-anthrylcarbonyl group, 9-anthrylcarbonyl group, 1-phenanthrylcarbonyl group, 2-phenanthrylcarbonyl group, 3-phenanthrylcarbonyl group, 4-phenanthrylcarbonyl group and 9-phenanthrylcarbonyl group.

Examples of the $C_{2-9}$ heteroarylcarbonyl group include a $C_{2-6}$ monocyclic heterocyclic carbonyl group of up to 5- to 7-membered ring which can contain 1 to 3 oxygen atom(s), nitrogen atom(s), sulfur atom(s) and a combination thereof and $C_{5-9}$ fused bicyclic heterocyclic carbonyl group having up to 8 to 10 of constituent atoms.

Examples of the $C_{2-6}$ monocyclic heterocyclic carbonyl group of up to 5- to 7-membered ring include a 2-thienylcarbonyl group, 3-thienylcarbonyl group, 2-furylcarbonyl group, 3-furylcarbonyl group, 2-pyranylcarbonyl group, 3-pyranylcarbonyl group, 4-pyranylcarbonyl group, 1-pyrrolylcarbonyl group, 2-pyrrolylcarbonyl group, 3-pyrrolylcarbonyl group, 1-imidazolylcarbonyl group, 2-imidazolylcarbonyl group, 4-imidazolylcarbonyl group, 1-pyrazolylcarbonyl group, 3-pyrazolylcarbonyl group, 4-pyrazolylcarbonyl group, 2-thiazolylcarbonyl group, 4-thiazolylcarbonyl group, 5-thiazolylcarbonyl group, 3-isothiazolylcarbonyl group, 4-isothiazolylcarbonyl group, 5-isothiazolylcarbonyl group, 2-oxazolylcarbonyl group, 4-oxazolylcarbonyl group, 5-oxazolylcarbonyl group, 3-isoxazolylcarbonyl group, 4-isoxazolylcarbonyl group, 5-isoxazolylcarbonyl group, 2-pyridylcarbonyl group, 3-pyridylcarbonyl group, 4-pyridylcarbonyl group, 2-pyradinylcarbonyl group, 2-pyrimidinylcarbonyl group, 4-pyrimidinylcarbonyl group, 5-pyrimidinylcarbonyl group, 3-pyridazinylcarbonyl group, 4-pyridazinylcarbonyl group, 2-1,3,4-oxadiazolylcarbonyl group, 2-1,3,4-thiadiazolylcarbonyl group, 3-1,2,4-oxadiazolylcarbonyl group, 5-1,2,4-oxadiazolylcarbonyl group, 3-1,2,4-thiadiazolylcarbonyl group, 5-1,2,4-thiadiazolylcarbonyl group, 3-1,2,5,-oxadiazolylcarbonyl group and 3-1,2,5-thiadiazolylcarbonyl group.

Examples of the $C_{5-9}$ fused bicyclic heterocyclic carbonyl group having up to 8 to 10 of constituent atoms include a 2-benzofuranylcarbonyl group, 3-benzofuranylcarbonyl group, 4-benzofuranylcarbonyl group, 5-benzofuranylcarbonyl group, 6-benzofuranylcarbonyl group, 7-benzofuranylcarbonyl group, 1-isobenzofuranylcarbonyl group, 4-isobenzofuranylcarbonyl group, 5-isobenzofuranylcarbonyl group, 2-benzothienylcarbonyl group, 3-benzothienylcarbonyl group, 4-benzothienylcarbonyl group, 5-benzothienylcarbonyl group, 6-benzothienylcarbonyl group, 7-benzothienylcarbonyl group, 1-isobenzothienylcarbonyl group, 4-isobenzothienylcarbonyl group, 5-isobenzothienylcarbonyl group, 2-chromenylcarbonyl group, 3-chromenylcarbonyl group, 4-chromenylcarbonyl group, 5-chromenylcarbonyl group, 6-chromenylcarbonyl group, 7-chromenylcarbonyl group, 8-chromenylcarbonyl group, 1-indolidinylcarbonyl group, 2-indolidinylcarbonyl group, 3-indolidinylcarbonyl group, 5-indolidinylcarbonyl group, 6-indolidinylcarbonyl group, 7-indolidinylcarbonyl group, 8-indolidinylcarbonyl group, 1-isoindolylcarbonyl group, 2-isoindolylcarbonyl group, 4-isoindolylcarbonyl group, 5-isoindolylcarbonyl group, 1-indolylcarbonyl group, 2-indolylcarbonyl group, 3-indolylcarbonyl group, 4-indolylcarbonyl group, 5-indolylcarbonyl group, 6-indolylcarbonyl group, 7-indolylcarbonyl group, 1-indazolylcarbonyl group, 2-indazolylcarbonyl group, 3-indazolylcarbonyl group, 4-indazolylcarbonyl group, 5-indazolylcarbonyl group, 6-indazolylcarbonyl group, 7-indazolylcarbonyl group, 1-purinylcarbonyl group, 2-purinylcarbonyl group, 3-purinylcarbonyl group, 6-purinylcarbonyl group, 7-purinylcarbonyl group, 8-purinylcarbonyl group, 2-quinolylcarbonyl group, 3-quinolylcarbonyl group, 4-quinolylcarbonyl group, 5-quinolylcarbonyl group, 6-quinolylcarbonyl group, 7-quinolylcarbonyl group, 8-quinolylcarbonyl group, 1-isoquinolylcarbonyl group, 3-isoquinolylcarbonyl group, 4-isoquinolylcarbonyl group, 5-isoquinolylcarbonyl group, 6-isoquinolylcarbonyl group, 7-isoquinolylcarbonyl group, 8-isoquinolylcarbonyl group, 1-phthaladinylcarbonyl group, 5-phthaladinylcarbonyl group, 6-phthaladinylcarbonyl group, 1-2,7-naphthyridinylcarbonyl group, 3-2,7-naphthyridinylcarbonyl group, 4-2,7-naphthyridinylcarbonyl group, 1-2,6-naphthyridinylcarbonyl group, 3-2,6-naphthyridinylcarbonyl group, 4-2,6-naphthyridinylcarbonyl group, 2-1,8-naphthyridinylcarbonyl group, 3-1,8-naphthyridinylcarbonyl group, 4-1,8-naphthyridinylcarbonyl group, 2-1,7-naphthyridinylcarbonyl group, 3-1,7-naphthyridinylcarbonyl group, 4-1,7-naphthyridinylcarbonyl group, 5-1,7-naphthyridinylcarbonyl group, 6-1,7-naphthyridinylcarbonyl group, 8-1,7-naphthyridinylcarbonyl group, 2-1,6-naphthyridinylcarbonyl group, 3-1,6-naphthyridinylcarbonyl group, 4-1,6-naphthyridinylcarbonyl group, 5-1,6-naphthyridinylcarbonyl group, 7-1,6-naphthyridinylcarbonyl group, 8-1,6-naphthyridinylcarbonyl group, 2-1,5-naphthyridinylcarbonyl group, 3-1,5-naphthyridinylcarbonyl group, 4-1,5-naphthyridinylcarbonyl group, 6-1,5-naphthyridinylcarbonyl group, 7-1,5-naphthyridinylcarbonyl group, 8-1,5-naphthyridinylcarbonyl group, 2-quinoxalinylcarbonyl group, 5-quinoxalinylcarbonyl group, 6-quinoxalinylcarbonyl group, 2-quinazolinylcarbonyl group, 4-quinazolinylcarbonyl group, 5-quinazolinylcarbonyl group, 6-quinazolinylcarbonyl group, 7-quinazolinylcarbonyl group, 8-quinazolinylcarbonyl group, 3-cinnolinylcarbonyl group, 4-cinnolinylcarbonyl group, 5-cinnolinylcarbonyl group, 6-cinnolinylcarbonyl group, 7-cinnolinylcarbonyl group, 8-cinnolinylcarbonyl group, 2-pteridinylcarbonyl group, 4-pteridinylcarbonyl group, 6-pteridinylcarbonyl group and 7-pteridinylcarbonyl group.

$R^{12}$ and $R^{13}$ in the formula (a), formula (b), formula (e), formula (f), formula (g), formula (h), formula (i), formula (j), formula (k), formula (l), formula (m), formula (n), formula (p), formula (q), formula (v), formula (w), formula (x), formula (ab), formula (ae), formula (af) and formula (ag) are preferably hydrogen atom, methyl group, ethyl group, n-propyl group, i-propyl group, n-butyl group, n-pentyl group, i-pentyl group, methylcarbonyloxymethyl group, ethylcarbonyloxymethyl group, methylcarbonyloxyethyl group, ethylcarbonyloxyethyl group, methylcarbonylaminomethyl group, ethylcarbonylaminoethyl group, methylcarbonylaminoethyl group, ethylcarbonylaminoethyl group, methoxycarbonylmethyl group, ethoxycarbonylmethyl group, methoxycarbonylethyl group, ethoxycarbonylethyl group, phenyl group, o-biphenylyl group, m-biphenylyl group, p-biphenylyl group, 1-naphthyl group, 2-naphthyl group, 2-pyridyl group, 3-pyridyl group, 4-pyridyl group, methylaminocarbonyl group, ethyaminocarbonyl group, n-propylaminocarbonyl group, i-propylaminocarbonyl group, n-butylaminocarbonyl group, dimethylaminocarbonyl group, diethylaminocarbonyl group, di-n-propylaminocarbonyl group, di-i-propylaminocarbonyl group, di-c-propylaminocarbonyl group, di-n-butylaminocarbonyl group, methylcarbonyl group, ethycarbonyl group, n-propylcarbonyl group, i-propylcarbonyl group, n-butylcarbonyl group, c-pentylcarbonyl group, c-hexylcarbonyl group, methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, methanesulfonyl group, trifluoromethanesulfonyl group, benzenesulfonyl group, o-biphenylsulfonyl group, m-biphenylsulfonyl group, p-biphenylsulfonyl group, 1-naphthalenesulfonyl group, 2-naphthalenesulfonyl group, 2-pyridylsulfonyl group, 3-pyridylsulfonyl group, 4-pyridylsulfonyl group, phenylcarbonyl group, o-biphenylylcarbonyl group, m-biphenylylcarbonyl group, p-biphenylylcarbonyl group, 1-naphthylcarbonyl group, 2-naphthylcarbonyl group, 2-pyridylcarbonyl group, 3-pyridylcarbonyl and 4-pyridylcarbonyl and more preferably hydrogen atom and methyl group.

Then, $R^{14}$, $R^{15}$, $R^{16}$ and $R^{17}$ in the formula (a), formula (b), formula (c), formula (d), formula (f), formula (g), formula (h), formula (j), formula (k), formula (m), formula (n), formula (o), formula (p), formula (q), formula (r), formula (s), formula (t), formula (u), formula (v), formula (w), formula (y), formula (z), formula (aa), formula (ab), formula (ac), formula (ad), formula (ae) and formula (af) will be described. $R^{14}$, $R^{15}$, $R^{16}$ and $R^{17}$ in the formula (a), formula (b), formula (c), formula (d), formula (f), formula (g), formula (h), formula (j), formula (k), formula (m), formula (n), formula (o), formula (p), formula (q), formula (r), formula (s), formula (t), formula (u), formula (v), formula (w), formula (y), formula (z), formula (aa), formula (ab), formula (ac), formula (ad), formula (ae) and formula (af) each independently represent a hydrogen atom, halogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group, $C_{2-9}$ heteroaryl group (any of the aryl group and heteroaryl group may be optionally substituted with r $R^{19}$ ($R^{19}$ represents the same meaning of $R^{11}$; r represents the same meaning of q)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group, (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom), or $C_{2-9}$ heteroarylcarbonyl group), $C_{3-8}$ cycloalkyl group (the cycloalkyl group may be optionally substituted with a halogen atom, $C_{1-6}$ alkoxy group (the alkoxy group may be optionally substituted with a halogen atom), amino group or hydroxy group), $C_{1-6}$ alkoxy group (the alkoxy group may be optionally substituted with a halogen atom or $C_{1-6}$ alkoxy group (the alkoxy group may be optionally substituted with a halogen atom)), carboxyl group, amino group, hydroxy group, $C_{6-14}$ aryl group or $C_{2-9}$ heteroaryl group (any of the aryl group and heteroaryl group may be optionally substituted with r $R^{19}$ ($R^{19}$ represents the same meaning of $R^{11}$; r represents the same meaning of q))), $C_{1-6}$ thioalkoxy group (the thioalkoxy group may be optionally substituted with a halogen atom, $C_{1-6}$ alkoxy group (the alkoxy group may be optionally substituted with a halogen atom), carboxyl group, hydroxy group, $C_{6-14}$ aryl group or $C_{2-9}$ heteroaryl group (any of the aryl group and heteroaryl group may be optionally substituted with r $R^{19}$ ($R^{19}$ represents the same meaning of $R^{11}$; r represents the same meaning of q))), hydroxy group, $C_{6-14}$ aryl group or $C_{2-9}$ heteroaryl group (any of the aryl group and heteroaryl group may be optionally substituted with r $R^{19}$ ($R^{19}$ represents the same meaning of $R^{11}$; r represents the same meaning of q)), $C_{1-6}$ alkylcarbonyloxy group, nitro group, cyano group, formyl group, formamide group, amino group, sulfo group, $C_{1-6}$ alkyl amino group, di-$C_{1-6}$ alkylamino group, $C_{6-14}$ arylamino group, $C_{2-9}$ heteroarylamino group (any of the arylamino group and the heteroarylamino group may be optionally substituted with r $R^{19}$ ($R^{19}$ represents the same meaning of $R^{11}$; r represents the same meaning of q)), $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{6-14}$ arylcarbonyl group, $C_{2-9}$ heteroarylcarbonyl group (any of the arylcarbonyl group and heteroarylcarbonyl group may be optionally substituted with r $R^{19}$ ($R^{19}$ represents the same meaning of $R^{11}$; r represents the same meaning of q)), $C_{1-6}$ alkoxycarbonyl group, sulfamoyl group, $C_{1-6}$ alkylsulfonyl group, $C_{6-14}$ arylsulfonyl group, $C_{2-9}$ heteroarylsulfonyl group (any of the arylsulfonyl group and heteroarylsulfonyl group may be optionally substituted with r $R^{19}$ ($R^{19}$ represents the same meaning of $R^{11}$; r represents the same meaning of q)), carboxyl group or $C_{2-9}$ heterocyclyl group (the heterocyclyl group may be optionally substituted with a halogen atom, $C_{1-6}$ alkyl group (the alkyl group may be optionally substituted with a halogen atom, $C_{1-6}$ alkoxy group (the alkoxy group may be optionally substituted with a halogen atom), amino group, carboxyl group or hydroxy group), $C_{1-6}$ alkoxy group (the alkoxy group may be optionally substituted with a halogen atom), $C_{6-14}$ aryl group, $C_{2-9}$ heteroaryl group (any of the aryl group and heteroaryl group may be optionally substituted with r $R^{19}$ ($R^{19}$ represents the same meaning of $R^{11}$; r represents the same meaning of q)), hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, sulfamoyl group, $C_{1-6}$ alkylsulfonyl group, carboxyl group or $C_{6-14}$ arylcarbonyl group).

Each atom and each substitution group of $R^{14}$, $R^{15}$, $R^{16}$ and $R^{17}$ in the formula (a), formula (b), formula (c), formula (d), formula (f), formula (g), formula (h), formula (j), formula (k), formula (m), formula (n), formula (o), formula (p), formula (q), formula (r), formula (s), formula (t), formula (u), formula (v), formula (w), formula (y), formula (z), formula (aa), formula (ab), formula (ac), formula (ad), formula (ae) and formula (af) will be specifically described. Examples of the halogen atom include a fluorine atom, chlorine atom, bromine atom and iodine atom; examples of the $C_{1-6}$ alkyl group include a methyl group, ethyl group, n-propyl group, i-propyl group, n-butyl group, i-butyl group, s-butyl group, t-butyl group, n-pentyl group, 2-pentyl group, 3-pentyl group, i-pentyl group, neopentyl group, 2,2-dimethylpropyl group, n-hexyl group, 2-hexyl group, 3-hexyl group, 1-methyl-n-pentyl group, 1,1,2-trimethyl-n-propyl group, 1,2,2-trimethyl-n-propyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, ethylcarbonylaminomethyl group, methylcarbonylaminoethyl group, ethylcarbonylaminoethyl group, methoxycarbonylmethyl group, ethoxycarbonylmethyl group, methoxycarbonylethyl group and ethoxycarbonylethyl group; examples of the $C_{3-8}$ cycloalkyl group include a c-propyl, c-butyl, 1-methyl-c-propyl, 2-methyl-c-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, c-hexyl, c-heptyl, c-octyl, 1-methyl-c-hexyl, 2-methyl-c-hexyl, 3-methyl-c-hexyl, 1,2-dimethyl-c-hexyl, 2,3-dimethyl-c-propyl, 1-ethyl-c-propyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl and 2-ethyl-3-methyl-c-propyl;

examples of the $C_{1-6}$ alkoxy group include a methoxy group, ethoxy group, n-propoxy group, i-propoxy group, n-butoxy group, i-butoxy group, s-butoxy group, t-butoxy group, 1-pentyloxy group, 2-pentyloxy group, 3-pentyloxy, i-pentyloxy, neopentyloxy, 2,2-dimethylpropoxy, 1-hexyloxy, 2-hexyloxy group, 3-hexyloxy group, 1-methyl-n-pentyloxy group, 1,1,2-trimethyl-n-propoxy group, 1,2,2-trimethyl-n-propoxy group and 3,3-dimethyl-n-butoxy group;

examples of the $C_{1-6}$ thioalkoxy group include a methylthio, ethylthio, n-propylthio, i-propylthio, c-propylthio, n-butylthio, i-butylthio, s-butylthio, t-butylthio, n-pentylthio, i-pentylthio, neopentylthio, t-pentylthio, n-hexylthio and c-hexylthio; and examples of the $C_{6-14}$ aryl group include a phenyl group, o-biphenylyl group, m-biphenylyl group, p-biphenylyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group and 9-phenanthryl group.

Examples of the $C_{2-9}$ heteroaryl include a $C_{2-6}$ monocyclic heterocyclic group of up to 5- to 7-membered ring which can contain 1 to 3 oxygen atom(s), nitrogen atom(s), sulfur atom(s) and a combination thereof and $C_{5-9}$ fused bicyclic heterocyclic group having up to 8 to 10 of constituent atoms.

Examples of the $C_{2-6}$ monocyclic heterocyclic group of up to 5 to 7 membered ring include a 2-thienyl group, 3-thienyl group, 2-furyl group, 3-furyl group, 2-pyranyl group, 3-pyranyl group, 4-pyranyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isoxazolyl group, 4-isoxazolyl group, 5-isoxazolyl group, 2-pyridyl group, 3-pyridyl group, 4-pyridyl group, 2-pyradinyl group, 2-pyrimidinyl group, 4-pyrimidinyl group, 5-pyrimidinyl group, 3-pyridazinyl group, 4-pyridazinyl group, 2-1,3,4-oxadiazolyl group, 2-1,3,4-thiadiazolyl group, 3-1,2,4-oxadiazolyl group, 5-1,2,4-oxadiazolyl group, 3-1,2,4-thiadiazolyl group, 5-1,2,4-thiadiazolyl group, 3-1,2,5,-oxadiazolyl group and 3-1,2,5-thiadiazolyl group.

Examples of the $C_{5-9}$ fused bicyclic heterocyclic group having up to 8 to 10 of constituent atoms include a 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromenyl group, 4-chromenyl group, 5-chromenyl group, 6-chromenyl group, 7-chromenyl group, 8-chromenyl group, 1-indolidinyl group, 2-indolidinyl group, 3-indolidinyl group, 5-indolidinyl group, 6-indolidinyl group, 7-indolidinyl group, 8-indolidinyl group, 1-isoindolyl group, 2-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 1-purinyl group, 2-purinyl group, 3-purinyl group, 6-purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthaladinyl group, 5-phthaladinyl group, 6-phthaladinyl group, 1-2,7-naphthyridinyl group, 3-2,7-naphthyridinyl group, 4-2,7-naphthyridinyl group, 1-2,6-naphthyridinyl group, 3-2,6-naphthyridinyl group, 4-2,6-naphthyridinyl group, 2-1,8-naphthyridinyl group, 3-1,8-naphthyridinyl group, 4-1,8-naphthyridinyl group, 2-1,7-naphthyridinyl group, 3-1,7-naphthyridinyl group, 4-1,7-naphthyridinyl group, 5-1,7-naphthyridinyl group, 6-1,7-naphthyridinyl group, 8-1,7-naphthyridinyl group, 2-1,6-naphthyridinyl group, 3-1,6-naphthyridinyl group, 4-1,6-naphthyridinyl group, 5-1,6-naphthyridinyl group, 7-1,6-naphthyridinyl group, 8-1,6-naphthyridinyl group, 2-1,5-naphthyridinyl group, 3-1,5-naphthyridinyl group, 4-1,5-naphthyridinyl group, 6-1,5-naphthyridinyl group, 7-1,5-naphthyridinyl group, 8-1,5-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group and 7-pteridinyl group.

Examples of the $C_{1-6}$ alkylcarbonyloxy group include a methylcarbonyloxy group, ethylcarbonyloxy group, n-propylcarbonyloxy group, i-propylcarbonyloxy group, n-butylcarbonyloxy group, i-butylcarbonyloxy group, s-butylcarbonyloxy group, t-butylcarbonyloxy group, 1-pentylcarbonyloxy group, 2-pentylcarbonyloxy group, 3-pentylcarbonyloxy group, i-pentylcarbonyloxy group, neopentylcarbonyloxy group, t-pentylcarbonyloxy group, 1-hexylcarbonyloxy group, 2-hexylcarbonyloxy group, 3-hexylcarbonyloxy group, 1-methyl-n-pentylcarbonyloxy group, 1,1,2-trimethyl-n-propylcarbonyloxy group, 1,2,2-trimethyl-n-propylcarbonyloxy group and 3,3-dimethyl-n-butylcarbonyloxy group;

examples of the $C_{1-6}$ alkylamino group include a methylamino group, ethylamino group, n-propylamino group, i-propylamino group, c-propylamino group, n-butylamino group, i-butylamino group, s-butylamino group, t-butylamino group, c-butylamino group, 1-pentylamino group, 2-pentylamino group, 3-pentylamino group, i-pentylamino group, neopentylamino group, t-pentylamino group, c-pentylamino group, 1-hexylamino group, 2-hexylamino group, 3-hexylamino group, c-hexylamino group, 1-methyl-n-pentylamino group, 1,1,2-trimethyl-n-propylamino group, 1,2,2-trimethyl-n-propylamino group and 3,3-dimethyl-n-butylamino group;

examples of the di-$C_{1-6}$ alkylamino group includes a dimethylamino group, diethylamino group, di-n-propylamino group, di-i-propylamino group, di-c-propylamino group, di-n-butylamino group, di-i-butylamino group, di-s-butylamino group, di-t-butylamino group, di-c-butylamino group, di-1-pentylamino group, di-2-pentylamino group, di-3-pentylamino group, di-1-pentylamino group, di-neopentylamino group, di-t-pentylamino group, di-c-pentylamino group, di-1-hexylamino group, di-2-hexylamino group, di-3-hexylamino group, di-c-hexylamino group, di-(1-methyl-n-pentyl)amino group, di-(1,1,2-trimethyl-n-propyl)amino group, di-(1,2,2-trimethyl-n-propyl)amino group, di-(3,3-dimethyl-n-butyl)amino group, methyl(ethyl)amino group, methyl(n-propyl)amino group, methyl(i-propyl)amino group, methyl(c-propyl)amino group, methyl(n-butyl)amino group, methyl(i-butyl)amino group, methyl(s-butyl)amino group, methyl(t-butyl)amino group, methyl(c-butyl)amino group, ethyl(n-propyl)amino group, ethyl(i-propyl)amino group, ethyl(c-propyl)amino group, ethyl(n-butyl)amino group, ethyl(i-butyl)amino group, ethyl(s-butyl)amino group, ethyl(t-butyl)amino group, ethyl(c-butyl)amino group, n-propyl(i-propyl)amino group, n-propyl(c-propyl)amino group, n-propyl(n-butyl)amino group, n-propyl(i-butyl)amino group, n-propyl(s-butyl)amino group, n-propyl(t-butyl)amino group, n-propyl(c-butyl)amino group, i-propyl(c-propyl)amino group, i-propyl(n-butyl)amino group, i-propyl(i-butyl)amino group, i-propyl(s-butyl)amino group, i-propyl(t-butyl)amino group, i-propyl(c-butyl)amino group, c-propyl(n-butyl)amino group, c-propyl(i-butyl)amino group, c-propyl(s-butyl)amino group, c-propyl(t-butyl)amino group, c-propyl(c-butyl)amino group, n-butyl(i-butyl)amino group, n-butyl(s-butyl)amino group, n-butyl(t-butyl)amino group, n-butyl(c-butyl)amino group, i-butyl(s-butyl)amino group, i-butyl(t-butyl)amino group, i-butyl(c-butyl)amino group, s-butyl(t-butyl)amino group, s-butyl(c-butyl)amino group and t-butyl(c-butyl)amino group;

examples of the $C_{6-14}$ arylamino group include a phenylamino group, o-biphenylylamino group, m-biphenylylamino group, p-biphenylylamino group, 1-naphthylamino group, 2-naphthylamino group, 1-anthrylamino group, 2-anthrylamino group, 9-anthrylamino group, 1-phenanthrylamino group, 2-phenanthrylamino group, 3-phenanthrylamino group, 4-phenanthrylamino group and 9-phenanthrylamino group; and examples of the $C_{2-9}$ heteroaryl amino group include a $C_{2-6}$ monocyclic heterocyclic amino group of up to 5- to 7-membered ring which can contain 1 to 3 oxygen atom(s) group, nitrogen atom(s), sulfur atom(s) and a combination thereof and $C_{5-9}$ fused bicyclic heterocyclic amino group having up to 8 to 10 of constituent atoms.

Examples of the $C_{2-6}$ monocyclic heterocyclic amino group of up to 5 to 7 membered ring include a 2-thienylamino group, 3-thienylamino group, 2-furylamino group, 3-furylamino group, 2-pyranylamino group, 3-pyranylamino group, 4-pyranylamino group, 1-pyrrolylamino group, 2-pyrrolylamino group, 3-pyrrolylamino group, 1-imidazolylamino group, 2-imidazolylamino group, 4-imidazolylamino group, 1-pyrazolylamino group, 3-pyrazolylamino group, 4-pyrazolylamino group, 2-thiazolylamino group, 4-thiazolylamino group, 5-thiazolylamino group, 3-isothiazolylamino group, 4-isothiazolylamino group, 5-isothiazolylamino group, 2-oxazolylamino group, 4-oxazolylamino group, 5-oxazolylamino group, 3-isoxazolylamino group, 4-isoxazolylamino group, 5-isoxazolylamino group, 2-pyridylamino group, 3-pyridylamino group, 4-pyridylamino group, 2-pyradinylamino group, 2-pyrimidinylamino group, 4-pyrimidinylamino group, 5-pyrimidinylamino group, 3-pyridazinylamino group, 4-pyridazinylamino group, 2-1,3,4-oxadiazolylamino group, 2-1,3,4-thiadiazolylamino group, 3-1,2,4-oxadiazolylamino group, 5-1,2,4-oxadiazolylamino group, 3-1,2,4-thiadiazolylamino group, 5-1,2,4-thiadiazolylamino group, 3-1,2,5,-oxadiazolylamino group and 3-1,2,5-thiadiazolylamino group.

Examples of the $C_{5-9}$ fused bicyclic heterocyclic amino group having up to 8 to 10 of constituent atoms include a 2-benzofuranylamino group, 3-benzofuranylamino group, 4-benzofuranylamino group, 5-benzofuranylamino group, 6-benzofuranylamino group, 7-benzofuranylamino group, 1-isobenzofuranylamino group, 4-isobenzofuranylamino group, 5-isobenzofuranylamino group, 2-benzothienylamino group, 3-benzothienylamino group, 4-benzothienylamino group, 5-benzothienylamino group, 6-benzothienylamino group, 7-benzothienylamino group, 1-isobenzothienylamino group, 4-isobenzothienylamino group, 5-isobenzothienylamino group, 2-chromenylamino group, 3-chromenylamino group, 4-chromenylamino group, 5-chromenylamino group, 6-chromenylamino group, 7-chromenylamino group, 8-chromenylamino group, 1-indolidinylamino group, 2-indolidinylamino group, 3-indolidinylamino group, 5-indolidinylamino group, 6-indolidinylamino group, 7-indolidinylamino group, 8-indolidinylamino group, 1-isoindolylamino group, 2-isoindolylamino group, 4-isoindolylamino group, 5-isoindolylamino group, 1-indolylamino group, 2-indolylamino group, 3-indolylamino group, 4-indolylamino group, 5-indolylamino group, 6-indolylamino group, 7-indolylamino group, 1-indazolylamino group, 2-indazolylamino group, 3-indazolylamino group, 4-indazolylamino group, 5-indazolylamino group, 6-indazolylamino group, 7-indazolylamino group, 1-purinylamino group, 2-purinylamino group, 3-purinylamino group, 6-purinylamino group, 7-purinylamino group, 8-purinylamino group, 2-quinolylamino group, 3-quinolylamino group, 4-quinolylamino group, 5-quinolylamino group, 6-quinolylamino group, 7-quinolylamino group, 8-quinolylamino group, 1-isoquinolylamino group, 3-isoquinolylamino group, 4-isoquinolylamino group, 5-isoquinolylamino group, 6-isoquinolylamino group, 7-isoquinolylamino group, 8-isoquinolylamino group, 1-phthaladinylamino group, 5-phthaladinylamino group, 6-phthaladinylamino group, 1-2,7-naphthyridinylamino group, 3-2,7-naphthyridinylamino group, 4-2,7-naphthyridinylamino group, 1-2,6-naphthyridinylamino group, 3-2,6-naphthyridinylamino group, 4-2,6-naphthyridinylamino group, 2-1,8-naphthyridinylamino group, 3-1,8-naphthyridinylamino group, 4-1,8-naphthyridinylamino group, 2-1,7-naphthyridinylamino group, 3-1,7-naphthyridinylamino group, 4-1,7-naphthyridinylamino group, 5-1,7-naphthyridinylamino group, 6-1,7-naphthyridinylamino group, 8-1,7-naphthyridinylamino group, 2-1,6-naphthyridinylamino group, 3-1,6-naphthyridinylamino group, 4-1,6-naphthyridinylamino group, 5-1,6-naphthyridinylamino group, 7-1,6-naphthyridinylamino group, 8-1,6-naphthyridinylamino group, 2-1,5-naphthyridinylamino group, 3-1,5-naphthyridinylamino group, 4-1,5-naphthyridinylamino group, 6-1,5-naphthyridinylamino group, 7-1,5-naphthyridinylamino group, 8-1,5-naphthyridinylamino group, 2-quinoxalinylamino group, 5-quinoxalinylamino group, 6-quinoxalinylamino group, 2-quinazolinylamino group, 4-quinazolinylamino group, 5-quinazolinylamino group, 6-quinazolinylamino group, 7-quinazolinylamino group, 8-quinazolinylamino group, 3-cinnolinylamino group, 4-cinnolinylamino group, 5-cinnolinylamino group, 6-cinnolinylamino group, 7-cinnolinylamino group, 8-cinnolinylamino group, 2-pteridinylamino group, 4-pteridinylamino group, 6-pteridinylamino group and 7-pteridinylamino group.

Examples of the $C_{1-6}$ alkylcarbonylamino group include a methylcarbonylamino group, ethylcarbonylamino group, n-propylcarbonylamino group, i-propylcarbonylamino group, n-butylcarbonylamino group, i-butylcarbonylamino group, s-butylcarbonylamino group, t-butylcarbonylamino group, 1-pentylcarbonylamino group, 2-pentylcarbonylamino group, 3-pentylcarbonylamino group, i-pentylcarbonylamino group, neopentylcarbonylamino group, t-pentylcarbonylamino group, 1-hexylcarbonylamino group, 2-hexylcarbonylamino group and 3-hexylcarbonylamino group;

examples of the $C_{1-6}$ alkylsulfonamide group include a methanesulfonamide group, ethanesulfonamide group, n-propanesulfonamide group, i-propanesulfonamide group, n-butanesulfonamide group, i-butanesulfonamide group, s-butanesulfonamide group, t-butanesulfonamide group, 1-pentanesulfonamide group, 2-pentanesulfonamide group, 3-pentanesulfonamide group, i-pentanesulfonamide group, neopentanesulfonamide group, t-pentanesulfonamide group, 1-hexanesulfonamide group, 2-hexanesulfonamide group and 3-hexanesulfonamide group;

examples of the $C_{1-6}$ alkylaminocarbonyl group include a methylaminocarbonyl group, ethyaminocarbonyl group, n-propylaminocarbonyl group, i-propylaminocarbonyl group, n-butylaminocarbonyl group, i-butylaminocarbonyl group, s-butyaminocarbonyl group, t-butylaminocarbonyl group, 1-pentylaminocarbonyl group, 2-pentylaminocarbonyl group, 3-pentylaminocarbonyl group, i-pentylaminocarbonyl group, neopentylaminocarbonyl group, t-pentylaminocarbonyl group, 1-hexylaminocarbonyl group, 2-hexylaminocarbonyl group and 3-hexylaminocarbonyl group;

examples of the di-$C_{1-6}$ alkylaminocarbonyl group include a dimethylaminocarbonyl group, diethylaminocarbonyl group, di-n-propylaminocarbonyl group, di-i-propylaminocarbonyl group, di-c-propylaminocarbonyl group, di-n-butylaminocarbonyl group, di-i-butylaminocarbonyl group, di-s-butylaminocarbonyl group, di-t-butylaminocarbonyl group, di-c-butylaminocarbonyl group, di-1-pentylaminocarbonyl group, di-2-pentylaminocarbonyl group, di-3-pentylaminocarbonyl group, di-1-pentylaminocarbonyl group, di-neopentylaminocarbonyl group, di-t-pentylaminocarbonyl group, di-c-pentylaminocarbonyl group, di-1-hexylaminocarbonyl group, di-2-hexylaminocarbonyl group, di-3-hexylaminocarbonyl group, di-c-hexylaminocarbonyl group, di-(1-methyl-n-pentyl)aminocarbonyl group, di-(1,1,2-trimethyl-n-propyl)aminocarbonyl group, di-(1,2,2-trimethyl-n-propyl)aminocarbonyl group, di-(3,3-dimethyl-n-butyl)aminocarbonyl group, methyl(ethyl)aminocarbonyl group, methyl(n-propyl)aminocarbonyl group, methyl(i-propyl)aminocarbonyl group, methyl(c-propyl)aminocarbonyl group, methyl(n-butyl)aminocarbonyl group, methyl(i-butyl)

aminocarbonyl group, methyl(s-butyl)aminocarbonyl group, methyl(t-butyl)aminocarbonyl group, methyl(c-butyl)aminocarbonyl group, ethyl(n-propyl)aminocarbonyl group, ethyl(i-propyl)aminocarbonyl group, ethyl(c-propyl)aminocarbonyl group, ethyl(n-butyl)aminocarbonyl group, ethyl (i-butyl)aminocarbonyl group, ethyl(s-butyl)aminocarbonyl group, ethyl(t-butyl)aminocarbonyl group, ethyl(c-butyl) aminocarbonyl group, n-propyl(i-propyl)aminocarbonyl group, n-propyl(c-propyl)aminocarbonyl group, n-propyl(n-butyl)aminocarbonyl group, n-propyl(i-butyl)aminocarbonyl group, n-propyl(s-butyl)aminocarbonyl group, n-propyl(t-butyl)aminocarbonyl group, n-propyl(c-butyl)aminocarbonyl group, i-propyl(c-propyl)aminocarbonyl group, i-propyl (n-butyl)aminocarbonyl group, i-propyl(i-butyl) aminocarbonyl group, i-propyl(s-butyl)aminocarbonyl group, i-propyl(t-butyl)aminocarbonyl group, i-propyl(c-butyl)aminocarbonyl group, c-propyl(n-butyl)aminocarbonyl group, c-propyl(i-butyl)aminocarbonyl group, c-propyl(s-butyl)aminocarbonyl group, c-propyl(t-butyl)aminocarbonyl group, c-propyl(c-butyl)aminocarbonyl group, n-butyl(i-butyl)aminocarbonyl group, n-butyl(s-butyl)aminocarbonyl group, n-butyl(t-butyl)aminocarbonyl group, n-butyl(c-butyl)aminocarbonyl group, i-butyl(s-butyl)aminocarbonyl group, i-butyl(t-butyl)aminocarbonyl group, i-butyl(c-butyl) aminocarbonyl group, s-butyl(t-butyl)aminocarbonyl group, s-butyl(c-butyl)aminocarbonyl group and t-butyl(c-butyl) aminocarbonyl group;

examples of the $C_{1-6}$ alkylcarbonyl group include a methylcarbonyl group, ethycarbonyl group, n-propylcarbonyl group, i-propylcarbonyl group, n-butylcarbonyl group, i-butylcarbonyl group, s-butycarbonyl group, t-butylaminocarbonyl group, 1-pentylcarbonyl group, 2-pentylcarbonyl group, 3-pentylcarbonyl group, i-pentylcarbonyl group, neopentylcarbonyl group, t-pentylcarbonyl group, 1-hexylcarbonyl group, 2-hexylcarbonyl group and 3-hexylcarbonyl group; and examples of the $C_{6-14}$ arylcarbonyl group include a phenylcarbonyl group, o-biphenylylcarbonyl group, m-biphenylylcarbonyl group, p-biphenylylcarbonyl group, 1-naphthylcarbonyl group, 2-naphthylcarbonyl group, 1-anthrylcarbonyl group, 2-anthrylcarbonyl group, 9-anthrylcarbonyl group, 1-phenanthrylcarbonyl group, 2-phenanthrylcarbonyl group, 3-phenanthrylcarbonyl group, 4-phenanthrylcarbonyl group and 9-phenanthrylcarbonyl group.

Examples of the $C_{2-9}$ heteroaryl carbonyl group include a $C_{2-6}$ monocyclic heterocyclic carbonyl group of up to 5- to 7-membered ring which can contain 1 to 3 oxygen atom(s), nitrogen atom(s), sulfur atom(s) and a combination thereof and $C_{5-9}$ fused bicyclic heterocyclic carbonyl group having up to 8 to 10 of constituent atoms.

Examples of the $C_{2-6}$ monocyclic heterocyclic carbonyl group of up to 5 to 7 membered ring include a 2-thienylcarbonyl group, 3-thienylcarbonyl group, 2-furylcarbonyl group, 3-furylcarbonyl group, 2-pyranylcarbonyl group, 3-pyranylcarbonyl group, 4-pyranylcarbonyl group, 1-pyrrolylcarbonyl group, 2-pyrrolylcarbonyl group, 3-pyrrolylcarbonyl group, 1-imidazolylcarbonyl group, 2-imidazolylcarbonyl group, 4-imidazolylcarbonyl group, 1-pyrazolylcarbonyl group, 3-pyrazolylcarbonyl group, 4-pyrazolylcarbonyl group, 2-thiazolylcarbonyl group, 4-thiazolylcarbonyl group, 5-thiazolylcarbonyl group, 3-isothiazolylcarbonyl group, 4-isothiazolylcarbonyl group, 5-isothiazolylcarbonyl group, 2-oxazolylcarbonyl group, 4-oxazolylcarbonyl group, 5-oxazolylcarbonyl group, 3-isoxazolylcarbonyl group, 4-isoxazolylcarbonyl group, 5-isoxazolylcarbonyl group, 2-pyridylcarbonyl group, 3-pyridylcarbonyl group, 4-pyridylcarbonyl group, 2-pyradinylcarbonyl group, 2-pyrimidinylcarbonyl group, 4-pyrimidinylcarbonyl group, 5-pyrimidinylcarbonyl group, 3-pyridazinylcarbonyl group, 4-pyridazinylcarbonyl group, 2-1,3,4-oxadiazolylcarbonyl group, 2-1,3,4-thiadiazolylcarbonyl group, 3-1,2,4-oxadiazolylcarbonyl group, 5-1,2,4-oxadiazolylcarbonyl group, 3-1,2,4-thiadiazolylcarbonyl group, 5-1,2,4-thiadiazolylcarbonyl group, 3-1,2,5,-oxadiazolylcarbonyl group and 3-1,2,5-thiadiazolylcarbonyl group.

Examples of the $C_{5-9}$ fused bicyclic heterocyclic carbonyl group having up to 8 to 10 of constituent atoms include a 2-benzofuranylcarbonyl group, 3-benzofuranylcarbonyl group, 4-benzofuranylcarbonyl group, 5-benzofuranylcarbonyl group, 6-benzofuranylcarbonyl group, 7-benzofuranylcarbonyl group, 1-isobenzofuranylcarbonyl group, 4-isobenzofuranylcarbonyl group, 5-isobenzofuranylcarbonyl group, 2-benzothienylcarbonyl group, 3-benzothienylcarbonyl group, 4-benzothienylcarbonyl group, 5-benzothienylcarbonyl group, 6-benzothienylcarbonyl group, 7-benzothienylcarbonyl group, 1-isobenzothienylcarbonyl group, 4-isobenzothienylcarbonyl group, 5-isobenzothienylcarbonyl group, 2-chromenylcarbonyl group, 3-chromenylcarbonyl group, 4-chromenylcarbonyl group, 5-chromenylcarbonyl group, 6-chromenylcarbonyl group, 7-chromenylcarbonyl group, 8-chromenylcarbonyl group, 1-indolidinylcarbonyl group, 2-indolidinylcarbonyl group, 3-indolidinylcarbonyl group, 5-indolidinylcarbonyl group, 6-indolidinylcarbonyl group, 7-indolidinylcarbonyl group, 8-indolidinylcarbonyl group, 1-isoindolylcarbonyl group, 2-isoindolylcarbonyl group, 4-isoindolylcarbonyl group, 5-isoindolylcarbonyl group, 1-indolylcarbonyl group, 2-indolylcarbonyl group, 3-indolylcarbonyl group, 4-indolylcarbonyl group, 5-indolylcarbonyl group, 6-indolylcarbonyl group, 7-indolylcarbonyl group, 1-indazolylcarbonyl group, 2-indazolylcarbonyl group, 3-indazolylcarbonyl group, 4-indazolylcarbonyl group, 5-indazolylcarbonyl group, 6-indazolylcarbonyl group, 7-indazolylcarbonyl group, 1-purinylcarbonyl group, 2-purinylcarbonyl group, 3-purinylcarbonyl group, 6-purinylcarbonyl group, 7-purinylcarbonyl group, 8-purinylcarbonyl group, 2-quinolylcarbonyl group, 3-quinolylcarbonyl group, 4-quinolylcarbonyl group, 5-quinolylcarbonyl group, 6-quinolylcarbonyl group, 7-quinolylcarbonyl group, 8-quinolylcarbonyl group, 1-isoquinolylcarbonyl group, 3-isoquinolylcarbonyl group, 4-isoquinolylcarbonyl group, 5-isoquinolylcarbonyl group, 6-isoquinolylcarbonyl group, 7-isoquinolylcarbonyl group, 8-isoquinolylcarbonyl group, 1-phthaladinylcarbonyl group, 5-phthaladinylcarbonyl group, 6-phthaladinylcarbonyl group, 1-2,7-naphthyridinylcarbonyl group, 3-2,7-naphthyridinylcarbonyl group, 4-2,7-naphthyridinylcarbonyl group, 1-2,6-naphthyridinylcarbonyl group, 3-2,6-naphthyridinylcarbonyl group, 4-2,6-naphthyridinylcarbonyl group, 2-1,8-naphthyridinylcarbonyl group, 3-1,8-naphthyridinylcarbonyl group, 4-1,8-naphthyridinylcarbonyl group, 2-1,7-naphthyridinylcarbonyl group, 3-1,7-naphthyridinylcarbonyl group, 4-1,7-naphthyridinylcarbonyl group, 5-1,7-naphthyridinylcarbonyl group, 6-1,7-naphthyridinylcarbonyl group, 8-1,7-naphthyridinylcarbonyl group, 2-1,6-naphthyridinylcarbonyl group, 3-1,6-naphthyridinylcarbonyl group, 4-1,6-naphthyridinylcarbonyl group, 5-1,6-naphthyridinylcarbonyl group, 7-1,6-naphthyridinylcarbonyl group, 8-1,6-naphthyridinylcarbonyl group, 2-1,5- naphthyridinylcarbonyl group, 3-1,5-naphthyridinylcarbonyl group, 4-1,5-naphthyridinylcarbonyl group, 6-1,5-naphthyridinylcarbonyl group, 7-1,5-naphthyridinylcarbonyl group, 8-1,5-naphthyridinylcarbonyl group, 2-quinoxalinylcarbonyl group, 5-quinoxalinylcarbonyl group, 6-quinoxalinylcarbonyl group, 2-quinazolinylcarbonyl group, 4-quinazolinylcarbonyl group, 5-quinazolinylcarbonyl group, 6-quinazolinylcarbonyl group, 7-quinazolinylcarbonyl group, 8-quinazolinylcarbonyl group, 3-cinnolinylcarbonyl group, 4-cinnolinylcarbonyl group, 5-cinnolinylcarbonyl group, 6-cinnolinylcarbonyl group, 7-cinnolinylcarbonyl group, 8-cinnolinylcarbonyl group, 2-pteridinylcarbonyl group, 4-pteridinylcarbonyl group, 6-pteridinylcarbonyl group and 7-pteridinylcarbonyl group.

Examples of the $C_{1-6}$ alkoxycarbonyl group include a methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, 1-pentyloxycarbonyl group, 2-pentyloxycarbonyl group, 3-pentyloxycarbonyl group, i-pentyloxycarbonyl group, neopentyloxycarbonyl group, t-pentyloxycarbonyl group, 1-hexyloxycarbonyl group, 2-hexyloxycarbonyl group and 3-hexyloxycarbonyl group; and examples of the $C_{1-6}$ alkylsulfonyl group include a methanesulfonyl group, trifluoromethanesulfonyl group and ethanesulfonyl group. Examples of the $C_{6-14}$ arylsulfonyl group include a benzenesulfonyl group, o-biphenylsulfonyl group, m-biphenylsulfonyl group, p-biphenylsulfonyl group, 1-naphthalenesulfonyl group, 2-naphthalenesulfonyl group, 1-anthracenesulfonyl group, 2-anthracenesulfonyl group, 9-anthracenesulfonyl group, 1-phenanthrenesulfonyl group, 2-phenanthrenesulfonyl group, 3-phenanthrenesulfonyl group, 4-phenanthrenesulfonyl group and 9-phenanthrenesulfonyl group.

Examples of the $C_{2-9}$ heteroarylsulfonyl group include a $C_{2-6}$ monocyclic heterocyclic sulfonyl group of up to 5- to 7-membered ring which can contain 1 to 3 oxygen atom(s), nitrogen atom(s), sulfur atom(s) and a combination thereof and $C_{5-9}$ fused bicyclic heterocyclic sulfonyl group having up to 8 to 10 of constituent atoms. Examples of the $C_{2-6}$ monocyclic heterocyclic sulfonyl group of up to 5- to 7-membered ring include a 2-thienylsulfonyl group, 3-thienylsulfonyl group, 2-furylsulfonyl group, 3-furylsulfonyl group, 2-pyranylsulfonyl group, 3-pyranylsulfonyl group, 4-pyranylsulfonyl group, 1-pyrrolylsulfonyl group, 2-pyrrolylsulfonyl group, 3-pyrrolylsulfonyl group, 1-imidazolylsulfonyl group, 2-imidazolylsulfonyl group, 4-imidazolylsulfonyl group, 1-pyrazolylsulfonyl group, 3-pyrazolylsulfonyl group, 4-pyrazolylsulfonyl group, 2-thiazolylsulfonyl group, 4-thiazolylsulfonyl group, 5-thiazolylsulfonyl group, 3-isothiazolylsulfonyl group, 4-isothiazolylsulfonyl group, 5-isothiazolylsulfonyl group, 2-oxazolylsulfonyl group, 4-oxazolylsulfonyl group, 5-oxazolylsulfonyl group, 3-isoxazolylsulfonyl group, 4-isoxazolylsulfonyl group, 5-isoxazolylsulfonyl group, 2-pyridylsulfonyl group, 3-pyridylsulfonyl group, 4-pyridylsulfonyl group, 2-pyradinylsulfonyl group, 2-pyrimidinylsulfonyl group, 4-pyrimidinylsulfonyl group, 5-pyrimidinylsulfonyl group, 3-pyridazinylsulfonyl group, 4-pyridazinylsulfonyl group, 2-1,3,4-oxadiazolylsulfonyl group, 2-1,3,4-thiadiazolylsulfonyl group, 3-1,2,4-oxadiazolylsulfonyl group, 5-1,2,4-oxadiazolylsulfonyl group, 3-1,2,4-thiadiazolylsulfonyl group, 5-1,2,4-thiadiazolylsulfonyl group, 3-1,2,5,-oxadiazolylsulfonyl group and 3-1,2,5-thiadiazolylsulfonyl group.

Examples of the $C_{5-9}$ fused bicyclic heterocycle sulfonyl containing up to 8 to 10 of constituent atoms include a 2-benzofuranylsulfonyl group, 3-benzofuranylsulfonyl group, 4-benzofuranylsulfonyl group, 5-benzofuranylsulfonyl group, 6-benzofuranylsulfonyl group, 7-benzofuranylsulfonyl group, 1-isobenzofuranylsulfonyl group, 4-isobenzofuranylsulfonyl group, 5-isobenzofuranylsulfonyl group, 2-benzothienylsulfonyl group, 3-benzothienylsulfonyl group, 4-benzothienylsulfonyl group, 5-benzothienylsulfonyl group, 6-benzothienylsulfonyl group, 7-benzothienylsulfonyl group, 1-isobenzothienylsulfonyl group, 4-isobenzothienylsulfonyl group, 5-isobenzothienylsulfonyl group, 2-chromenylsulfonyl group, 3-chromenylsulfonyl group, 4-chromenylsulfonyl group, 5-chromenylsulfonyl group, 6-chromenylsulfonyl group, 7-chromenylsulfonyl group, 8-chromenylsulfonyl group, 1-indolidinylsulfonyl group, 2-indolidinylsulfonyl group, 3-indolidinylsulfonyl group, 5-indolidinylsulfonyl group, 6-indolidinylsulfonyl group, 7-indolidinylsulfonyl group, 8-indolidinylsulfonyl group, 1-isoindolylsulfonyl group, 2-isoindolylsulfonyl group, 4-isoindolylsulfonyl group, 5-isoindolylsulfonyl group, 1-indolylsulfonyl group, 2-indolylsulfonyl group, 3-indolylsulfonyl group, 4-indolylsulfonyl group, 5-indolylsulfonyl group, 6-indolylsulfonyl group, 7-indolylsulfonyl group, 1-indazolylsulfonyl group, 2-indazolylsulfonyl group, 3-indazolylsulfonyl group, 4-indazolylsulfonyl group, 5-indazolylsulfonyl group, 6-indazolylsulfonyl group, 7-indazolylsulfonyl group, 1-purinylsulfonyl group, 2-purinylsulfonyl group, 3-purinylsulfonyl group, 6-purinylsulfonyl group, 7-purinylsulfonyl group, 8-purinylsulfonyl group, 2-quinolylsulfonyl group, 3-quinolylsulfonyl group, 4-quinolylsulfonyl group, 5-quinolylsulfonyl group, 6-quinolylsulfonyl group, 7-quinolylsulfonyl group, 8-quinolylsulfonyl group, 1-isoquinolylsulfonyl group, 3-isoquinolylsulfonyl group, 4-isoquinolylsulfonyl group, 5-isoquinolylsulfonyl group, 6-isoquinolylsulfonyl group, 7-isoquinolylsulfonyl group, 8-isoquinolylsulfonyl group, 1-phthaladinylsulfonyl group, 5-phthaladinylsulfonyl group, 6-phthaladinylsulfonyl group, 1-2,7-naphthyridinylsulfonyl group, 3-2,7-naphthyridinylsulfonyl group, 4-2,7-naphthyridinylsulfonyl group, 1-2,6-naphthyridinylsulfonyl group, 3-2,6-naphthyridinylsulfonyl group, 4-2,6-naphthyridinylsulfonyl group, 2-1,8-naphthyridinylsulfonyl group, 3-1,8-naphthyridinylsulfonyl group, 4-1,8-naphthyridinylsulfonyl group, 2-1,7-naphthyridinylsulfonyl group, 3-1,7-naphthyridinylsulfonyl group, 4-1,7-naphthyridinylsulfonyl group, 5-1,7-naphthyridinylsulfonyl group, 6-1,7-naphthyridinylsulfonyl group, 8-1,7-naphthyridinylsulfonyl group, 2-1,6-naphthyridinylsulfonyl group, 3-1,6-naphthyridinylsulfonyl group, 4-1,6-naphthyridinylsulfonyl group, 5-1,6-naphthyridinylsulfonyl group, 7-1,6-naphthyridinylsulfonyl group, 8-1,6-naphthyridinylsulfonyl group, 2-1,5-naphthyridinylsulfonyl group, 3-1,5-naphthyridinylsulfonyl group, 4-1,5-naphthyridinylsulfonyl group, 6-1,5-naphthyridinylsulfonyl group, 7-1,5-naphthyridinylsulfonyl group, 8-1,5-naphthyridinylsulfonyl group, 2-quinoxalinylsulfonyl group, 5-quinoxalinylsulfonyl group, 6-quinoxalinylsulfonyl group, 2-quinazolinylsulfonyl group, 4-quinazolinylsulfonyl group, 5-quinazolinylsulfonyl group, 6-quinazolinylsulfonyl group, 7-quinazolinylsulfonyl group, 8-quinazolinylsulfonyl group, 3-cinnolinylsulfonyl group, 4-cinnolinylsulfonyl group, 5-cinnolinylsulfonyl group, 6-cinnolinylsulfonyl group, 7-cinnolinylsulfonyl group, 8-cinnolinylsulfonyl group, 2-pteridinylsulfonyl group, 4-pteridinylsulfonyl group, 6-pteridinylsulfonyl group and 7-pteridinylsulfonyl group.

Examples of the $C_{2-9}$ heterocyclyl group include a monocyclic and ring-fused bicyclic heterocyclic group containing one or more atom(s) freely selected from nitrogen atom, oxygen atom and sulfur atom and 2 to 9 carbon atoms, and specifically include following groups.

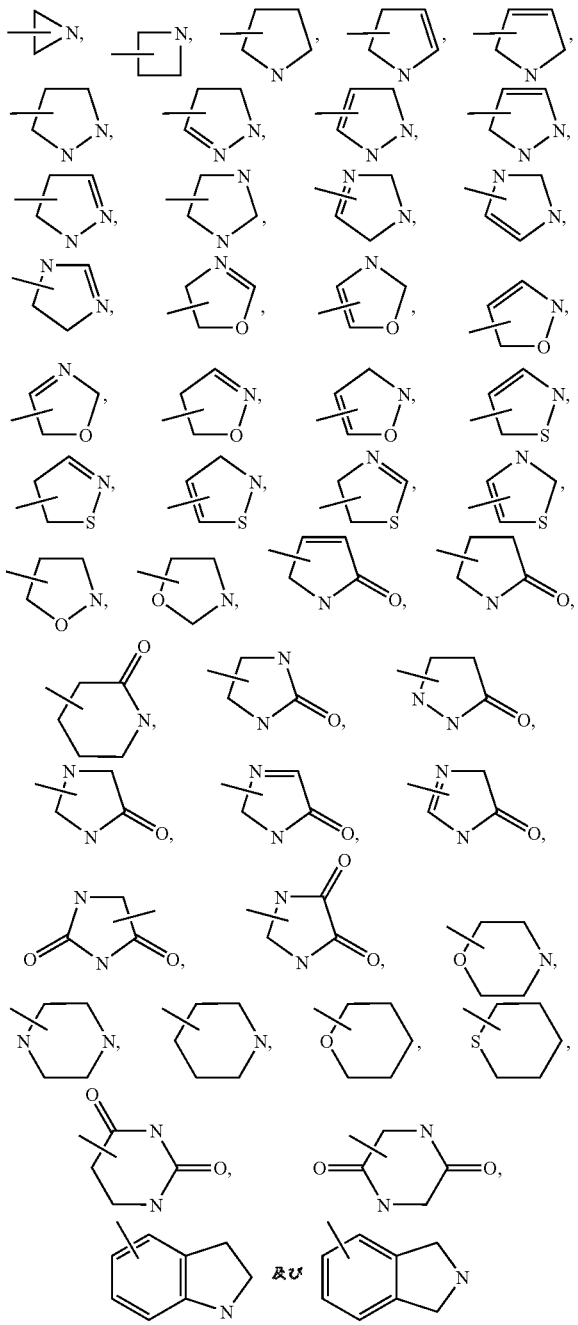

In the above formula, "—" (which means chemical bond) illustrated in each ring structure means that a substitution group can take place in any position which can be substituted according to chemical structure, and does not mean specifying a substitution position.

$R^{14}$, $R^{15}$, $R^{16}$ and $R^{17}$ in the formula (a), formula (b), formula (c), formula (d), formula (f), formula (g), formula (h), formula (j), formula (k), formula (m), formula (n), formula (o), formula (p), formula (q), formula (r), formula (s), formula (t), formula (u), formula (v), formula (w), formula (y), formula (z), formula (aa), formula (ab), formula (ac), formula (ad), formula (ae) and formula (af) are independently preferably hydrogen atom, fluorine atom, chlorine, atom, bromine atom, methyl group, ethyl group, n-propyl group, i-propyl group, n-butyl group, n-pentyl group, i-pentyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, ethylcarbonylaminomethyl group, methylcarbonylaminoethyl group, ethylcarbonylaminoethyl group, methoxycarbonylmethyl group, ethoxycarbonylmethyl group, methoxycarbonylethyl group, ethoxycarbonylethyl group, c-propyl group, c-pentyl group, c-hexyl group, methoxy group, ethoxy group, n-propoxy group, i-propoxy group, methylthio group, ethylthio group, phenyl group, o-biphenylyl group, m-biphenylyl group, p-biphenylyl group, 1-naphthyl group, 2-naphthyl group, 2-pyridyl group, 3-pyridyl group, 4-pyridyl group, methylcarbonyloxy group, ethylcarbonyloxy group, n-propylcarbonyloxy group, i-propylcarbonyloxy group, n-butylcarbonyloxy group, t-butylcarbonyloxy group, methylamino group, ethylamino group, n-propylamino group, i-propylamino group, n-butylamino group, dimethylamino group, diethylamino group, di-n-propylamino group, di-i-propylamino group, di-n-butylamino group, phenylamino group, o-biphenylylamino group, m-biphenylylamino group, p-biphenylylamino group, 1-naphthylamino group, 2-naphthylamino group, 2-pyridylamino group, 3-pyridylamino group, 4-pyridylamino group, methylcarbonylamino group, ethylcarbonylamino group, n-propylcarbonylamino group, i-propylcarbonylamino group, n-butylcarbonylamino group, methanesulfonamide group, ethanesulfonamide group, n-propanesulfonamide group, i-propanesulfonamide group, n-butanesulfonamide group, methylaminocarbonyl group, ethyaminocarbonyl group, n-propylaminocarbonyl group, i-propylaminocarbonyl group, n-butylaminocarbonyl group, dimethylaminocarbonyl group, diethylaminocarbonyl group, di-n-propylaminocarbonyl group, di-i-propylaminocarbonyl group, di-c-propylaminocarbonyl group, di-n-butylaminocarbonyl group, methylcarbonyl group, ethycarbonyl group, n-propylcarbonyl group, i-propylcarbonyl group, n-butylcarbonyl group, phenylcarbonyl group, o-biphenylylcarbonyl group, m-biphenylylcarbonyl group, p-biphenylylcarbonyl group, 1-naphthylcarbonyl group, 2-naphthylcarbonyl group, 2-pyridylcarbonyl group, 3-pyridylcarbonyl group, 4-pyridylcarbonyl group, methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, methanesulfonyl group, trifluoromethanesulfonyl group, benzenesulfonyl group, o-biphenylsulfonyl group, m-biphenylsulfonyl group, p-biphenylsulfonyl group, 1-naphthalenesulfonyl group, 2-naphthalenesulfonyl group, 2-pyridylsulfonyl group, 3-pyridylsulfonyl group, 4-pyridylsulfonyl group, amino group, cyano group, carbamoyl group, carboxyl group and following groups.

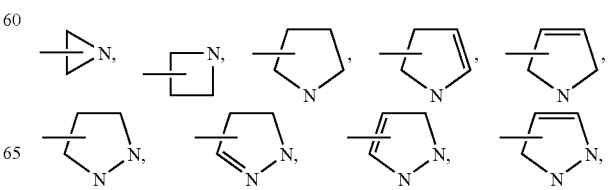

-continued

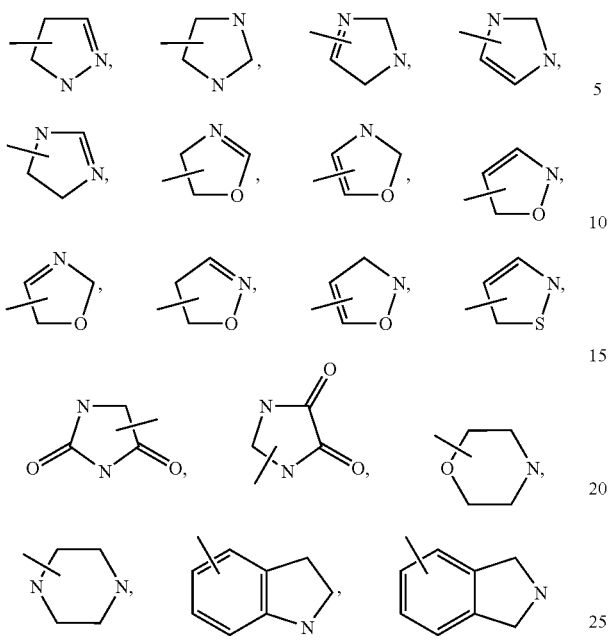

In the above formula, "—" (which means chemical bond) illustrated in each ring structure means that a substitution group can take place in any position which can be substituted according to chemical structure, and does not mean specifying a substitution position.

Q in the formula (c), formula (d), formula (p), formula (q), formula (v), formula (w), formula (ab), formula (ac) and formula (ad) means O (oxygen atom), S (sulfur atom), SO (sulfinyl group) or $SO_2$ (sulfonyl group). Q in the formula (c), formula (d), formula (p), formula (q), formula (v), formula (w), formula (ab), formula (ac) and formula (ad) is preferably O (oxygen atom).

When a partial ring structure A in the formula (11) or formula (12) is the formula (a), formula (b), formula (i), formula (k), formula (o), formula (p), formula (s), formula (v), formula (y), formula (ae), formula (ag) or formula (ah), $R^{12}$, $R^{13}$, $R^{14}$, $R^{15}$ and $R^{16}$ in the formula (a), formula (b), formula (l), formula (k), formula (o), formula (p), formula (s), formula (v), formula (y), formula (ae), formula (ag) or formula (ah) will be described.

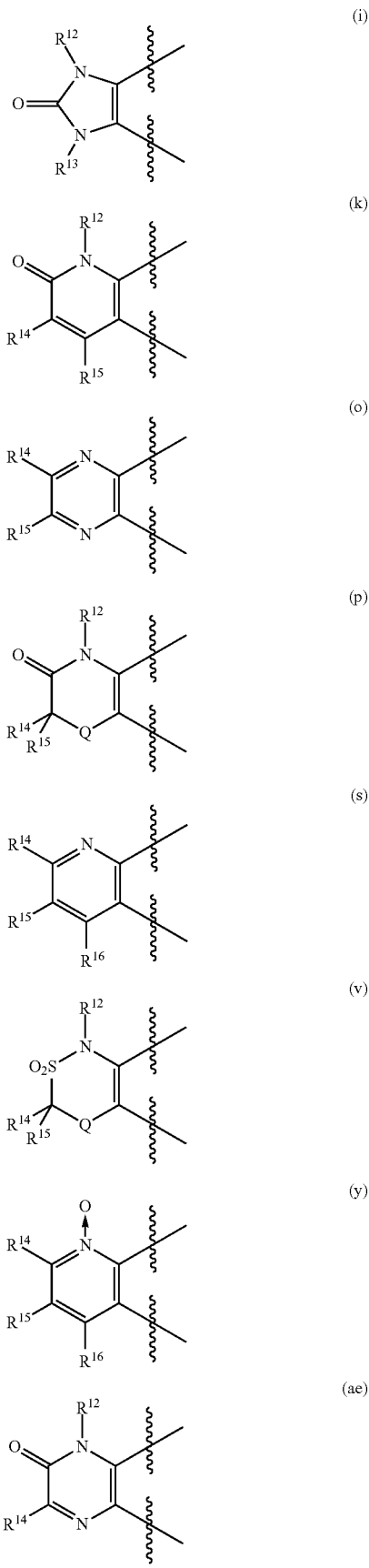

-continued

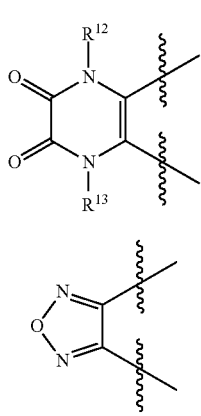
(ag)

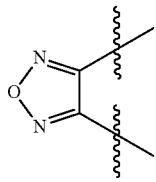
(ah)

When a partial ring structure A in the formula (11) or formula (12) is the formula (a), formula (b), formula (i), formula (k), formula (o), formula (p), formula (s), formula (v), formula (y), formula (ae), formula (ag) or formula (ah), $R^{14}$ and $R^{15}$ in the formula (a), formula (b), formula (i), formula (k), formula (p), formula (v), formula (ae), or formula (ag) will be described.

$R^{12}$ and $R^{13}$ in the formula (a), formula (b), formula (i), formula (k), formula (p), formula (v), formula (ae) and formula (ag) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group or hydroxy group).

Each substitution group of $R^{12}$ and $R^{13}$ in the formula (a), formula (b), formula (i), formula (k), formula (p), formula (v), formula (ae) and formula (ag) will be specifically described.

Examples of the $C_{1-6}$ alkyl group include a methyl group, trifluoromethyl group, methoxymethyl group, ethyl group, n-propyl group, i-propyl group, n-butyl group, i-butyl group, s-butyl group, t-butyl group, n-pentyl group, 2-pentyl group, 3-pentyl group, i-pentyl group, neopentyl group, 2,2-dimethylpropyl group, n-hexyl group, 2-hexyl group, 3-hexyl group, 1-methyl-n-pentyl group, 1,1,2-trimethyl-n-propyl group, 1,2,2-trimethyl-n-propyl group and 3,3-dimethyl-n-butyl group.

$R^{12}$ and $R^{13}$ in the formula (a), formula (b), formula (i), formula (k), formula (p), formula (v), formula (ae) and formula (ag) are independently preferably hydrogen atom, methyl group, trifluoromethyl group, methoxymethyl group, ethyl group, n-propyl group, i-propyl group, n-butyl group, n-pentyl group, i-pentyl group, amino group and hydroxy group, and more preferably hydrogen atom and methyl group.

When a partial ring structure A in the formula (11) or formula (12) is the formula (a), formula (b), formula (i), formula (k), formula (o), formula (p), formula (s), formula (v), formula (y), formula (ae), formula (ag) or formula (ah), $R^{14}$, $R^{15}$ and $R^{16}$ in the formula (a), formula (b), formula (k), formula (o), formula (p), formula (s), formula (v), formula (y), and formula (ae) will be described. $R^{14}$, $R^{15}$ and $R^{16}$ in the formula (a), formula (b), formula (k), formula (o), formula (p), formula (s), formula (v), formula (y) and formula (ae) each independently represent a hydrogen atom, halogen atom or $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group or $C_{1-6}$ alkoxycarbonyl group).

Each atom and each substitution group of $R^{14}$, $R^{15}$ and $R^{16}$ in the formula (a), formula (b), formula (k), formula (o), formula (p), formula (s), formula (v), formula (y) and formula (ae) will be specifically described.

Examples of the halogen atom include a fluorine atom, chlorine atom, bromine atom and iodine atom;

examples of the $C_{1-6}$ alkyl group include a methyl group, trifluoromethyl group, ethyl group, n-propyl group, i-propyl group, n-butyl group, i-butyl group, s-butyl group, t-butyl group, n-pentyl group, 2-pentyl group, 3-pentyl group, i-pentyl group, neopentyl group, 2,2-dimethylpropyl group, n-hexyl group, 2-hexyl group, 3-hexyl group, 1-methyl-n-pentyl group, 1,1,2-trimethyl-n-propyl group, 1,2,2-trimethyl-n-propyl group, 3,3-dimethyl-n-butyl group, methylcarbonyloxymethyl group, ethylcarbonyloxymethyl group, methylcarbonyloxyethyl group, ethylcarbonyloxyethyl group, methylcarbonylaminomethyl group, ethylcarbonylaminomethyl group, methylcarbonylaminoethyl group, ethylcarbonylaminoethyl group, methoxycarbonylmethyl group, ethoxycarbonylmethyl group, methoxycarbonylethyl group, trifluoromethoxycarbonylmethyl group and ethoxycarbonylethyl group. Examples of the $C_{1-6}$ alkylcarbonylamino group include a methylcarbonylamino group, trifluoromethylcarbonylamino group, ethylcarbonylamino group, n-propylcarbonylamino group, i-propylcarbonylamino group, n-butylcarbonylamino group, i-butylcarbonylamino group, s-butylcarbonylamino group, t-butylcarbonylamino group, 1-pentylcarbonylamino group, 2-pentylcarbonylamino group, 3-pentylcarbonylamino group, i-pentylcarbonylamino group, neopentylcarbonylamino, t-pentylcarbonylamino group, 1-hexylcarbonylamino group, 2-hexylcarbonylamino group and 3-hexylcarbonylamino group;

examples of the $C_{3-8}$ cycloalkylcarbonyl group include a c-propylcarbonyl group, c-butylcarbonyl group, 1-methyl-c-propylcarbonyl group, 2-methyl-c-propylcarbonyl group, c-pentylcarbonyl group, 1-methyl-c-butylcarbonyl group, 2-methyl-c-butylcarbonyl group, 3-methyl-c-butylcarbonyl group, 1,2-dimethyl-c-propylcarbonyl group, 2,3-dimethyl-c-propylcarbonyl group, 1-ethyl-c-propylcarbonyl group, 2-ethyl-c-propylcarbonyl group, c-hexylcarbonyl group, c-heptylcarbonyl group, c-octylcarbonyl group, 1-methyl-c-hexylcarbonyl group, 2-methyl-c-hexylcarbonyl group, 3n-methyl-c-hexylcarbonyl group, 1,2-dimethyl-c-hexylcarbonyl group, 2,3-dimethyl-c-propylcarbonyl group, 1-ethyl-c-propylcarbonyl group, 1-methyl-c-pentylcarbonyl group, 2-methyl-c-pentylcarbonyl group, 3-methyl-c-pentylcarbonyl group, 1-ethyl-c-butylcarbonyl group, 2-ethyl-c-butylcarbonyl group, 3-ethyl-c-butylcarbonyl group, 1,2-dimethyl-c-butylcarbonyl group, 1,3-dimethyl-c-butylcarbonyl group, 2,2-dimethyl-c-butylcarbonyl group, 2,3-dimethyl-c-butylcarbonyl group, 2,4-dimethyl-c-butylcarbonyl group, 3,3-dimethyl-c-butylcarbonyl group, 1-n-propyl-c-propylcarbonyl group, 2-n-propyl-c-propylcarbonyl group, 1-i-propyl-c-propylcarbonyl group, 2-i-propyl-c-propylcarbonyl group, 1,2,2-trimethyl-c-propylcarbonyl group, 1,2,3-trimethyl-c-propylcarbonyl group, 2,2,3-trimethyl-c-propylcarbonyl group, 1-ethyl-2-methyl-c-propylcarbonyl group, 2-ethyl-1-methyl-c-propylcarbonyl group, 2-ethyl-2-methyl-c-propylcarbonyl group and 2-ethyl-3-methyl-c-propylcarbonyl group; and examples of the $C_{1-6}$ alkoxycarbonyl group include a methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, 1-pentyloxycarbonyl group, 2-pentyloxycarbonyl group, 3-pentyloxycarbonyl group, i-pentyloxycarbonyl group, neopentyloxycarbonyl group, t-pentyloxycarbonyl group, 1-hexyloxycarbonyl group, 2-hexyloxycarbonyl group and 3-hexyloxycarbonyl group.

$R^{14}$, $R^{15}$ and $R^{16}$ in the formula (a), formula (b), formula (k), formula (o), formula (p), formula (s), formula (v), formula (y) and formula (ae) are independently preferably hydrogen atom, fluorine atom, chlorine, atom, bromine atom, methyl group, trifluoromethyl group, ethyl group, n-propyl group, i-propyl group, n-butyl group, n-pentyl group, i-pentyl group, methylcarbonyloxymethyl group, ethylcarbonyloxymethyl group, methylcarbonyloxyethyl group, ethylcarbonyloxyethyl group, methylcarbonylaminomethyl group, ethylcarbonylaminoethyl group, methylcarbonylaminoethyl group, ethylcarbonylaminoethyl group, methoxycarbonylmethyl group, ethoxycarbonylmethyl group, methoxycarbonylethyl group, trifluoromethoxycarbonylmethyl group and ethoxycarbonylethyl group, and more preferably hydrogen atom group, fluorine atom group, chlorine atom, methyl group, trifluoromethyl group, ethyl group, n-propyl group, i-propyl group, methylcarbonyloxymethyl group, ethylcarbonyloxymethyl group, methylcarbonylaminoethyl group, ethylcarbonylaminoethyl group, methoxycarbonylmethyl group and trifluoromethoxycarbonylmethyl group.

Partial ring structures of A in the formula (11) or formula (12) are the formula (p) and formula (v), and Q in the formula (p) or formula (v) means O (oxygen atom), S (sulfur atom), SO (sulfinyl group) or $SO_2$ (sulfonyl group). Q in the formula (p) or formula (v) is preferably O (oxygen atom).

$R^9$, $R^{10}$, W, X, Y and Z in the formula (13) will be described.

$R^9$ and $R^{10}$ in the formula (13) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group), $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group), or $C_{1-6}$ alkoxy group (the alkoxy group may be optionally substituted with a halogen atom)).

Each substitution group of $R^9$ and $R^{10}$ in the formula (13) will be specifically described.

Examples of the $C_{1-6}$ alkyl group include a methyl group, trifluoromethyl group, methoxymethyl group, ethyl group, n-propyl group, i-propyl group, n-butyl group, i-butyl group, s-butyl group, t-butyl group, 1-pentyl group, 2-pentyl group, 3-pentyl group, i-pentyl group, neopentyl group, 2,2-dimethylpropyl group, 1-hexyl group, 2-hexyl group, 3-hexyl group, 1-methyl-n-pentyl group, 1,1,2-trimethyl-n-propyl group, 1,2,2-trimethyl-n-propyl group and 3,3-dimethyl-n-butyl group; and examples of the $C_{6-14}$ aryl group include a phenyl group, o-biphenylyl group, m-biphenylyl group, p-biphenylyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group and 9-phenanthryl group.

$R^9$ and $R^{10}$ in the formula (13) are preferably methyl group, trifluoromethyl group and ethyl group, and more preferably methyl group.

W in the formula (13) preferably represents a hydrogen atom, hydroxy group, $C_{1-6}$ alkoxy group (the alkoxy group may be optionally substituted with a halogen atom), halogen atom, $C_{1-4}$ alkyl group or $C_{1-6}$ alkylsulfonamide group (the alkyl group and the alkylsulfonamide group may be optionally substituted with a halogen atom).

Each atom and each substitution group of W in the formula (13) will be specifically described.

Examples of the $C_{1-6}$ alkoxy group include a methoxy group, ethoxy group, n-propoxy group, i-propoxy group, n-butoxy group, i-butoxy group, s-butoxy group, t-butoxy group, 1-pentyloxy group, 2-pentyloxy group, 3-pentyloxy group, i-pentyloxy group, neopentyloxy group, 2,2-dimethylpropoxy group, 1-hexyloxy group, 2-hexyloxy group, 3-hexyloxy group, 1-methyl-n-pentyloxy group, 1,1,2-trimethyl-n-propoxy group, 1,2,2-trimethyl-n-propoxy group and 3,3-dimethyl-n-butoxy group;

examples of the halogen atom include a fluorine atom, chlorine atom, bromine atom and iodine atom;

examples of the $C_{1-4}$ alkyl group include a methyl group, trifluoromethyl group, ethyl group, n-propyl group, i-propyl group, n-butyl group, i-butyl group, s-butyl group and t-butyl group; and examples of the $C_{1-6}$ alkylsulfonamide group include a methanesulfonamide group, trifluoromethanesulfonamide group, ethanesulfonamide group, n-propanesulfonamide group, i-propanesulfonamide group, n-butanesulfonamide group, i-butanesulfonamide group, s-butanesulfonamide group, t-butanesulfonamide group, 1-pentanesulfonamide group, 2-pentanesulfonamide group, 3-pentanesulfonamide group, i-pentanesulfonamide group, neopentanesulfonamide group, t-pentanesulfonamide group, 1-hexanesulfonamide group, 2-hexanesulfonamide group and 3-hexanesulfonamide group.

W in the formula (13) preferably represents a hydrogen atom, hydroxy group, fluorine atom, chlorine atom, bromine atom, methyl group, trifluoromethyl group, ethyl group, methoxy group, ethoxy group, n-propoxy group, i-propoxy group, methanesulfonamide group, trifluoromethanesulfonamide group, ethanesulfonamide group, n-propanesulfonamide group, i-propanesulfonamide and n-butanesulfonamide group and more preferably hydrogen atom, hydroxy group, fluorine atom, methyl group, trifluoromethyl group, ethyl group, methoxy group, methanesulfonamide group and trifluoromethanesulfonamide group.

X in the formula (13) represents $NR^{20}$; N represents a nitrogen atom; and $R^{20}$ represents a hydrogen atom or $C_{1-4}$ alkyl group.

Each substitution group of $R^{20}$ of X in the formula (13) will be described.

Examples of the $C_{1-4}$ alkyl group include a methyl group, ethyl group, n-propyl group, i-propyl group, n-butyl group, i-butyl group, s-butyl group and t-butyl group.

$R^{20}$ of X in the formula (13) is preferably hydrogen atom, methyl group and ethyl group.

Y in the formula (13) is chemical bond, SO (sulfinyl group) or $SO_2$ (sulfonyl group), and preferably chemical bond and $SO_2$.

Z in the formula (13) is $C_{1-4}$ alkyl group (the $C_{1-4}$ alkyl group may be optionally substituted with 1 to 5 halogen atom(s) or a phenyl group (the phenyl group may be optionally substituted with a $C_{1-4}$ alkyl group)) or phenyl group (the phenyl group may be optionally substituted with a $C_{1-4}$ alkyl group).

Each substitution group of Z in the formula (13) will be specifically described.

Examples of the $C_{1-4}$ alkyl group includes a methyl group, trifluoromethyl group, ethyl group, n-propyl group, i-propyl group, n-butyl group, i-butyl group, s-butyl group and t-butyl group.

Z in the formula (13) is preferably methyl group, trifluoromethyl group, ethyl group, n-propyl group, i-propyl group and phenyl group.

When an optically active titanium complex represented by any of the formula (1), formula (1'), formula (2), formula (2'), formula (3), formula (3'), formula (4) and formula (4') is used as a catalyst, a used amount of the optically active titanium complex to that of chromene compound represented by the formula (10), formula (11), formula (12) or formula (13) is in the range of 0.001 to 100 mol %, preferably 0.01 to 20 mol %, and more preferably 0.3 to 5 mol %.

When an optically active titanium complex represented by any of the formula (1), formula (1'), formula (2), formula (2'), formula (3), formula (3'), formula (4) and formula (4') is used as a catalyst, a solvent used in asymmetric epoxidation is in the case of an aprotic organic solvent, the aprotic organic solvents including a halogen-type solvent, an aromatic hydrocarbon-type solvent, an ester-type solvent, an ether-type solvent or a nitrile-type solvent, and in the case of a protic organic solvent, the protic organic solvent including an alcohol-type solvent. Examples of the halogen-type solvent include dichloromethane, chloroform, 1,2 dichloroethane and chlorobenzene; examples of the aromatic hydrocarbon-type solvent include benzene and toluene; examples of the ester-type solvent include ethyl acetate; examples of the ether-type solvent include tetrahydrofuran and diethylether; and examples of the nitrile-type solvent include butyronitrile, propionitrile and acetonitrile. Examples of the alcohol-type solvent include methanol, ethanol and i-propanol. Moreover, a mixture of the above-mentioned solvents is included. In addition, when hydrogen peroxide aqueous solution is used in this reaction, an organic layer and an aqueous layer may be separated by mixing hydrogen peroxide aqueous solution with an organic solvent which is not soluble in water. However, this two-phase solvent can also be used as a reaction solvent of the present invention. The preferable solvent is an aprotic organic solvent of dichloromethane, 1,2 dichloroethane, chlorobenzene, toluene, ethyl acetate and a mixture thereof.

As a production operation, when a chromene compound, an optically active titanium complex and an oxidizing reagent are added to an organic solvent, the reaction will proceed. Preferable addition order is that an oxidizing reagent is added to a solution of an organic solvent, a chromene compound and an optically active titanium complex.

Specific examples of an oxidizing reagent used in the reaction include iodosobenzene, sodium hypochlorite, m-chloroperbenzoic acid, Oxone (registered trademark of DuPont), hydrogen peroxide aqueous solution, urea-hydrogen peroxide adduct (UHP), oxaziridine, N-methylmorpholineoxide (NMO), t-butylhydroperoxide (TBHP), cumenehydroperoxide (CHP) or a combination thereof. Of these oxidizing reagents, hydrogen peroxide aqueous solution, urea-hydrogen peroxide adduct (UHP) and a mixture thereof are preferable. When an oxidizing reagent is hydrogen peroxide aqueous solution, a concentration can be in the range of 1 to 100% by weight, and preferably in the range of 5 to 60% by weight.

A used amount of the oxidizing reagent used in the reaction to an amount of chromene compound represented by the formula (10), formula (11), formula (12) or formula (13) can be 1 to 10 equivalent(s), and preferably 1 to 3 equivalent(s).

Examples of an addition method of the oxidizing agent include fractionated addition and continuous addition, other than one-time addition.

When the addition method is the continuous addition, a preferable addition rate is in the range in which the temperature in the reaction solvent system does not sharply increase, and specifically the addition rate is in the range of 0.01 to 40000 equivalent per hour, and more preferably in the range of 0.05 to 0.3 equivalent per hour. The term "fractionated addition" means a method of separately adding a used oxidizing reagent in p times (p can be any integer). A fraction may be dividing equally or unequally, and p is preferably in the range of 2 to 100.

A reaction temperature can be in the range of −78° C. to a reflux temperature of a solvent or in the range of a melting temperature of a solvent to a reflux temperature of the solvent, preferably in the range of −20 to 50° C., and more preferably 0 to 35° C.

A pressure in the reaction system can be 10 kPa to 1100 kPa, preferably 15 kPa to 200 kPa. By applying pressure, the reaction can be conducted under higher temperature than a reflux temperature of a solvent under normal pressure.

A reaction time can be shortened by adding an additional catalyst of optically active titanium complex during the reaction. Moreover, reaction time can be shortened by adding an additional oxidizing reagent.

After completion of the reaction, a target optically active chromene oxide compound can be obtained by separating and purifying the reaction mixture with distillation operation, silica gel column chromatography, separation and extraction operation, recrystallization operation or a mixed operation thereof.

An optical purity of the obtained optically active chromene oxide compound can be analyzed by optically active high-performance liquid chromatography analysis, optically active gas chromatography analysis or measurement of optical rotation.

The present invention will be further described hereinafter by way of examples. However, the present invention is not limited to these examples.

Of optical active chromene compounds in those examples, some compounds have an absolute configuration of asymmetric carbons that has not known yet. For these compounds, description of chemical formulae and compound names represents provisional absolute configuration shown by adding an asterisk (*) to each absolute configuration representation in the compound name and of each asymmetric carbon in the chemical formulae.

Synthesis of optically active titanium-salalen complexes (A), (B) and (C)

The optically active titanium-salalen complexes (A), (B) and (C) used in examples were synthesized according to the method described in Non-Patent Document 8 (Angew. Chem. Int. Ed., 44, 4935-4939 (2005)).

(A)
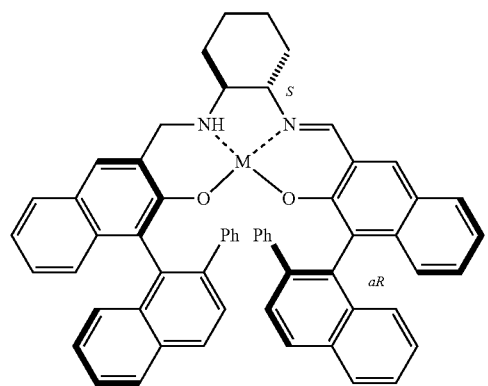
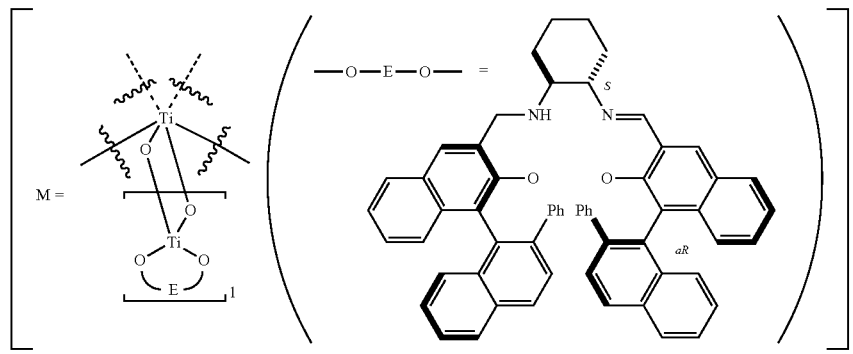
(B)
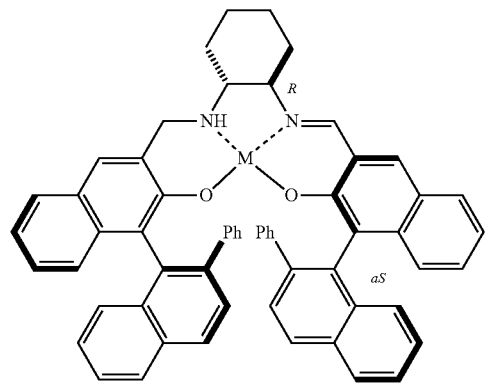
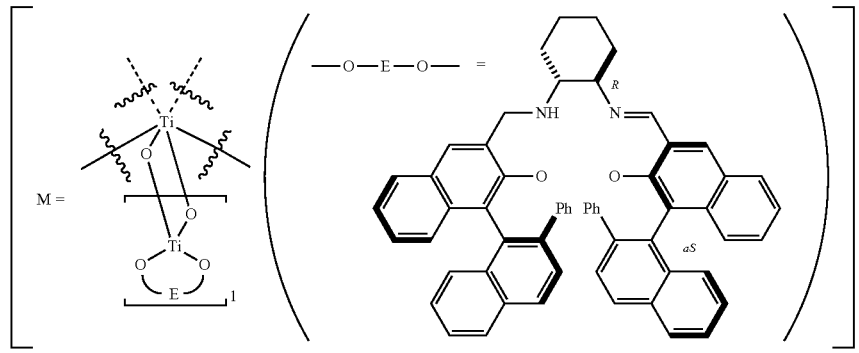

(C)
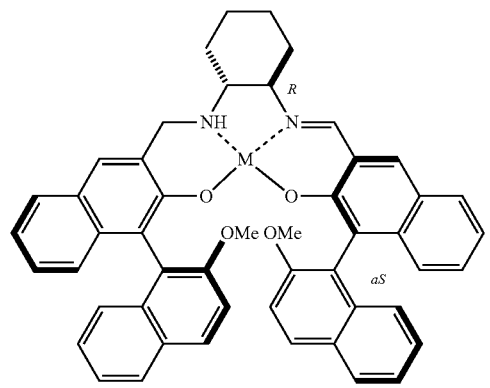
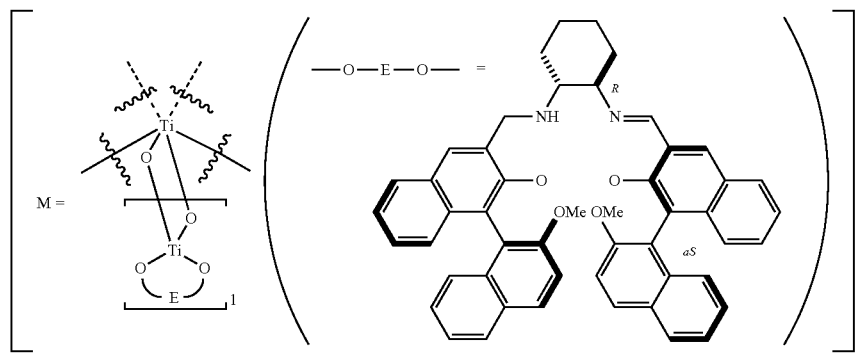
The optically active titanium-salan complex (D) represented by the following formula was obtained by the following method.
(D)
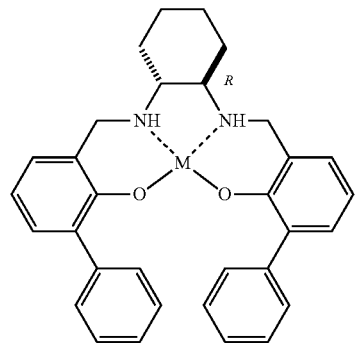
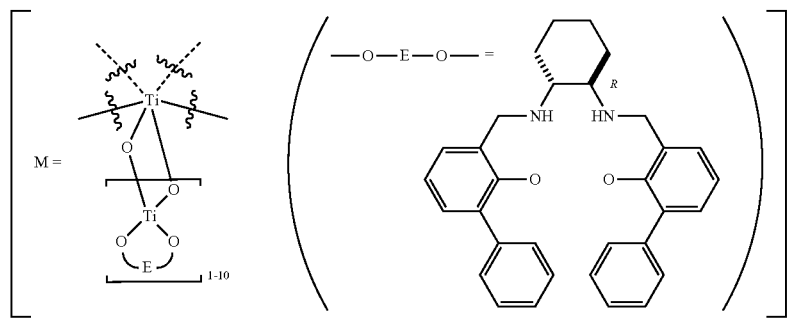

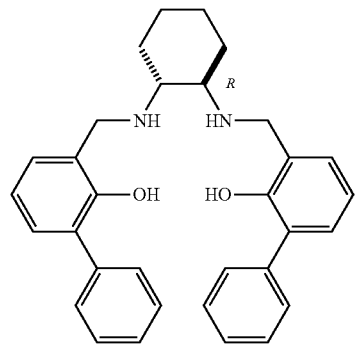

Salan Ligand (42')

To a dichloromethane reaction solvent of the salan ligand (42'), 1.1 mol per mol of the salan ligand (42') of titanium tetraisopropoxide (Ti(Oi-Pr)$_4$) was added under nitrogen atmosphere at 25 to 28° C. Then, the mixture was stirred for 5 hours and water was added at 25 to 28° C. and the resultant reaction solution was stirred for 12 hours. The reaction solvent was removed by distillation to obtain a crude product, and the product was recrystallized with dichloromethane to obtain the optically active titanium complex (D).

A faintly yellowish white solid

MS (CSI)=1082, 2163

The optically active titanium-salan complexes (E) and (F) were also obtained by the same method described above.

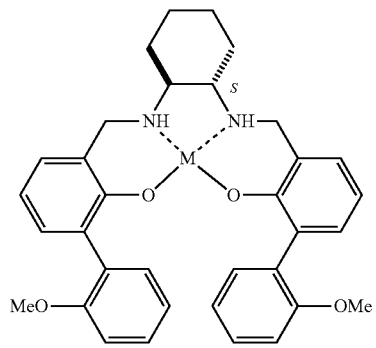

(E)

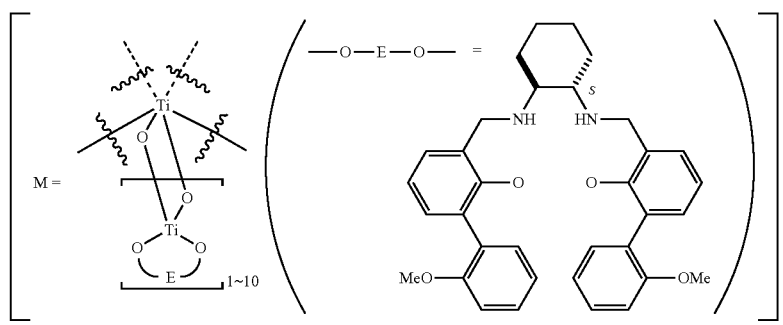

-continued

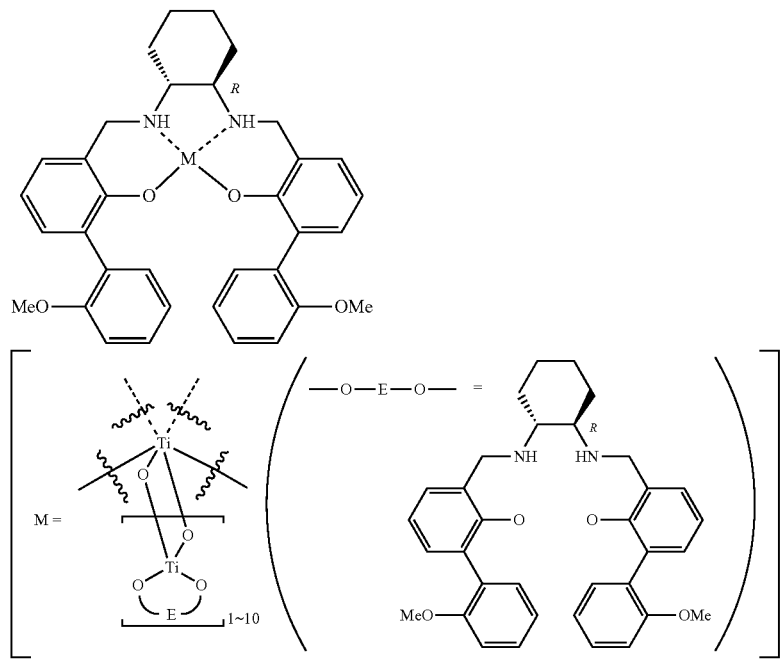

(F)

Example 1

Synthesis of (3S,4S)-6-acetamide-3,4-epoxy-3,4-dihydro-2,2-dimethyl-7-nitro-2H-1-benzopyran (Compound (I))

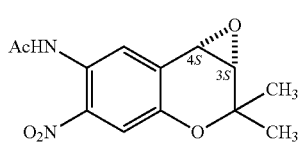

(I)

6-Acetamide-2,2-dimethyl-7-nitro-2H-1-benzopyran (0.54 g, 2.1 mmol) was added to a dichloromethane solution (3 mL) of the optically active titanium-salalen complex (B) (38 mg, 0.021 mmol) (1.0 mol % to a substrate) at 28° C. While stirring the reaction solution, 7.5% hydrogen peroxide aqueous solution (1.4 g, 3.1 mmol) was added at 28° C. for 10 hours. The start time of addition of 7.5% hydrogen peroxide aqueous solution was defined as the reaction start time. After 14 hours from the reaction start time, additional 7.5% hydrogen peroxide aqueous solution (0.1 g, 0.2 mmol) was added at 28° C. and the resultant solution was further stirred for 19 hours after the reaction start time at 28° C. After completion of the reaction, dichloromethane (6 mL) and distilled water (6 mL) were added to the reaction solution, and the organic layer was separated. An organic layer which was extracted from the aqueous layer with dichloromethane (6 mL) and the separated organic layer were combined, and the combined layer was condensed to obtain a crude product. The product was purified by column chromatography to obtain the compound (I) in the form of yellowish powder (0.49 g, yield: 86%, optical purity: 99.9% ee or more). Analytical conditions; Column name: CHIRALPAK OJ-RH, Eluent: acetonitrile/methanol/0.01 M sodium chloride aqueous solution=1/3/5 (v/v/v), Flow rate: 1.5 mL/min, Column temperature: 40° C., Retention time: product of the reaction (3S,4S) 15.9 min, enantiomer (3R,4R) 11.7 min, Measured wavelength: 242 nm.

$^1$H-NMR (CDCl$_3$) δ; 1.27 (s, 3H), 1.59 (s, 3H), 2.28 (s, 3H), 3.55 (d, J=4.1 Hz, 1H), 3.97 (d, J=4.1 Hz, 1H), 7.64 (s, 1H), 8.79 (s, 1H), 10.10 (br, 1H)

Example 2

Synthesis of (3R,4R)-6-acetamide-3,4-epoxy-3,4-dihydro-2,2-dimethyl-7-nitro-2H-1-benzopyran (Compound (II))

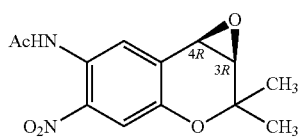

(II)

6-Acetamide-2,2-dimethyl-7-nitro-2H-1-benzopyran (537.4 mg, 2.1 mmol) was added to a dichloromethane solution (3 mL) of the optically active titanium-salalen complex (E) (25.6 mg, 0.021 mmol) (1.0 mol % to a substrate) at 30° C. While stirring the reaction solution, 30% hydrogen peroxide aqueous solution (302.7 mg, 2.7 mmol) was added at 30° C. for 1 second. Then the resultant solution was further stirred for 7 hours at 30° C. After completion of the reaction, dichloromethane and distilled water were added to the reaction solution, and the organic layer was separated. An organic layer which was extracted from the aqueous layer with dichloromethane and the separated organic layer were combined, and the combined layer was condensed to obtain a crude product. The product was purified by column chromatography to obtain the compound (II) in the form of yellowish powder (0.53 g, yield: 93%, optical purity: 99.9% ee or more).

Analytical conditions; Column name: CHIRALPAK OJ-R[H], Eluent: acetonitrile/methanol/0.01 M sodium chloride aqueous solution=1/3/5 (v/v/v), Flow rate: 1.5 mL/min, Column temperature: 40° C., Retention time: product of the reaction (3R,4R) 13.4 min, enantiomer (3S,4S) 17.5 min, Measured wavelength: 242 nm.

$^1$H-NMR (CDCl$_3$) δ; 1.27 (s, 3H), 1.59 (s, 3H), 2.28 (s, 3H), 3.55 (d, J=4.2 Hz, 1H), 3.97 (d, J=4.5 Hz, 1H), 7.63 (s, 1H), 8.79 (s, 1H), 10.09 (br, 1H)

Example 3

Synthesis of (3S,4S)-3,4-epoxy-3,4-dihydro-2,2-dimethyl-6-nitro-2H-1-benzopyran (Compound (III))

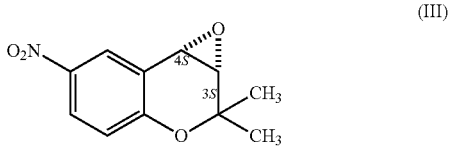 [SMILES: CC1(C)Oc2ccc([N+](=O)[O-])cc2[C@@H]2O[C@@H]21]

(III)

2,2-Dimethyl-6-nitro-2H-1-benzopyran (0.41 g, 2.0 mmol) was added to a dichloromethane solution (8 mL) of the optically active titanium-salalen complex (B) (73 mg, 0.041 mmol) (2.0 mol % to a substrate) at 25° C. While stirring the reaction solution, 30% hydrogen peroxide aqueous solution (0.24 g, 2.1 mmol) was added at 25° C. for 2 seconds. The start time of addition of 30% hydrogen peroxide aqueous solution was defined as the reaction start time. The resultant solution was stirred for 27 hours from the reaction start time at 25° C. After completion of the reaction, dichloromethane (6 mL) and distilled water (6 mL) were added to the reaction solution, and the organic layer was separated. An organic layer which was extracted from the aqueous layer with dichloromethane and the separated organic layer were combined, and the combined layer was condensed to obtain a crude product. The product was purified by column chromatography to obtain the compound (III) in the form of whitish yellow powder (0.43 g, yield: 97%, optical purity: 99.9% ee or more). Analytical conditions; Column name: CHIRALCEL OD-H, Eluent: n-hexane/i-propanol=9/1 (v/v), Flow rate: 1.0 mL/min, Column temperature: 40° C., Retention time: product of the reaction (3S,4S) 9.6 min, enantiomer (3R,4R) 8.4 min, Measured wavelength: 300 nm.

$^1$H-NMR (CDCl$_3$) δ; 1.33 (s, 3H), 1.63 (s, 3H), 3.57 (d, J=4.4 Hz, 1H), 4.00 (d, J=4.4 Hz, 1H), 6.89 (d, J=9.1 Hz, 1H), 8.15 (dd, J=9.1, 2.8 Hz, 1H), 8.31 (d, J=2.8 Hz, 1H)

Example 4

Synthesis of (3S,4S)-3,4-epoxy-3,4-dihydro-2,2-dimethyl-6-nitro-2H-1-benzopyran (Compound (III))

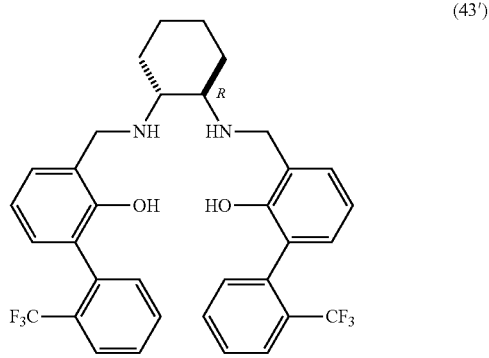

(43')

Titanium tetraisopropoxide, (Ti(Oi-Pr)$_4$), (2.3 mg, 0.0080 mmol) was added to a dichloromethane solution (0.3 mL) of the salan ligand (4.9 mg, 0.0080 mmol) (4.0 mol % to a substrate) represented by the formula (43') at 20° C. After 1 hour stirring at 20° C., 2,2-dimethyl-6-nitro-2H-1-benzopyran (41 mg, 0.20 mmol) was added to the solution. 30% hydrogen peroxide aqueous solution (0.034 g, 0.30 mmol) was divided into three equal portions and, while stirring the reaction solution, the first addition was conducted at 20° C., and after 30 minutes, the second addition was conducted, and after 1 hour, the third addition was conducted. The start time of the first addition of 30% hydrogen peroxide aqueous solution was defined as the reaction start time. The resultant solution was stirred for 24 hours from the reaction start time at 20° C. and the reaction solution sample was taken. The reaction conversion rate of the taken sample was analyzed with HPLC. The conversion rate to the compound (III) was 99% or more and the optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction (3S,4S) 15.8 min, enantiomer (3R,4R) 12.6 min, Measured wavelength: 330 nm.

Example 5

Synthesis of (3R,4R)-3,4-epoxy-3,4-dihydro-2,2-dimethyl-6-nitro-2H-1-benzopyran (Compound (IV))

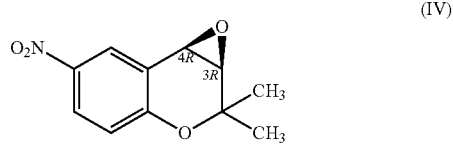 [SMILES: CC1(C)Oc2ccc([N+](=O)[O-])cc2[C@H]2O[C@H]21]

(IV)

2,2-Dimethyl-6-nitro-2H-1-benzopyran (0.41 g, 2.0 mmol) was added to a dichloromethane solution (6 mL) of the optically active titanium-salan complex (E) (48 mg, 0.040 mmol) (2.0 mol % to a substrate) at 20° C. 30% hydrogen peroxide aqueous solution (0.24 g, 2.1 mmol) was divided into three equal portions and, while stirring the reaction solution, the first addition was conducted at 20° C., and after 30 minutes, the second addition was conducted, and after 1 hour, the third addition was conducted. The start time of the first addition of 30% hydrogen peroxide aqueous solution was defined as the reaction start time. After the resultant solution was stirred for 24 hours from the reaction start time at 20° C., dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (IV) in the form of whitish yellow powder (0.41 g, yield: 94%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction (3R,4R) 12.6 min, enantiomer (3S,4S) 15.8 min, Measured wavelength: 330 nm.

$^1$H-NMR (CDCl$_3$) δ; 1.33 (s, 3H), 1.62 (s, 3H), 3.58 (d, J=4.4 Hz, 1H), 4.00 (d, J=4.4 Hz, 1H), 6.89 (d, J=8.6 Hz, 1H), 8.14 (dd, J=8.6, 3.0 Hz, 1H), 8.30 (d, J=3.0 Hz, 1H)

Example 6

Synthesis of (3R,4R)-3,4-epoxy-3,4-dihydro-2,2-dimethyl-6-nitro-2H-1-benzopyran (Compound (IV))

2,2-Dimethyl-6-nitro-2H-1-benzopyran (0.41 g, 2.0 mmol) was added to a dichloromethane solution (8 mL) of the optically active titanium-salalen complex (A) (73 mg, 0.041 mmol) (2.0 mol % to a substrate) at 25° C. While stirring the reaction solution, 30% hydrogen peroxide aqueous solution (0.24 g, 2.1 mmol) was added at 25° C. for 2 seconds. After the addition, the solution was continued to stir at 25° C. The start time of the addition of 30% hydrogen peroxide aqueous solution was defined as the reaction start time. After 8 hours from the reaction start time, the reaction solution sample was taken and the reaction conversion rate of the taken sample was analyzed with HPLC. The conversion rate to the compound (IV) was 99% or more and the optical purity was 96% ee.

Analytical conditions; Column name: CHIRALPAK AD-RH, Eluent: acetonitrile/20 mM (pH8) phosphate buffer solution=6/4 (v/v), Flow rate: 1.0 mL/min, Column temperature: 40° C., Retention time: product of the reaction (3R,4R) 5.2 min, enantiomer (3S,4S) 6.1 min, Measured wavelength: 330 mm.

Example 7

Synthesis of (3S*,4S*)-3,4-epoxy-3,4-dihydro-2,2-dimethyl-7-nitro-6-methoxy-2H-1-benzopyran (Compound (V), * Represents a Relative Configuration)

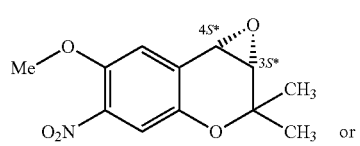

(V)

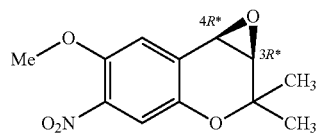

(V')

2,2-Dimethyl-7-nitro-6-methoxy-2H-1-benzopyran (0.47 mg, 2.0 mmol) was added to a dichloromethane solution (8 mL) of the optically active titanium-salalen complex (B) (71 mg, 0.040 mmol) (2.0 mol % to a substrate) at 25° C. While stirring the reaction solution, 30% hydrogen peroxide aqueous solution (0.24 g, 2.1 mmol) was added at 25° C. for 2 seconds. The start time of addition of 30% hydrogen peroxide aqueous solution was defined as the reaction start time. The resultant solution was further stirred for 19 hours from the reaction start time at 25° C. After completion of the reaction, dichloromethane (3 mL) and distilled water (3 mL) were added to the reaction solution, and the organic layer was separated. An organic layer which was extracted from an aqueous layer with dichloromethane (3 mL) and the separated organic layer were combined, and the combined layer was condensed to obtain a crude product. The product was purified by column chromatography to obtain the compound (V) in the form of yellowish oil (0.50 g, yield: 99%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 0.8 mL/min, Column temperature: 40° C., Retention time: product of the reaction 12.1 min, enantiomer 11.3 min, Measured wavelength: 225 nm.

$^1$H-NMR (CDCl$_3$) δ; 1.26 (s, 3H), 1.59 (s, 3H), 3.53 (d, J=4.4 Hz, 1H), 3.90 (d, J=4.4 Hz, 1H), 3.95 (s, 3H), 7.08 (s, 1H), 7.33 (s, 1H)

Example 8

Synthesis of (3S*,4S*)-3,4-epoxy-3,4-dihydro-2,2-dimethyl-7-nitro-6-methoxy-2H-1-benzopyran (Compound (V), * Represents a Relative Configuration)

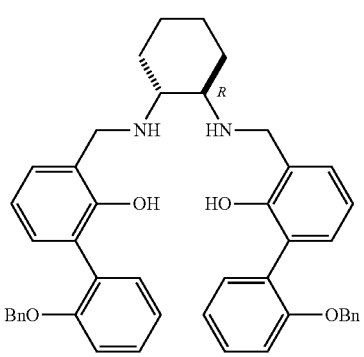

(41')

Titanium tetraisopropoxide, (Ti(Oi-Pr)$_4$), (5.7 mg, 0.020 mmol) was added to a dichloromethane solution (0.9 mL) of the salan ligand (14 mg, 0.020 mmol) represented by the formula (41') at 20° C. After 1 hour stirring at 20° C., 2,2-dimethyl-7-nitro-6-methoxy-2H-1-benzopyran (0.118 g, 0.50 mmol) was added to the solution. 30% hydrogen peroxide aqueous solution (0.085 g, 0.75 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. The resultant solution was stirred for 24 hours from the reaction start time at 20° C. and the reaction solution sample was taken. The reaction conversion rate of the taken sample was analyzed with HPLC. The conversion rate to the compound (V) was 99% or more and an optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 18.3 min, enantiomer 17.5 min, Measured wavelength: 225 nm.

Example 9

Synthesis of (3R*,4R*)-3,4-epoxy-3,4-dihydro-2,2-dimethyl-7-nitro-6-methoxy-2H-1-benzopyran (Compound (V'), * Represents a Relative Configuration)

2,2-Dimethyl-7-nitro-6-methoxy-2H-1-benzopyran (0.47 g, 2.0 mmol) was added to a dichloromethane solution (7 mL) of the optically active titanium-salan complex (E) (48 mg, 0.040 mmol) (2.0 mol % to a substrate) at 25° C. 30% hydrogen peroxide aqueous solution (0.24 g, 2.1 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After the resultant solution was stirred for 24 hours from the reaction start time at 20° C., dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (V') in the form of yellowish oil (0.48 g, yield: 96%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 17.5 min, enantiomer 18.3 min, Measured wavelength: 225 nm.

$^1$H-NMR (CDCl$_3$) δ; 1.26 (s, 3H), 1.58 (s, 3H), 3.54 (d, J=4.5 Hz, 1H), 3.91 (d, J=4.5 Hz, 1H), 3.95 (s, 3H), 7.09 (s, 1H), 7.32 (s, 1H)

Example 10

(3R*,4R*)-3,4-epoxy-3,4-dihydro-2,2-dimethyl-7-nitro-6-methoxy-2H-1-benzopyran (Compound (V'), * Represents a Relative Configuration)

2,2-Dimethyl-7-nitro-6-methoxy-2H-1-benzopyran (0.47 mg, 2.0 mmol) was added to a dichloromethane solution (8 mL) of the optically active titanium-salalen complex (A) (71 mg, 0.040 mmol) (2.0 mol % to a substrate) at 25° C. While stirring the reaction solution, 30% hydrogen peroxide aqueous solution (0.24 g, 2.1 mmol) was added at 25° C. for 2 second. The start time of addition of 30% hydrogen peroxide aqueous solution was defined as the reaction start time. After 18 hours from the reaction start time, a reaction solution sample was taken. The reaction conversion rate of the taken sample was analyzed with HPLC. The conversion rate to the compound (V') was 99% or more and the optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 0.8 mL/min, Column temperature: 40° C., Retention time: product of the reaction 11.3 min, enantiomer 12.1 min, Measured wavelength: 225 nm.

Example 11

Synthesis of (3S*,4S*)-3,4-epoxy-3,4-dihydro-2,2-dimethyl-7-nitro-2H-1-benzopyran (Compound (VI), * Represents a Relative Configuration)

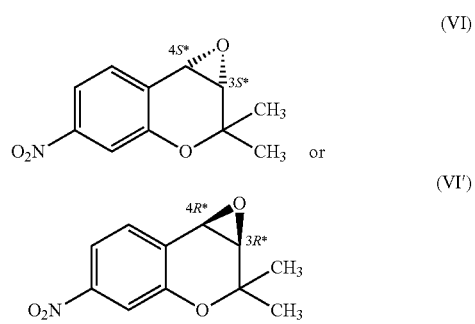

2,2-Dimethyl-7-nitro-2H-1-benzopyran (0.21 mg, 1.0 mmol) was added to a dichloromethane solution (4 mL) of the optically active titanium-salalen complex (B) (36 mg, 0.020 mmol) (2.0 mol % to a substrate) at 25° C. While stirring the reaction solution, 30% hydrogen peroxide aqueous solution (0.12 g, 1.1 mmol) was added for 2 second. The start time of addition of 30% hydrogen peroxide aqueous solution was defined as the reaction start time. The resultant solution was stirred for 27 hours from the reaction start time at 25° C. After completion of the reaction, dichloromethane (2 mL) and distilled water (2 mL) were added to the reaction solution, and the organic layer was separated. An organic layer which was extracted from the aqueous layer with dichloromethane (2 mL) and the separated organic layer were combined, and the combined layer was condensed to obtain a crude product. The product was purified by column chromatography to obtain the compound (VI) in the form of yellowish powder (0.43 g, yield: 99%, optical purity: 99.4% ee).

Analytical conditions; Column name: CHIRALPAK AD-RH, Eluent: acetonitrile/20 mM (pH8) phosphate buffer solution=6/4 (v/v), Flow rate: 1.0 mL/min, Column temperature: 40° C., Retention time: product of the reaction 9.2 min, enantiomer 4.9 min, Measured wavelength: 220 nm.

$^1$H-NMR (CDCl$_3$) δ; 1.29 (s, 3H), 1.62 (s, 3H), 3.58 (d, J=4.4 Hz, 1H), 3.97 (d, J=4.4 Hz, 1H), 7.50 (d, J=8.3 Hz, 1H), 7.67 (dd, J=8.3, 2.2 Hz, 1H), 7.80 (d, J=2.2 Hz, 1H)

Example 12

Synthesis of (3S*,4S*)-3,4-epoxy-3,4-dihydro-2,2-dimethyl-7-nitro-2H-1-benzopyran (Compound (VI), * Represents a Relative Configuration)

2,2-Dimethyl-7-nitro-2H-1-benzopyran (0.41 g, 2.0 mmol) was added to a dichloromethane solution (6 mL) of the optically active titanium-salan complex (F) (48 mg, 0.040 mmol) (2.0 mol % to a substrate) at 25° C. 30% hydrogen peroxide aqueous solution (0.25 g, 2.2 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. The resultant solution was stirred for 24 hours from the reaction start time at 20° C. After completion of the reaction, dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (VI) in the form of yellowish crystal (0.44 g, yield: 98%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction 25.2 min, enantiomer 13.9 min, Measured wavelength: 220 nm.

$^1$H-NMR (CDCl$_3$) δ; 1.29 (s, 3H), 1.61 (s, 3H), 3.60 (d, J=4.5 Hz, 1H), 3.99 (d, J=4.5 Hz, 1H), 7.52 (d, J=8.3 Hz, 1H), 7.62 (d, J=2.1 Hz, 1H), 7.70 (dd, J=8.3, 2.1 Hz, 1H)

Example 13

Synthesis of (3R*,4R*)-3,4-epoxy-3,4-dihydro-2,2-dimethyl-7-nitro-2H-1-benzopyran (Compound (VI), * Represents a Relative Configuration)

2,2-Dimethyl-7-nitro-2H-1-benzopyran (0.21 mg, 1.0 mmol) was added to a dichloromethane solution (4 mL) of the optically active titanium-salalen complex (A) (36 mg, 0.020 mmol) (2.0 mol % to a substrate) at 25° C. While stirring the reaction solution, 30% hydrogen peroxide aqueous solution (0.12 g, 1.1 mmol) was added at 25° C. for 2 second. Then, the reaction solution was continued to stir at 25° C. The start time of addition of 30% hydrogen peroxide aqueous solution was defined as the reaction start time. After 24 hours from the reaction start time, a reaction solution sample was taken. The reaction conversion rate of the taken sample was analyzed with HPLC. The conversion rate to the compound (VI') was 99% or more and an optical purity was 99% ee.

Analytical conditions; Column name: CHIRALPAK AD-RH, Eluent: acetonitrile/20 mM (pH8) phosphate buffer solution=6/4 (v/v), Flow rate: 1.0 mL/min, Column temperature: 40° C., Retention time: product of the reaction 4.9 min, enantiomer 9.2 min, Measured wavelength: 220 nm.

Example 14

Synthesis of (3R*,4R*)-3,4-epoxy-3,4-dihydro-2,2-dimethyl-7-nitro-2H-1-benzopyran (Compound (VI'), * Represents a Relative Configuration)

2,2-Dimethyl-7-nitro-2H-1-benzopyran (0.205 g, 1.0 mmol) was added to a dichloromethane solution (3 mL) of the optically active titanium-salan complex (E) (24 mg, 0.020 mmol) (2.0 mol % to a substrate) at 20° C. 30% hydrogen peroxide aqueous solution (0.12 g, 1.1 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After stirring the solution for 24 hours from the reaction start time at 20° C., a reaction solution sample was taken. The reaction conversion rate of the taken sample was analyzed with HPLC. The conversion rate to the compound (VI') was 99% or more and an optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction 13.9 min, enantiomer 25.2 min, Measured wavelength: 220 nm.

Example 15

Synthesis of (3S*,4S*)-3,4-epoxy-6-fluoro-3,4-dihydro-2,2-dimethyl-8-nitro-2H-1-benzopyran (Compound (VII), * Represents a Relative Configuration)

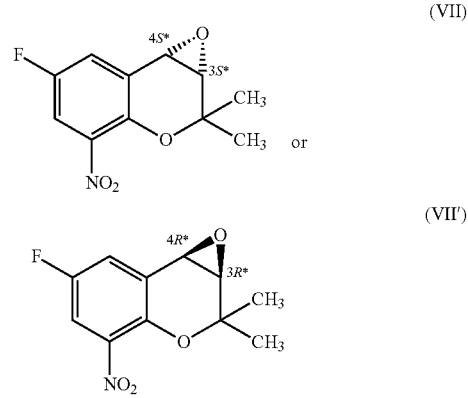

6-Fluoro-2,2-dimethyl-8-nitro-2H-1-benzopyran (0.23 g, 1.0 mmol) was added to a dichloromethane solution (4 mL) of the optically active titanium-salalen complex (B) (37 mg, 0.021 mmol) (2.0 mol % to a substrate) at 25° C. While stirring the reaction solution, 30% hydrogen peroxide aqueous solution (0.12 g, 1.1 mmol) was added at 25° C. for 2 second. The start time of the addition of 30% hydrogen peroxide aqueous solution was defined as the reaction start time. The resultant solution was stirred for 29 hours from the reaction start time at 25° C. After completion of the reaction, dichloromethane (2 mL) and distilled water (2 mL) were added to the reaction solution, and the organic layer was separated. An organic layer which was extracted from the aqueous layer with dichloromethane (2 mL) and the separated organic layer were combined, and the combined layer was condensed to obtain a crude product. The product was purified by column chromatography to obtain the compound (VII) in the form of yellowish powder (0.23 g, yield: 94%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 17.4 min, enantiomer 18.1 min, Measured wavelength: 220 nm.

$^1$H-NMR (CDCl$_3$) δ; 1.33 (s, 3H), 1.64 (s, 3H), 3.57 (d, J=4.4 Hz, 1H), 3.94 (d, J=4.4 Hz, 1H), 7.35 (dd, J=4.4, 7.1 Hz, 1H), 7.56 (dd, J=4.4, 7.9 Hz, 1H)

Example 16

Synthesis of (3S*,4S*)-3,4-epoxy-6-fluoro-3,4-dihydro-2,2-dimethyl-8-nitro-2H-1-benzopyran (Compound (VII), * Represents a Relative Configuration)

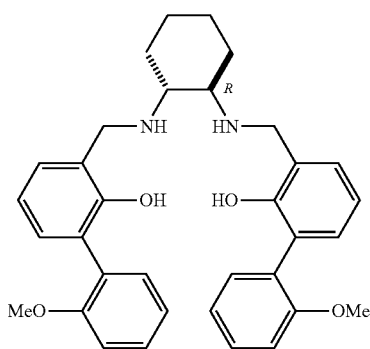

(44')

Titanium tetraisopropoxide, (Ti(Oi-Pr)$_4$), (11 mg, 0.040 mmol) was added to a dichloromethane solution (1.7 mL) of the salan ligand (43 mg, 0.080 mmol) (4.0 mol % to a substrate) represented by the formula (44') at 25° C. After 1 hour stirring at 20° C., 6-fluoro-2,2-dimethyl-8-nitro-2H-1-benzopyran (0.446 g, 2.0 mmol) was added to the solution. 30% hydrogen peroxide aqueous solution (0.25 g, 2.2 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. The resultant solution was stirred for 40 hours from the reaction start time at 20° C. After completion of the reaction, dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (VII) in the form of yellowish oil (0.43 g, yield: 90%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 16.8 min, enantiomer 17.3 min, Measured wavelength: 220 nm.

$^1$H-NMR (CDCl$_3$) δ; 1.33 (s, 3H), 1.63 (s, 3H), 3.60 (d, J=4.5 Hz, 1H), 3.98 (d, J=4.5 Hz, 1H), 7.38 (dd, J=3.0, 7.4 Hz, 1H), 7.54 (dd, J=3.0, 7.4 Hz, 1H)

Example 17

Synthesis of (3R*,4R*)-3,4-epoxy-6-fluoro-3,4-dihydro-2,2-dimethyl-8-nitro-2H-1-benzopyran (Compound (VII'), * Represents a Relative Configuration)

6-Fluoro-2,2-dimethyl-8-nitro-2H-1-benzopyran (0.23 g, 1.0 mmol) was added to a dichloromethane solution (4 mL) of the optically active titanium-salalen complex (A) (37 mg, 0.021 mmol) (2.0 mol % to a substrate) at 25° C. While stirring the reaction solution, 30% hydrogen peroxide aqueous solution (0.12 g, 1.1 mmol) was added at 25° C. for 2 second. The start time of the addition of 30% hydrogen peroxide aqueous solution was defined as the reaction start time. After 3 hours from the reaction start time, a reaction solution sample was taken. The reaction conversion rate of the taken sample was analyzed with HPLC. The conversion rate to the compound (VII') was 76% and an optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 18.1 min, enantiomer 17.4 min, Measured wavelength: 220 nm.

Example 18

Synthesis of (3R*,4R*)-3,4-epoxy-6-fluoro-3,4-dihydro-2,2-dimethyl-8-nitro-2H-1-benzopyran (Compound (VII'), * Represents a Relative Configuration)

6-Fluoro-2,2-dimethyl-8-nitro-2H-1-benzopyran (0.23 g, 1.0 mmol) was added to a dichloromethane solution (3 mL) of the optically active titanium-salan complex (E) (24 mg, 0.020 mmol) (2.0 mol % to a substrate) at 20° C. 30% hydrogen peroxide aqueous solution (0.12 g, 1.1 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After stirring the solution for 24 hours from the reaction start time at 20° C., a reaction solution sample was taken. The reaction conversion rate of the taken sample was analyzed with HPLC. The conversion rate to the compound (VII') was 96% and an optical purity was 99% ee or more. Analytical conditions; Column name: CHIRALPAK AD-RH (three columns are serially connected), Eluent: acetonitrile/20 mM (pH8) phosphate buffer solution=6/4 (v/v), Flow rate: 0.5 mL/min, Column temperature: 40° C., Retention time: product of the reaction 17.3 min, enantiomer 16.8 min, Measured wavelength: 220 nm.

Example 19

Synthesis of (3R*,4R*)-(3,4-epoxy-2,2,9-trimethyl-3,4-dihydro-2H-pyrano(2,3-g)quinolin-7-yl)-methyl acetate (Compound (VIII'), * Represents a Relative Configuration)

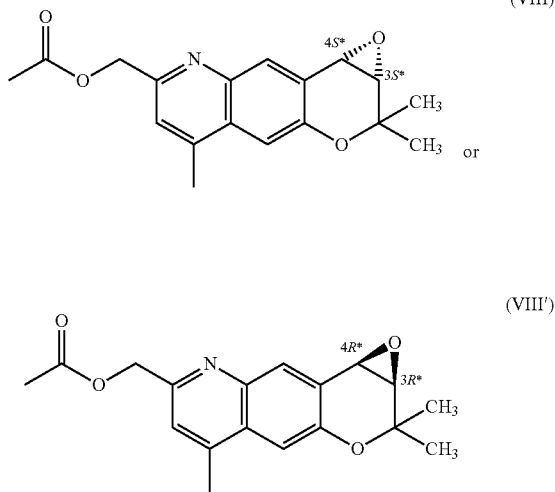

(2,2,9-Trimethyl-2H-pyrano(2,3-g)quinolin-7-yl)-methyl acetate (0.61 g, 2.1 mmol) was added to a dichloromethane solution (3 mL) of the optically active titanium-salalen complex (A) (71 mg, 0.040 mmol) (1.9 mol % to a substrate) at 28° C. While stirring the reaction solution, 7.5% hydrogen peroxide aqueous solution (1.4 g, 3.1 mmol) was added at 28° C. for 10 hours. The start time of addition of 7.5% hydrogen peroxide aqueous solution was defined as the reaction start time. After 12 hours from the reaction start time, additional 7.5% hydrogen peroxide aqueous solution (0.1 g, 0.2 mmol) was added at 28° C., and then the resultant solution was stirred at 28° C. for 14 hours after the reaction start time. After completion of the reaction, dichloromethane (6 mL) and distilled water (6 mL) were added to the reaction solution, and the organic layer was separated. An organic layer which was extracted from the aqueous layer with dichloromethane (6 mL) and the separated organic layer were combined, and the combined layer was condensed to obtain a crude product. The product was purified by column chromatography to obtain the compound (VIII') in the form of yellowish oil (0.65 g, yield: 99%, optical purity: 99.9% ee or more).

Analytical conditions; Column name: CHIRALPAK AD-RH, Eluent: acetonitrile/20 mM (pH8) phosphate buffer solution=6/4 (v/v), Flow rate: 1.0 mL/min, Column temperature: 40° C., Retention time: product of the reaction 3.9 min, enantiomer 9.3 min, Measured wavelength: 254 nm.

$^1$H-NMR (CDCl$_3$) δ; 1.30 (s, 3H), 1.65 (s, 3H), 2.19 (s, 3H), 2.62 (d, J=0.8 Hz, 3H), 3.61 (d, J=4.4 Hz, 1H), 4.15 (d, J=4.4 Hz, 1H), 5.30 (s, 2H), 7.26 (s, 1H), 7.32 (s, 1H), 8.10 (s, 1H)

Example 20

Synthesis of (3S*,4S*)-(3,4-epoxy-2,2,9-trimethyl-3,4-dihydro-2H-pyrano(2,3-g)quinolin-7-yl)-methyl acetate (Compound (VIII), * Represents a Relative Configuration)

(2,2,9-Trimethyl-2H-pyrano(2,3-g)quinolin-7-yl)-methyl acetate (34.2 mg, 0.12 mmol) was added to a dichloromethane solution (1.2 mL) of the optically active titanium-salan complex (D) (6.2 mg, 0.006 mmol) (5.0 mol % to a substrate) at 28° C. While stirring the reaction solution, 30% hydrogen peroxide aqueous solution (8.5 mg, 0.075 mmol) was added at 28° C. for 1 second. The start time of addition of 30% hydrogen peroxide aqueous solution was defined as the reaction start time. After 20 minutes from the reaction start time, additional 30% hydrogen peroxide aqueous solution (8.5 mg, 0.075 mmol) was added for 1 second at 28° C. The resultant solution was continued to stir at 28° C., and, after 3 hours, a reaction solution sample was taken. The reaction conversion rate of the taken sample was analyzed with HPLC. The conversion rate to the compound (VIII) was 80% and the optical purity was 99% ee.

Analytical conditions; Column name: CHIRALPAK AD-RH, Eluent: acetonitrile/20 mM (pH8) phosphate buffer solution=6/4 (v/v), Flow rate: 1.0 mL/min, Column temperature: 40° C., Retention time: product of the reaction 10.2 min, enantiomer 4.1 min, Measured wavelength: 254 nm

Example 21

Synthesis of (3R*,4R*)-(3,4-epoxy-2,2,9-trimethyl-3,4-dihydro-2H-pyrano(2,3-g)quinolin-7-yl)-methyl acetate (Compound (VIII'), * Represents a Relative Configuration)

(2,2,9-Trimethyl-2H-pyrano(2,3-g)quinolin-7-yl)-methyl acetate (0.595 g, 2.0 mmol) was added to a dichloromethane solution (4 mL) of the optically active titanium-salan complex (E) (48 mg, 0.040 mmol) (2.0 mol % to a substrate) at 20° C. 30% hydrogen peroxide aqueous solution (0.34 g, 3.0 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. The resultant solution was stirred for 24 hours after the reaction start time at 20° C. After completion of the reaction, dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (VIII') in the form of yellowish powder (0.61 g, yield: 97%, optical purity: 99.3% ee).

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction 11.2 min, enantiomer 26.6 min, Measured wavelength: 320 nm.

$^1$H-NMR (CDCl$_3$) δ; 1.30 (s, 3H), 1.65 (s, 3H), 2.19 (s, d, J=1.9 Hz, 3H), 2.60 (s, 3H), 3.60 (dd, J=4.5 Hz, 1.9 Hz, 1H), 4.14 (d, J=4.5 Hz, 1H), 5.30 (s, 2H), 7.25 (s, 1H), 7.31 (s, 1H), 8.10 (s, 1H)

Example 22

Synthesis of (3S*,4S*)-7-chloro-3,4-epoxy-2,2,9-trimethyl-3,4-dihydro-2H-pyrano(2,3-g)quinoline (Compound (IX), * Represents a Relative Configuration)

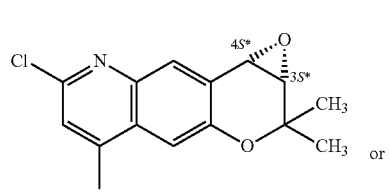

(IX)

or

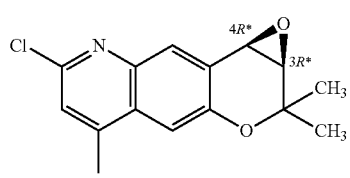

(IX')

7-Chloro-2,2,9-trimethyl-2H-pyrano(2,3-g)quinoline (0.26 g, 1.0 mmol) was added to a dichloromethane solution (2 mL) of the optically active titanium-salan complex (F) (120 mg, 0.10 mmol) (10 mol % to a substrate) at 20° C. 30% hydrogen peroxide aqueous solution (0.17 g, 1.5 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. The resultant solution was stirred for 26 hours from the reaction start time at 20° C. After completion of the reaction, dichloromethane (5 mL) and distilled water (5 mL) were added to the reaction solution, and the organic layer was separated. Organic layers which were extracted twice from the aqueous layer with dichloromethane (5 mL and 3 mL) and the separated organic layer were combined, and the combined layer was condensed to obtain a crude product. The product was purified by column chromatography to obtain the compound (IX) in the form of faintly yellowish powder (0.21 g, yield: 77%, optical purity: 99.9% ee or more).

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction 42.1 min, enantiomer 21.7 min, Measured wavelength: 220 nm.

$^1$H-NMR (CDCl$_3$) δ; 1.30 (s, 3H), 1.64 (s, 3H), 2.56 (s, 3H), 3.61 (d, J=4.2 Hz, 1H), 4.13 (d, J=4.2 Hz, 1H), 7.15 (s, 1H), 7.27 (s, 1H), 8.00 (s, 1H)

Example 23

Synthesis of (3R*,4R*)-7-chloro-3,4-epoxy-2,2,9-trimethyl-3,4-dihydro-2H-pyrano(2,3-g)quinoline (Compound (IX'), * Represents a Relative Configuration)

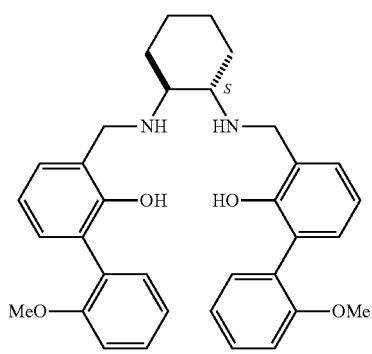

(44)

Titanium tetraisopropoxide, (Ti(Oi-Pr)$_4$), (2.8 mg, 0.010 mmol) was added to a dichloromethane solution (0.5 mL) of the salan ligand (27 mg, 0.050 mmol) (10 mol % to a substrate) represented by the formula (44) at 20° C. After 1 hour string at 20° C., 7-chloro-2,2,9-trimethyl-2H-pyrano(2,3-g) quinoline (0.130 g, 0.50 mmol) and dichloromethane (1 mL) were added to the solution. 30% hydrogen peroxide aqueous solution (0.085 g, 0.75 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After stirring the solution for 45 hours from the reaction start time at 20° C., a reaction solution sample was taken. The reaction conversion rate of the taken sample was analyzed with HPLC. The conversion rate to the compound (IX') was 99% or more and an optical purity was 99% ee.

Analytical conditions; Column name: CHIRALPAK AD-RH (three columns are serially connected), Eluent: acetonitrile/20 mM (pH8) phosphate buffer solution=6/4 (v/v), Flow rate: 1.0 mL/min, Column temperature: 40° C., Retention time: product of the reaction 21.7 min, enantiomer 42.1 min, Measured wavelength: 220 nm.

Example 24

Synthesis of (3S*,4S*)-3,4-epoxy-3,4-dihydro-2,2-dimethyl-7-dimethanesulfonylamino-6-methoxy-2H-1-benzopyran (Compound (X), * Represents a Relative Configuration)

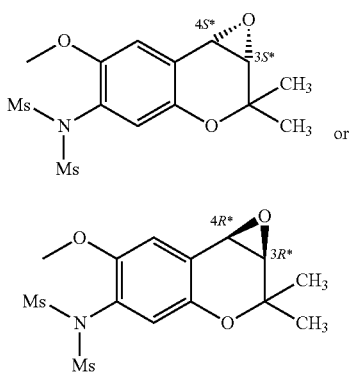

2,2-Dimethyl-7-dimethanesulfonylamino-6-methoxy-2H-1-benzopyran (0.18 g, 0.50 mmol) was added to a dichloromethane solution (1 mL) of the optically active titanium-salan complex (F) (12 mg, 0.010 mmol) (2.0 mol % to a substrate) at 20° C. 30% hydrogen peroxide aqueous solution (0.085 g, 0.75 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After the resultant solution was stirred for 30 hours from the reaction start time at 20° C., dichloromethane (2 mL) and distilled water (2 mL) were added to the reaction solution, and the organic layer was separated. Organic layers which were extracted twice from the aqueous layer with dichloromethane (2 mL and 1 mL) and the separated organic layer were combined, and the combined layer was condensed to obtain a crude product. The product was purified by column chromatography to obtain the compound (X) in the form of white powder (0.18 g, yield: 97.5%, optical purity: 99% ee).

Analytical conditions; Column name: CHIRALPAK AD-RH (three columns are serially connected), Eluent: acetonitrile/20 mM (pH8) phosphate buffer solution=3/7 (v/v), Flow rate: 1.0 mL/min, Column temperature: 40° C., Retention time: product of the reaction 19.8 min, enantiomer 18.6 min, Measured wavelength: 320 nm.

$^1$H-NMR (CDCl$_3$) δ; 1.26 (s, 3H), 1.55 (s, 3H), 3.35 (s, 3H), 3.42 (s, 3H), 3.49 (d, J=4.5 Hz, 1H), 3.88 (s, 3H), 3.88 (d, J=4.5 Hz, 1H), 6.77 (s, 1H), 7.00 (s, 1H)

Example 25

Synthesis of (3R*,4R*)-3,4-epoxy-3,4-dihydro-2,2-dimethyl-7-dimethanesulfonylamino-6-methoxy-2H-1-benzopyran (Compound (X'), * Represents a Relative Configuration)

2,2-Dimethyl-7-dimethanesulfonylamino-6-methoxy-2H-1-benzopyran (72 mg, 0.20 mmol) was added to a dichloromethane solution (1 mL) of the optically active titanium-salan complex (E) (12 mg, 0.010 mmol) (2.0 mol % to a substrate) at 20° C. 30% hydrogen peroxide aqueous solution (0.034 g, 0.30 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After the solution was stirred for 48 hours from the reaction start time at 20° C., a reaction solution sample was taken. The reaction conversion rate of the taken sample was analyzed with HPLC. The conversion rate to the compound (X') was 99% and an optical purity was 99% ee.

Analytical conditions; Column name: CHIRALPAK AD-RH (three columns are serially connected), Eluent: acetonitrile/20 mM (pH8) phosphate buffer solution=3/7 (v/v), Flow rate: 1.0 mL/min, Column temperature: 40° C., Retention time: product of the reaction 18.5 min, enantiomer 20.0 min, Measured wavelength: 320 nm.

Example 26

Synthesis of (3S*,4S*)-3,4-epoxy-3,4-dihydro-2,2-dimethyl-7-dimethanesulfonylamino-6-methoxy-2H-1-benzopyran (Compound (X), * Represents a Relative Configuration)

2,2-Dimethyl-7-dimethanesulfonylamino-6-methoxy-2H-1-benzopyran (72 mg, 0.20 mmol) was added to a dichloromethane solution (0.5 mL) of the optically active titanium-salalen complex (C) (16 mg, 0.010 mmol) (2.0 mol % to a substrate) at 20° C. 30% hydrogen peroxide aqueous solution (0.034 g, 0.30 mmol) was divided into three equal portions and, while stirring the reaction solution, the first addition was conducted at 20° C., and after 30 minutes, the second addition was conducted, and after 1 hour, the third addition was conducted. The time of the first addition of 30% hydrogen peroxide aqueous solution was defined as the reaction start time. After the solution was stirred for 24 hours from the reaction start time at 20° C., a reaction solution sample was taken. The reaction conversion rate of the taken sample was analyzed with HPLC. The conversion rate to the compound (X) was 83% and the optical purity was 99% ee.

Analytical conditions; Column name: CHIRALPAK AD-RH (three columns are serially connected), Eluent: acetonitrile/20 mM (pH8) phosphate buffer solution=3/7 (v/v), Flow rate: 1.0 mL/min, Column temperature: 40° C., Retention time: product of the reaction 19.8 min, enantiomer 18.6 min, Measured wavelength: 320 nm.

INDUSTRIAL APPLICABILITY

According to the present invention, an optically active chromeneoxide compound having high optical purity of 99% ee or more can be obtained in high yield of 90% or more without a separation operation for optical resolution of a target compound, and this compound can be sufficiently used for an important intermediate for a benzopyran compound being effective in the treatment of arrhythmia. Therefore, the present invention is industrially useful.

The invention claimed is:
1. A process for producing an optically active chromene oxide compound represented by formula (14), formula (15), formula (16) or formula (17):

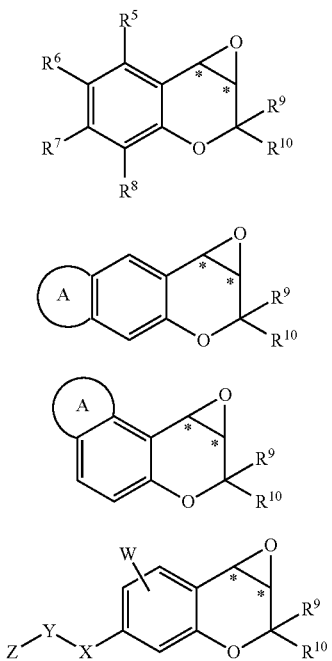

(14)

(15)

(16)

(17)

(wherein $R^5$, $R^6$, $R^7$, $R^8$, $R^9$, $R^{10}$, A, W, X, Y and Z are the same as described below and an absolute configuration of the carbon atoms indicated by * are (R) or (S)), the process comprising:

asymmetrically epoxidizing a chromene compound represented by formula (10), formula (11), formula (12) or formula (13) with an oxidizing agent in a solvent;

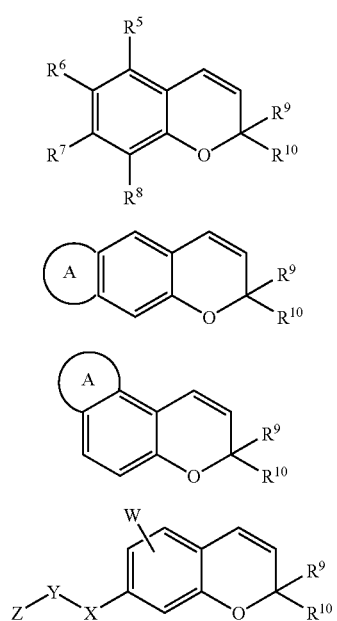

(10)

(11)

(12)

(13)

(wherein $R^5$, $R^6$, $R^7$ and $R^8$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom, $C_{6-10}$ aryl group (the $C_{6-10}$ aryl group may be optionally substituted with a halogen atom, hydroxy group, cyano group, nitro group, $C_{1-4}$ alkyl group or $C_{1-4}$ alkoxy group)), $C_{1-4}$ alkylcarbonyl(N—$C_{1-4}$ alkyl)amino group (the alkylcarbonyl(N-alkyl)amino group may be optionally substituted with a halogen atom), $C_{1-4}$ alkoxycarbonyl group (the alkoxycarbonyl group may be optionally substituted with a halogen atom), $C_{6-10}$ arylcarbonylamino group (the arylcarbonylamino group may be substituted with a halogen atom, $C_{1-4}$ alkyl group, $C_{1-4}$ alkoxy group, cyano group or nitro group), $C_{6-10}$ arylcarbonyl(N—$C_{1-4}$ alkyl)amino group (the arylcarbonyl(N-alkyl)amino group may be substituted with a halogen atom, $C_{1-4}$ alkyl group, $C_{1-4}$ alkoxy group, cyano group or nitro group), benzylcarbonylamino group, formyl group, carbamoyl group, $C_{1-4}$ alkylsulfonyl group, $C_{6-10}$ arylsulfony group (the alkylsulfonyl group and arylsulfony group may be substituted with a halogen atom, $C_{1-4}$ alkyl group, $C_{1-4}$ alkoxy group, cyano group or nitro group), sulfamoyl group, $C_{1-4}$ alkylsulfonamide group, $C_{6-10}$ arylsulfonamide group (the alkylsulfonamide group and arylsulfonamide group may be substituted with a halogen atom, $C_{1-4}$ alkyl group, $C_{1-4}$ alkoxy group, cyano group or nitro group), bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis($C_{6-10}$ arylsulfone)imide group (arylsulfone of the bis(arylsulfone)imide group may be substituted with a halogen atom, $C_{1-4}$ alkyl group, $C_{1-4}$ alkoxy group, cyano group or nitro group), or (N,N'-($C_{1-4}$ alkylsulfone) ($C_{6-10}$ arylsulfone))imide group (alkylsulfone and arylsulfone of the (N,N'-(alkylsulfone) (arylsulfone)) imide group may be substituted with a halogen atom, $C_{1-4}$ alkyl group, $C_{1-4}$ alkoxy group, cyano group or nitro group);

$R^9$ and $R^{10}$ in the formula (10) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

$R^9$ and $R^{10}$ in the formula (11) and formula (12) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom) or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom, $C_{1-6}$ alkoxy group (the alkoxy group may be optionally substituted with a halogen atom) or hydroxy group) or $C_{1-6}$ alkoxy group (the alkoxy group may be optionally substituted with a halogen atom));

partial ring structure A in the formula (11) and formula (12) represents a partial structure being represented by 5-, 6- or 7-membered ring forming a fused ring with benzene ring part (each of the 5-, 6- and 7-membered rings may be optionally substituted with h $R^{11}$ ($R^{11}$ is a halogen atom, hydroxy group, $C_{1-6}$ alkyl group (the alkyl group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-6}$ alkoxy group (the alkoxy group may be optionally substituted with a halogen atom, hydroxy group, cyano group, amino group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), nitro group, cyano group, formyl group, formamide group, carbamoyl group, sulfo group, sulfoamino group, sulfamoyl group, sulfonyl group, amino group, carboxyl group, $C_{1-6}$ alkylamino group, di-$C_{1-6}$ alkylamino group, $C_{1-6}$ alkylcarbonylamino group, $C_{1-6}$ alkylsulfonamide group, $C_{6-14}$ arylsulfonamide group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, $C_{1-6}$ alkylsulfonyl group, $C_{6-14}$ arylsulfonyl group, or $C_{6-14}$ arylcarbonyl group (the alkylamino group, dialkylamino group, alkylcarbonylamino group, alkylsulfonamide group, arylsulfonamide group, alkylaminocarbonyl group, dialkylaminocarbonyl group, alkylcarbonyl group, alkoxycarbonyl group, alkylsulfonyl group, arylsulfonyl group, and arylcarbonyl group may be optionally substituted with a halogen atom); h is an integer of 1 to 6 and when h is an integer of 2 to 6, each $R^{11}$ may be the same or different); 1 to 3 of oxygen atom(s), nitrogen atom(s) or sulfur atom(s) can be contained singly or in combination as constituent atoms of the ring; the number of unsaturated bond(s) in the ring containing unsaturated bond(s) in benzene ring condensed is 1, 2 or 3 and carbon atom(s) composing the ring may be carbonyl or thiocarbonyl);

X in the formula (13) represents $NR^{20}$ ($R^{20}$ means a hydrogen atom or $C_{1-4}$ alkyl group);

Y in the formula (13) represents a bond, SO or $SO_2$;

Z in the formula (13) represents a $C_{1-4}$ alkyl group (the alkyl group may be optionally substituted with 1 to 5 halogen atom(s) or a phenyl group (the phenyl group may be optionally substituted with a $C_{1-4}$ alkyl group)) or phenyl group (the phenyl group may be optionally substituted with a $C_{1-4}$ alkyl group);

W in the formula (13) represents a hydrogen atom, hydroxy group, $C_{1-6}$ alkoxy group (the alkoxy group may be optionally substituted with a halogen atom), halogen atom, $C_{1-4}$ alkyl group or $C_{1-6}$ alkylsulfonamide group (the alkyl group and alkylsulfonamide group may be optionally substituted with a halogen atom); and $R^9$ and $R^{10}$ in the formula (13) each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), or hydroxy group), or $C_{6-14}$ aryl group (the aryl group may be optionally substituted with a halogen atom, hydroxy group, nitro group, cyano group, $C_{1-6}$ alkyl group (the alkyl group may be optionally substituted with a halogen atom or $C_{1-6}$ alkoxy group (the alkoxy group may be optionally substituted with a halogen atom) or hydroxy group) or $C_{1-6}$ alkoxy group (the alkoxy group may be optionally substituted with a halogen atom)));

by using any of optically active titanium complexes represented by the formula (1), formula (1'), formula (2), formula (2'), formula (3), formula (3'), formula (4) and formula (4') as a catalyst,

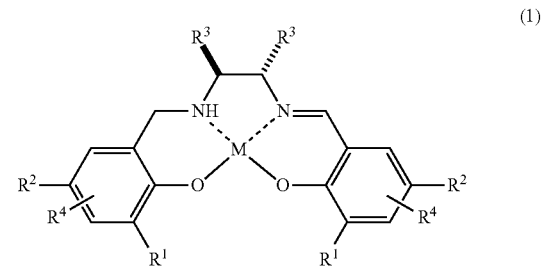

(1)

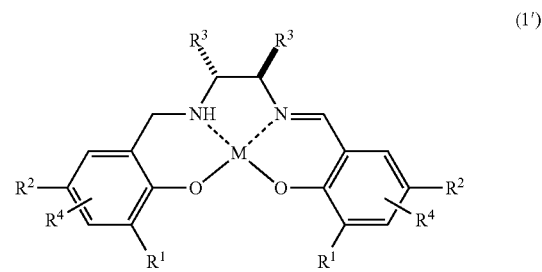

(1')

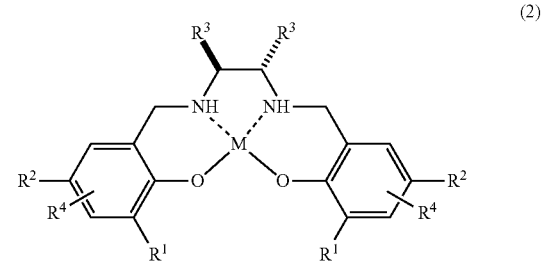

(2)

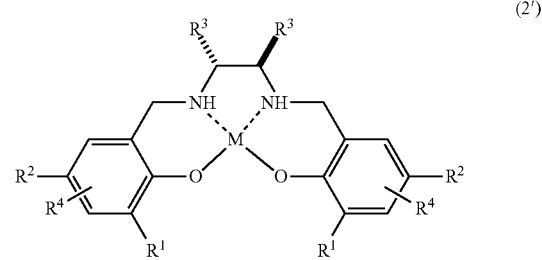

(2')

(3)
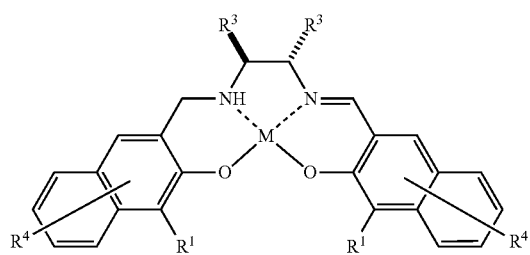

(3')
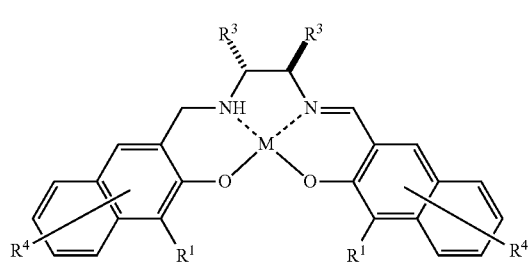

(4)
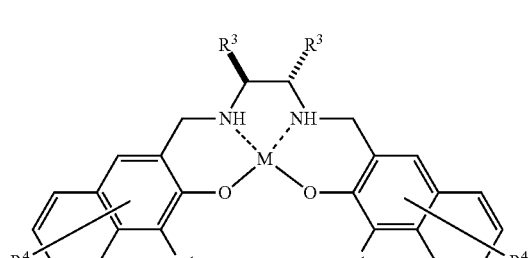

(4')
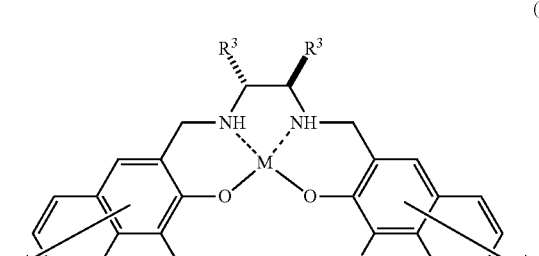

wherein $R^1$ in the formula (1), formula (1'), formula (2), formula (2'), formula (3), formula (3'), formula (4) and formula (4') represents a hydrogen atom, halogen atom, $C_{1-4}$ alkyl group, $C_{1-4}$ alkoxy group, $C_{6-12}$ aryloxy group, or $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group, and is optically active or optically non-active);

$R^2$ represents a hydrogen atom, halogen atom, $C_{1-4}$ alkyl group, $C_{1-4}$ alkoxy group, $C_{6-12}$ aryloxy group, or $C_{6-18}$ aryl group;

$R^3$ represents a $C_{1-4}$ alkyl group, $C_{6-18}$ aryl group, or $C_{3-5}$ bivalent group when two $R^3$ form a ring together;

$R^4$ each independently represent a hydrogen atom, halogen atom, $C_{1-4}$ alkyl group, $C_{1-4}$ alkoxy group, nitro group or cyano group;

M represents $TiJ^1J^2$ (in $TiJ^1J^2$, Ti represents a titanium atom, and $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group, (5)
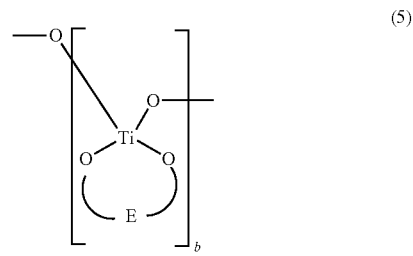

(wherein, in partial structure of O-E-O, O represents an oxygen atom and O-E-O is represented by following formula (6) in formula (1); O-E-O is represented by following formula (6') in formula (1'); O-E-O is represented by following formula (7) in formula (2); O-E-O is represented by following formula (7') in formula (2'); O-E-O is represented by following formula (8) in formula (3); O-E-O is represented by following formula (8') in formula (3'); O-E-O is represented by following formula (9) in formula (4); and O-E-O is represented by following formula (9') in formula (4'); and (6)
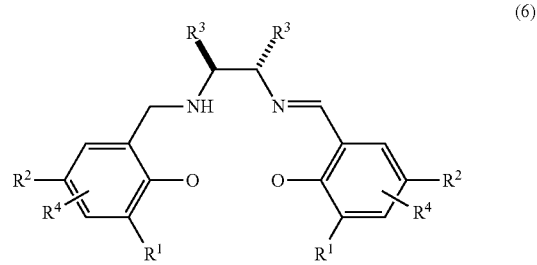

(6')
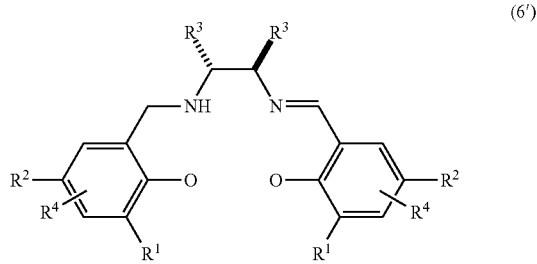

(7)
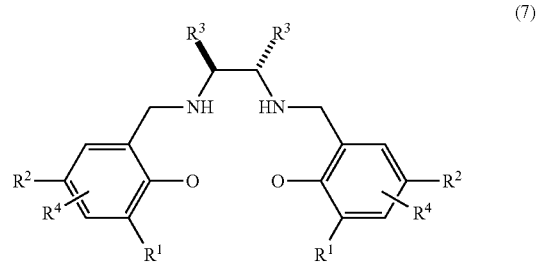

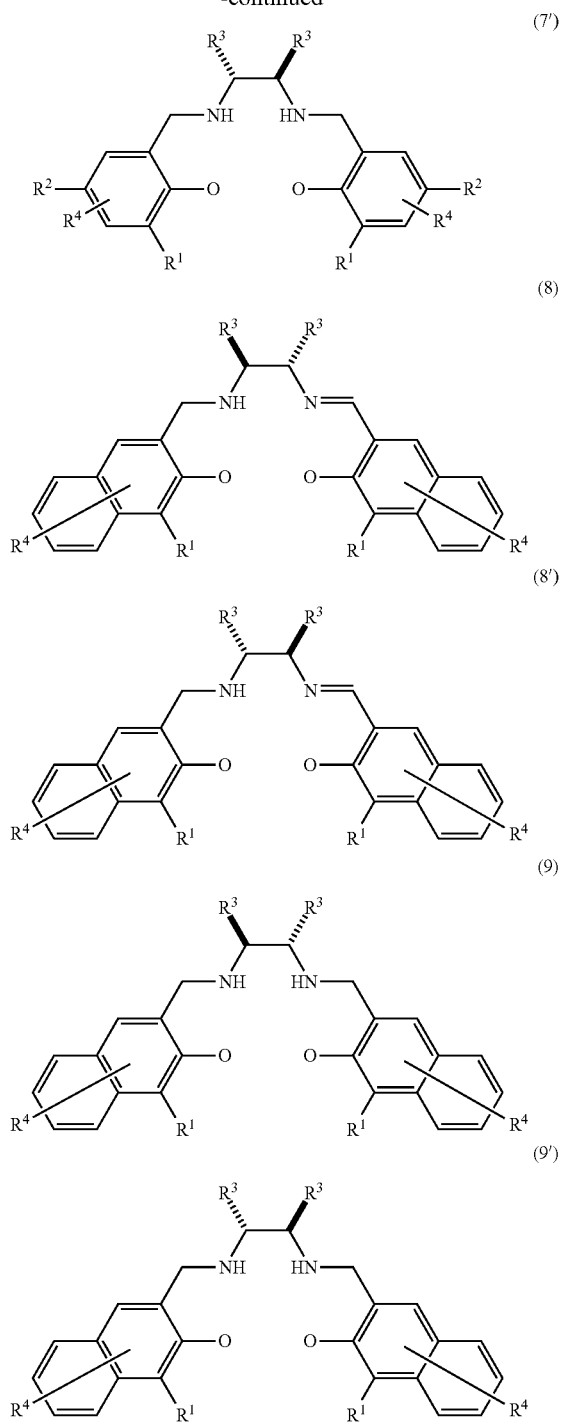

b represents an integer of 1 to 10; and $R^1$, $R^2$, $R^3$ and $R^4$ are the same as described above)).

2. The process for producing an optically active chromene oxide compound according to claim 1, wherein the chromene compound represented by the formula (10) is asymmetrically epoxidized in a solvent with oxidizing reagent by using an optically active titanium complex represented by any of the formula (1), formula (1'), formula (2), formula (2'), formula (3), formula (3'), formula (4) and formula (4') as a catalyst; wherein $R^5$ and $R^6$ in the formula (10) each independently represent a hydrogen atom, cyano group, nitro group, halogen atom, $C_{1-4}$ alkyl group (the alkyl group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkoxy group (the alkoxy group may be optionally substituted with a halogen atom, hydroxy group, cyano group, nitro group, $C_{1-4}$ alkoxy group, $C_{1-4}$ alkylcarbonyloxy group, $C_{1-4}$ alkylcarbonylamino group or $C_{1-4}$ alkoxycarbonyl group (the alkoxy group, alkylcarbonyloxy group, alkylcarbonylamino group and alkoxycarbonyl group may be optionally substituted with a halogen atom)), $C_{1-4}$ alkylcarbonylamino group (the alkylcarbonylamino group may be optionally substituted with a halogen atom), $C_{1-4}$ alkylcarbonyl(N—$C_{1-4}$ alkyl)amino group (the alkylcarbonyl (N-alkyl)amino group may be optionally substituted with a halogen atom), $C_{6-10}$ arylcarbonyl(N—$C_{1-4}$ alkyl)amino group (the arylcarbonyl(N-alkyl)amino group may be substituted with a halogen atom, $C_{1-4}$ alkyl group, $C_{1-4}$ alkoxy group, cyano group or nitro group), carbamoyl group, bis($C_{1-4}$ alkylsulfone)imide group (alkylsulfone of the bis (alkylsulfone)imide group may be substituted with a halogen atom, $C_{1-4}$ alkyl group, $C_{1-4}$ alkoxy group, cyano group or nitro group), bis ($C_{6-10}$ arylsulfone)imide group (arylsulfone of the bis (arylsulfone)imide group may be substituted with a halogen atom, $C_{1-4}$ alkyl group, $C_{1-4}$ alkoxy group, cyano group or nitro group), or (N,N'-($C_{1-4}$ alkylsulfone) ($C_{6-10}$ arylsulfone))imide group (alkylsulfone and arylsulfone of the (N,N'-(alkylsulfone) (arylsulfone)) imide group may be substituted with a halogen atom, $C_{1-4}$ alkyl group, $C_{1-4}$ alkoxy group, cyano group or nitro group);

$R^7$ in the formula (10) represents a hydrogen atom, cyano group, nitro group, bis($C_{1-4}$ alkylsulfone)imide group (alkylsulfone of the bis(alkylsulfone)imide group may be substituted with a halogen atom, $C_{1-4}$ alkyl group, $C_{1-4}$ alkoxy group, cyano group or nitro group), bis ($C_{6-10}$ arylsulfone)imide group (arylsulfone of the bis (arylsulfone)imide group may be substituted with a halogen atom, $C_{1-4}$ alkyl group, $C_{1-4}$ alkoxy group, cyano group or nitro group), or (N,N'-($C_{1-4}$ alkylsulfone)($C_{6-10}$ arylsulfone))imide group (alkylsulfone and arylsulfone of the (N,N'-(alkylsulfone)(arylsulfone)) imide group may be substituted with a halogen atom, $C_{1-4}$ alkyl group, $C_{1-4}$ alkoxy group, cyano group or nitro group);

$R^8$ in the formula (10) represents a hydrogen atom, nitro group, or $C_{1-4}$ alkyl group (the alkyl group may be optionally substituted with a halogen atom); and $R^9$ and $R^{10}$ in the formula (10) represent a $C_{1-6}$ alkyl group (the alkyl group may be optionally substituted with a halogen atom).

3. The process for producing an optically active chromene oxide compound according to claim 2, wherein $R^5$ and $R^6$ in the formula (10) each independently represent a hydrogen atom, nitro group, fluorine atom, methoxy group, methylcarbonylamino group or methylcarbonyl(N-ethyl)amino group; $R^7$ in the formula (10) represents a hydrogen atom, nitro group or bis($C_{1-4}$ alkylsulfone)imide group; $R^8$ in the formula (10) represents a hydrogen atom, nitro group or trifluoromethyl group; and $R^9$ and $R^{10}$ in the formula (10) represent a methyl group.

4. The process for producing an optically active chromene oxide compound according to claim 1, wherein the chromene compound represented by the formula (11) or (12) whose partial ring structure A is represented by any of the formula (a), formula (b), formula (c), formula (d), formula (e), formula (f), formula (g), formula (h), formula (i), formula (j), formula (k), formula (l), formula (m), formula (n), formula (o), formula (p), formula (q), formula (r), formula (s), formula (t), formula (u), formula (v), formula (w), formula (x), formula (y), formula (z), formula (aa), formula (ab), formula (ac), formula (ad), formula (ae), formula (af), formula (ag), and formula (ah) is asymmetrically epoxidized in a solvent with oxidizing reagent by using any of the optically active titanium complex represented by the formula (1), formula (1'), formula (2), formula (2'), formula (3), formula (3'), formula (4) and formula (4') as a catalyst,

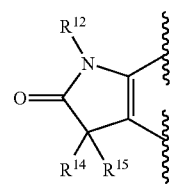 (a)

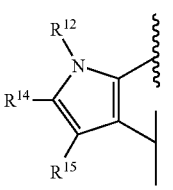 (b)

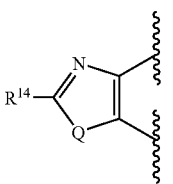 (c)

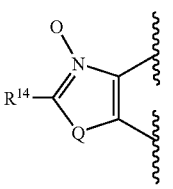 (d)

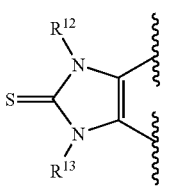 (e)

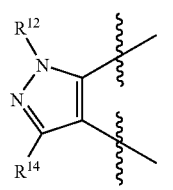 (f)

-continued

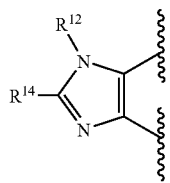 (g)

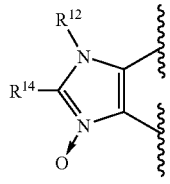 (h)

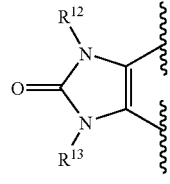 (i)

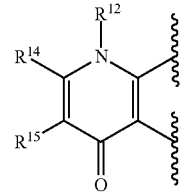 (j)

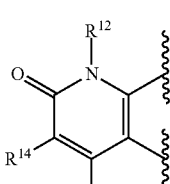 (k)

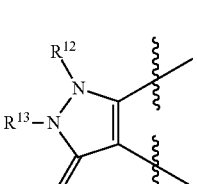 (l)

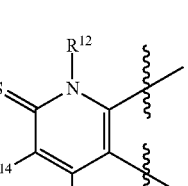 (m)

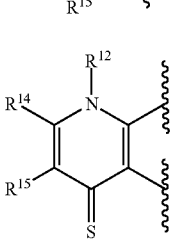 (n)

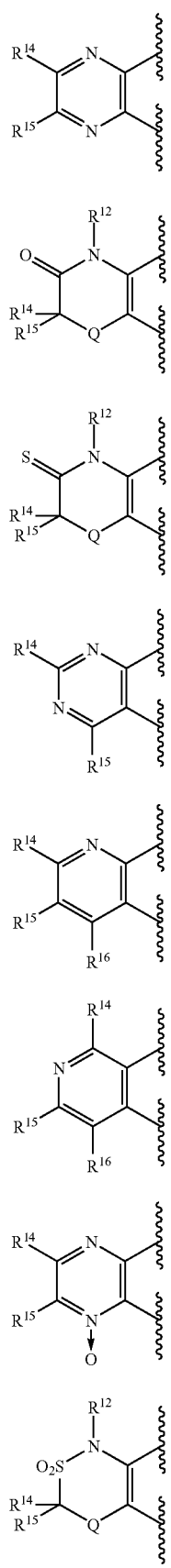
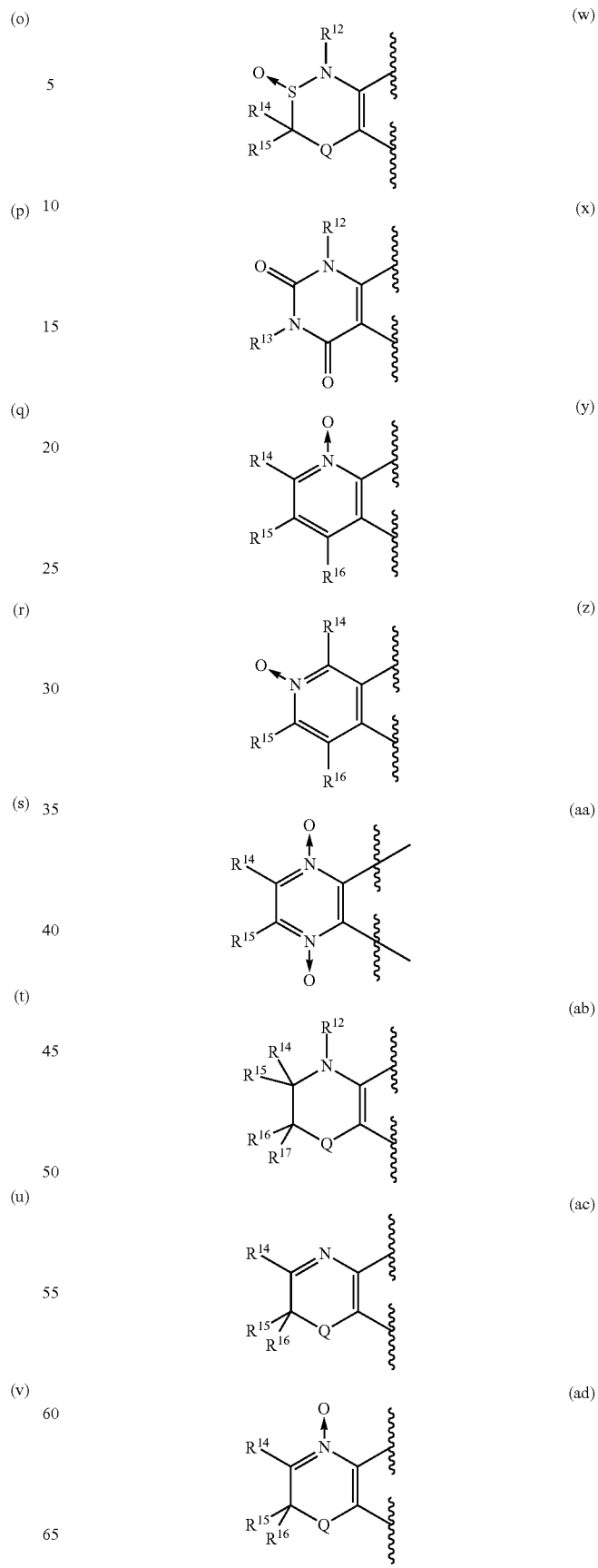

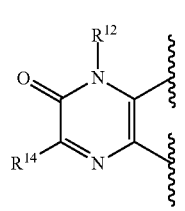
(ae)

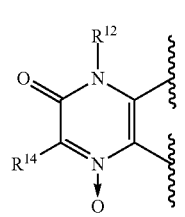
(af)

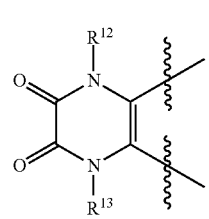
(ag)

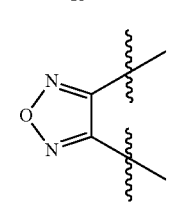
(ah)

(wherein $R^{12}$ and $R^{13}$ each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group or $C_{2-9}$ heteroaryl group (each of the aryl group and heteroaryl group may be optionally substituted with q $R^{18}$ ($R^{18}$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom) or $C_{2-9}$ heteroarylcarbonyl group), $C_{6-14}$ aryl group, $C_{2-9}$ heteroaryl group (each of the aryl group and heteroaryl group may be optionally substituted with q $R^{18}$ ($R^{18}$ represents the same meaning of $R^{11}$; q represents an integer of 1 to 3, and each $R^{18}$ may be the same or different when q is 2 or 3)), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, $C_{6-14}$ arylsulfonyl group, $C_{2-9}$ heteroarylsulfonyl group (each of the arylsulfonyl group and heteroarylsulfonyl group may be optionally substituted with q $R^{18}$ ($R^{18}$ represents the same meaning of $R^{11}$; q represents an integer of 1 to 3, and each $R^{18}$ may be the same or different when q is 2 or 3)), carboxyl group, $C_{6-14}$ arylcarbonyl group, or $C_{2-9}$ heteroarylcarbonyl group (each of the arylcarbonyl group and heteroarylcarbonyl group may be optionally substituted with q $R^{18}$ ($R^{18}$ represents the same meaning of $R^{11}$; q represents an integer of 1 to 3, and each $R^{18}$ may be the same or different when q is 2 or 3));

$R^{14}$, $R^{15}$, $R^{16}$ and $R^{17}$ each independently represent a hydrogen atom, halogen atom, $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group, $C_{1-6}$ alkoxycarbonyl group, $C_{1-6}$ alkylsulfonyl group (the cycloalkylcarbonyl group, alkoxycarbonyl group and alkylsulfonyl group may be optionally substituted with a halogen atom), carboxyl group, $C_{6-14}$ arylcarbonyl group (the arylcarbonyl group may be optionally substituted with a halogen atom), or $C_{2-9}$ heteroarylcarbonyl group), $C_{3-8}$ cycloalkyl group (the cycloalkyl group may be optionally substituted with a halogen atom, $C_{1-6}$ alkoxy group (the alkoxy group may be optionally substituted with a halogen atom), amino group or hydroxy group), $C_{1-6}$ alkoxy group (the alkoxy group may be optionally substituted with a halogen atom, $C_{1-6}$ alkoxy group (the alkoxy group may be optionally substituted with a halogen atom), carboxyl group, amino group, hydroxy group, $C_{6-14}$ aryl group or $C_{2-9}$ heteroaryl group (each of the aryl group and heteroaryl group may be optionally substituted with r $R^{19}$ ($R^{19}$ represents the same meaning of $R^{11}$; r represents the same meaning of q))), $C_{1-6}$ thioalkoxy group (the thioalkoxy group may be optionally substituted with a halogen atom, $C_{1-6}$ alkoxy group (the alkoxy group may be optionally substituted with a halogen atom), carboxyl group, hydroxy group, $C_{6-14}$ aryl group or $C_{2-9}$ heteroaryl group (each of the aryl group and heteroaryl group may be optionally substituted with r $R^{19}$ ($R^{19}$ represents the same meaning of $R^{11}$; r represents the same meaning of q))), hydroxy group, $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), $C_{1-6}$ alkylcarbonyloxy group, nitro group, cyano group, formyl group, formamide group, amino group, sulfo group, $C_{1-6}$ alkylamino group, di-$C_{1-6}$ alkylamino group, $C_{6-14}$ arylamino group, $C_{2-9}$ heteroarylamino group (each of the arylamino group and the heteroarylamino group may be optionally substituted with r $R^{19}$ ($R^{19}$ represents the same meaning of $R^{11}$; r represents the same meaning of q)), $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{6-14}$ arylcarbonyl group, $C_{2-9}$ heteroarylcarbonyl group (each of the arylcarbonyl group and heteroarylcarbonyl group may be optionally substituted with r $R^{19}$ ($R^{19}$ represents the same meaning of $R^{11}$; r represents the same meaning of q)), $C_{1-6}$ alkoxycarbonyl group, sulfamoyl group, $C_{1-6}$ alkylsulfonyl group, $C_{6-14}$ arylsulfonyl group, $C_{2-9}$ heteroarylsulfonyl group (each of the arylsulfonyl group and heteroarylsulfonyl group may be optionally substituted with r $R^{19}$ ($R^{19}$ represents the same meaning of $R^{11}$; r represents the same meaning of q)), carboxyl group or $C_{2-9}$ heterocyclyl group (the heterocyclyl group may be optionally substituted with a halogen atom, $C_{1-6}$ alkyl group (the alkyl group may be optionally substituted with a halogen atom, $C_{1-6}$ alkoxy group (the alkoxy group may be optionally substituted with a halogen atom), amino group, carboxyl group or hydroxy group), $C_{1-6}$ alkoxy group (the alkoxy group may be optionally substituted with a halogen atom), $C_{6-14}$ aryl group, $C_{2-9}$ heteroaryl group (each of the aryl group and heteroaryl group may be optionally substituted with r $R^{19}$ ($R^{19}$ represents the same meaning of $R^{11}$; r represents the same meaning of q)), hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonamide group, carbamoyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, sulfamoyl group, $C_{1-6}$ alkylsulfonyl group, carboxyl group or $C_{6-14}$ arylcarbonyl group); and Q in the formula (c), formula (d), formula (p), formula (q), formula (v), formula (w), formula (ab), formula (ac) and formula (ad) represents O (oxygen atom), S (sulfur atom), SO (sulfinyl group) or $SO_2$ (sulfonyl group)).

5. The process for producing an optically active chromene oxide compound according to claim 4, wherein $R^9$ and $R^{10}$ in the formula (11) or the formula (12) are methyl group.

6. The process for producing an optically active chromene oxide compound according to claim 4, wherein A in the formula (11) or the formula (12) is represented by the following formula (a), formula (b), formula (i), formula (k), formula (o), formula (p), formula (s), formula (v), formula (y), formula (ae), formula (ag) and formula (ah),

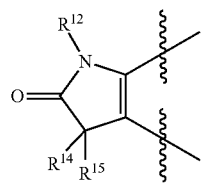
(a)

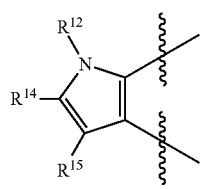
(b)

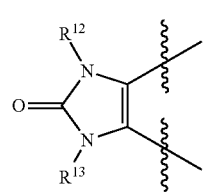
(i)

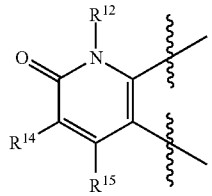
(k)

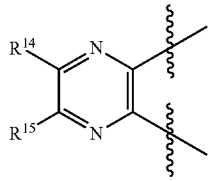
(o)

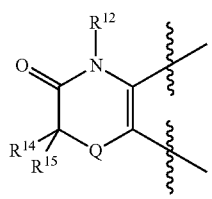
(p)

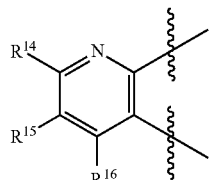
(s)

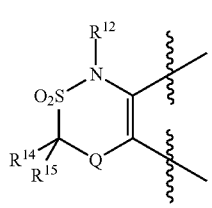
(v)

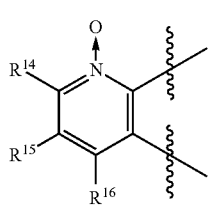
(y)

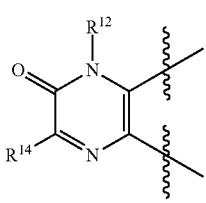
(ae)

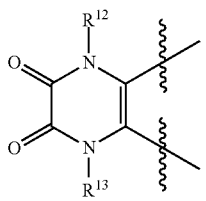
(ag)

-continued

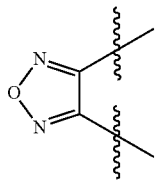

(ah)

(wherein $R^{12}$, $R^{13}$, $R^{14}$, $R^{15}$ and $R^{16}$ are the same as in claim 4).

7. The process for producing an optically active chromene oxide compound according to claim 6, wherein A in the formula (11) or the formula (12) represents the formula (a), formula (b), formula (i), formula (k), formula (o), formula (p), formula (s), formula (v), formula (y), formula (ae), formula (ag) and formula (ah); $R^{12}$ and $R^{13}$ each independently represent a hydrogen atom, $C_{1-6}$ alkyl group (the alkyl group may be optionally substituted with a halogen atom, $C_{1-6}$ alkoxy group (the alkoxy group may be optionally substituted with a halogen atom), amino group or hydroxy group), and $R^{14}$, $R^{15}$ and $R^{16}$ each independently represent a hydrogen atom, halogen atom or $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group or $C_{1-6}$ alkoxycarbonyl group); and Q represents O (oxygen atom).

8. The process for producing an optically active chromene oxide compound according to claim 7, wherein A in the formula (11) or the formula (12) represents the formula (a), formula (b), formula (i), formula (k), formula (o), formula (p), formula (s), formula (v), formula (y), formula (ae), formula (ag) or formula (ah), and $R^{12}$ and $R^{13}$ each independently represent a hydrogen atom or methyl group, and $R^{14}$, $R^{15}$ and $R^{16}$ each independently represent a hydrogen atom, halogen atom or $C_{1-6}$ alkyl group (the alkyl group may be optionally substituted with a halogen atom, $C_{1-6}$ alkoxy group (the alkoxy group may be optionally substituted with a halogen atom), amino group, hydroxy group, $C_{1-6}$ alkylaminocarbonyl group, di-$C_{1-6}$ alkylaminocarbonyl group, $C_{1-6}$ alkylcarbonyloxy group, $C_{1-6}$ alkylcarbonyl group (the alkylcarbonyloxy group and alkylcarbonyl group may be optionally substituted with a halogen atom), $C_{1-6}$ alkylcarbonylamino group, $C_{3-8}$ cycloalkylcarbonyl group or $C_{1-6}$ alkoxycarbonyl group); and Q represents O (oxygen atom).

9. The process for producing an optically active chromene oxide compound according to claim 1, wherein the chromene compound represented by the formula (13) is asymmetrically epoxidized in a solvent with oxidizing reagent by using an optically active titanium complex represented by any of formula (1), formula (1'), formula (2), formula (2'), formula (3), formula (3'), formula (4) and formula (4') as a catalyst, and both $R^9$ and $R^{10}$ in the formula (13) represent a methyl group.

10. The process for producing an optically active chromene oxide compound according to claim 9, wherein W in the formula (13) represents a hydrogen atom, hydroxy group, methoxy group, chlorine atom, bromine atom, methyl group, ethyl group or methanesulfonamide group.

11. The process for producing an optically active chromene oxide compound according to claim 9, in which Y in the formula (13) represents $SO_2$ (sulfonyl group) and Z represents a $C_{1-4}$ alkyl group.

12. The process for producing an optically active chromene oxide compound according to claim 10, wherein Y in the formula (13) represents a bond and Z represents a $C_{1-4}$ alkyl group.

13. The process for producing an optically active chromene oxide compound according to claim 1, wherein $R^1$ in the formula (1), formula (1'), formula (2), formula (2'), formula (3), formula (3'), formula (4) and formula (4') represents a $C_{6-22}$ aryl group (the aryl group may be optionally substituted with a $C_{1-4}$ alkyl group (the alkyl group may be optionally substituted with a halogen atom), $C_{1-7}$ alkoxy group or benzyloxy group and is optically active or optically non-active);
$R^2$ represents a hydrogen atom, halogen atom, $C_{1-4}$ alkyl group, $C_{1-4}$ alkoxy group, $C_{6-12}$ aryloxy group or $C_{6-18}$ aryl group;
$R^3$ represents a $C_{1-4}$ alkyl group, $C_{6-18}$ aryl group or $C_{3-5}$ bivalent group when two $R^3$ form a ring together;
$R^4$ each independently represents a hydrogen atom, halogen atom, $C_{1-4}$ alkyl group, $C_{1-4}$ alkoxy group, nitro group or cyano group; and
M represents $TiJ^1J^2$,
(wherein Ti is titanium atom; $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group,
(wherein, in partial structure of O-E-O, O represents an oxygen atom and O-E-O is represented by the formula (6) in formula (1); O-E-O is represented by the formula (6') in formula (1'); O-E-O is represented by the formula (7) in formula (2); O-E-O is represented by the formula (7') in formula (2'); O-E-O is represented by the formula (8) in formula (3); O-E-O is represented by the formula (8') in formula (3'); O-E-O is represented by the formula (9) in formula (4); O-E-O is represented by the formula (9') in formula (4'); b represents an integer of 1 to 10; and $R^1$, $R^2$, $R^3$ and $R^4$ are the same as described above)).

14. The process for producing an optically active chromene oxide compound according to claim 13, wherein $R^1$ in the formula (1), formula (1'), formula (2), formula (2'), formula (3), formula (3'), formula (4) and formula (4') is phenyl group (the phenyl group may be optionally substituted with a $C_{1-4}$ alkyl group (the alkyl group may be optionally substituted with a halogen atom), benzyloxy group or $C_{1-7}$ alkoxy group), or naphthyl group (the naphthyl group may be optionally substituted with a $C_{1-4}$ alkyl group (the alkyl group may be optionally substituted with a halogen atom), $C_{1-7}$ alkoxy group or phenyl group);
$R^2$ represents a hydrogen atom;
$R^3$ represents a $C_{3-5}$ bivalent group when two $R^3$ form a ring together;
$R^4$ represents a hydrogen atom; and
M represents $TiJ^1J^2$,
(wherein Ti is titanium atom; $J^1$ and $J^2$ each independently represent a halogen atom or $C_{1-4}$ alkoxide, or $J^1$ and $J^2$ are bonded together to represent an oxygen atom, or $J^1$ and $J^2$ are bonded together to form a ring represented by the formula (5) of bivalent group,
(wherein, in partial structure of O-E-O, O represents an oxygen atom and O-E-O is represented by the formula (6) in formula (1); O-E-O is represented by the formula (6') in formula (1'); O-E-O is represented by the formula (7) in formula (2); O-E-O is represented by the formula (7') in formula (2'); O-E-O is represented by the formula (8) in formula (3); O-E-O is represented by the formula (8') in formula (3'); O-E-O is represented by the formula (9) in formula (4); O-E-O is represented by the formula (9') in formula (4'); b represents an integer of 1 to 10; and $R^1$, $R^2$, $R^3$ and $R^4$ are the same as described above)).

15. The process for producing an optically active chromene oxide compound according to claim 1, wherein a used amount of the optically active titanium complex to an amount of chromene compound represented by the formula (10), formula (11), formula (12) or formula (13) is 0.001 to 100 mol %.

16. The process for producing an optically active chromene oxide compound according to claim 1, wherein the solvent used for the asymmetric epoxidation is a halogen-type solvent, an aromatic hydrocarbon-type solvent, an ester-type solvent, an ether-type solvent, a nitrile-type solvent, an alcohol-type solvent or a mixture thereof.

17. The process for producing an optically active chromene oxide compound according to claim 1, wherein the oxidizing reagent used for the asymmetric epoxidization reaction is iodosobenzene, sodium hypochlorite, m-chloroperbenzoic acid, Oxone (registered trademark of E. I. du Pont de Nemours and Company), hydrogen peroxide aqueous solution, urea-hydrogen peroxide adduct (UHP), oxaziridine, N-methylmorpholineoxide (NMO), t-butylhydroperoxide (TBHP), cumenehydroperoxide (CHP) or a mixture thereof.

18. The process for producing an optically active chromene oxide compound according to claim 17, wherein the oxidizing reagent used for the asymmetric epoxidization reaction is hydrogen peroxide aqueous solution, urea-hydrogen peroxide adduct (UHP) or mixture thereof.

19. The process for producing an optically active chromene oxide compound according to claim 18, wherein the oxidizing reagent used for the asymmetric epoxidation is hydrogen peroxide aqueous solution and a concentration thereof is 1 to 100% by mass.

20. The process for producing an optically active chromene oxide compound according to claim 1, wherein a used amount of the oxidizing reagent used for the asymmetric epoxidation to an amount of chromene compound represented by the formula (10), formula (11), formula (12) or formula (13) is 1 to 10 equivalent.

21. The process for producing an optically active chromene oxide compound according to claim 20, wherein an addition method of the oxidizing reagent used for the asymmetric epoxidation is fractionated addition or continuous addition.

22. The process for producing an optically active chromene oxide compound according to claim 21, wherein the addition method of the oxidizing reagent used for the asymmetric epoxidation is the continuous addition and the addition rate is 0.01 to 40,000 equivalent per hour.

23. The process for producing an optically active chromene oxide compound according to claim 21, wherein the addition method of the oxidizing reagent used for the asymmetric epoxidation is fractionated addition and the number of fractions is in a range of 2 to 100.

24. The process for producing an optically active chromene oxide compound according to claim 1, wherein a reaction temperature of the asymmetric epoxidation is from 0° C. to a reflux temperature of the solvent used.

25. The process for producing an optically active chromene oxide compound according to claim 1, wherein a pressure of the asymmetric epoxidation in a reacting system is in a range of 10 kPa to 1,100 kPa.

\* \* \* \* \*